United States Patent
Nabatova-Gabain et al.

(10) Patent No.: US 8,199,336 B2
(45) Date of Patent: Jun. 12, 2012

(54) OPTICAL MEASUREMENT APPARATUS, SPECTROSCOPIC ELLIPSOMETER, RECORDING MEDIUM, AND MEASUREMENT METHOD

(75) Inventors: Nataliya Nabatova-Gabain, Manimi-ku (JP); Eric Minet, Longjumeau (FR)

(73) Assignee: Horiba, Ltd., Kyoto (JP)

( * ) Notice: Subject to any disclaimer, the term of this patent is extended or adjusted under 35 U.S.C. 154(b) by 426 days.

(21) Appl. No.: 12/613,359

(22) Filed: Nov. 5, 2009

(65) Prior Publication Data

US 2010/0121607 A1 May 13, 2010

(30) Foreign Application Priority Data

Nov. 8, 2008 (JP) ................. 2008-287232

(51) Int. Cl.
*G01B 11/28* (2006.01)
*G01J 4/00* (2006.01)

(52) U.S. Cl. .............. 356/630; 356/364; 356/369
(58) Field of Classification Search .......... 356/364–369, 356/360–362; 250/225
See application file for complete search history.

(56) References Cited

U.S. PATENT DOCUMENTS

| | | | | |
|---|---|---|---|---|
| 5,835,220 A | * | 11/1998 | Kazama et al. | 356/369 |
| 5,949,900 A | * | 9/1999 | Nakamura et al. | 382/145 |
| 7,196,793 B2 | * | 3/2007 | Nabatova-Gabain et al. | 356/369 |
| 7,280,208 B2 | | 10/2007 | Funakubo et al. | |
| 7,280,210 B2 | * | 10/2007 | Nabatova-Gabain et al. | 356/369 |
| 7,973,930 B2 | * | 7/2011 | Tanaka | 356/369 |
| 2004/0109173 A1 | | 6/2004 | Finarov et al. | |
| 2005/0174584 A1 | | 8/2005 | Chalmers et al. | |
| 2005/0185169 A1 | | 8/2005 | McMackin et al. | |
| 2006/0023213 A1 | | 2/2006 | Funakubo et al. | |

FOREIGN PATENT DOCUMENTS

JP 2004-286468 10/2004
WO 03/030250 4/2003

* cited by examiner

*Primary Examiner* — Sang Nguyen

(57) ABSTRACT

An optical measurement apparatus includes: a storage processing part storing into a storage part a plurality of main reference positions where measurement is to be performed and at least one movement value relative to each main reference position; a main measuring part moving a measurement position to one of the main reference positions stored in the storage part, then irradiating light, and then measuring a change in a state of reflected light; an auxiliary measuring part moving the measurement position to an auxiliary reference position based on the movement value relative to one of the main reference positions stored in the storage part, then irradiating light, and then measuring a change in a state of reflected light; a main calculating part performing analysis and calculating a film thickness or an optical constant; and an auxiliary calculating part performing analysis and calculating a film thickness or an optical constant.

20 Claims, 47 Drawing Sheets

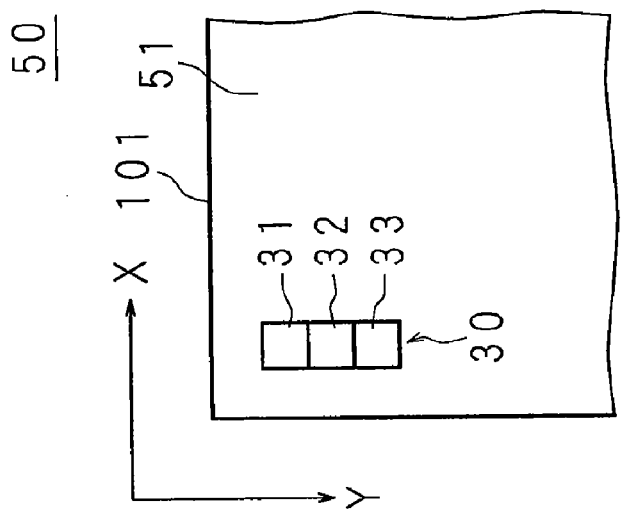
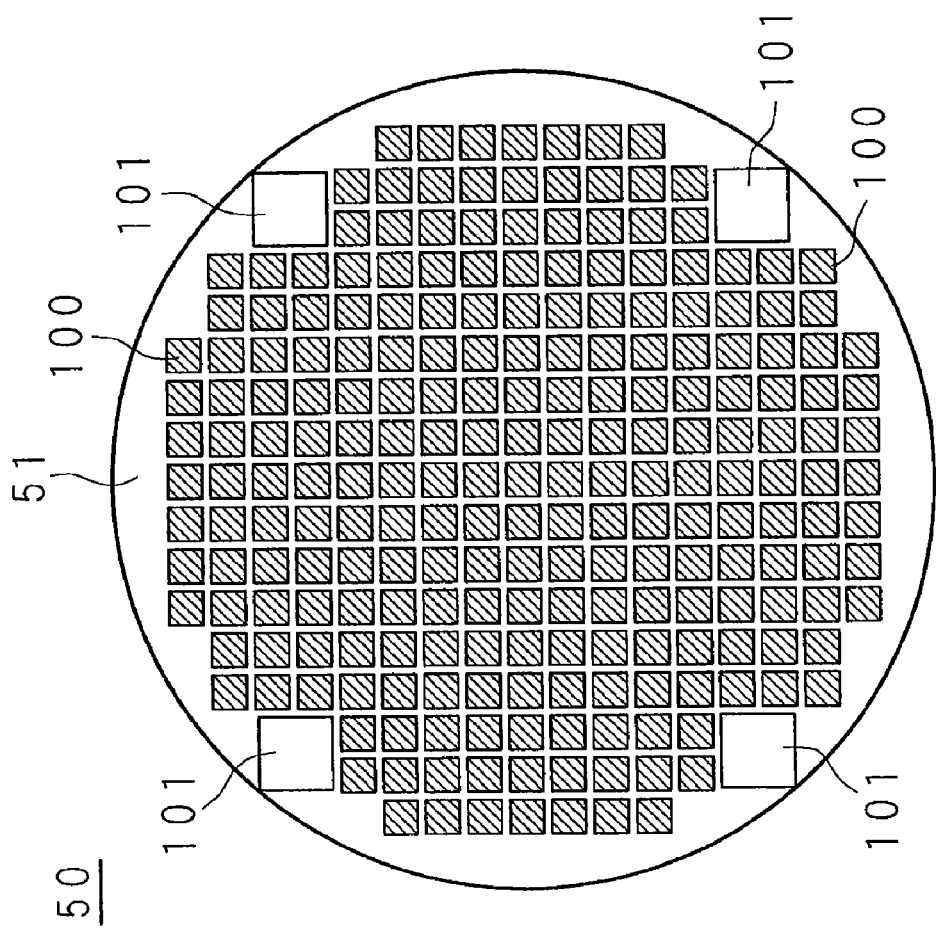

FIG. 6

COORDINATE VALUE FILE 151

| SET ID | FIRST STACK/ FIRST REFERENCE COORDINATES | SECOND STACK/ SECOND REFERENCE COORDINATES | THIRD STACK/ THIRD REFERENCE COORDINATES |
|---|---|---|---|
| 01 | (x1, y1) | (x1+Sx, y1+Ty) | (x1+Sx+Ux, y1+Ty+Vy) |
| 02 | (x2, y2) | (x2+Sx, y2+Ty) | (x2+Sx+Ux, y2+Ty+Vy) |
| 03 | (x3, y3) | (x3+Sx, y3+Ty) | (x3+Sx+Ux, y3+Ty+Vy) |

FIG. 7

ENTER CHECK MARKS FOR COMMON ITEMS

☐ FILM THICKNESS  ☐ OPTICAL CONSTANTS  301c
☑ FILM THICKNESS  ☑ OPTICAL CONSTANTS  300c 30
31
32
33
300

ENTER  41
CANCEL

FIG. 8

RESULT DB 152

| SET ID | | FILM | FIRST STACK | SECOND STACK | THIRD STACK | | | | |
|---|---|---|---|---|---|---|---|---|---|
| | | | MEASURED SPECTRA | FILM THICKNESS | ABNORMALITY FLAG | OPTICAL CONSTANTS | | | |
| | | | | | | REFRACTIVE INDEX | ABNORMALITY FLAG | EXTINCTION COEFFICIENT | ABNORMALITY FLAG |
| 01 | | SECOND FILM | ... | ... | | ... | | ... | ○ |
| | | COMMON FILM | ... | ... | ○ | ... | | ... | |
| 02 | | SECOND FILM | ... | ... | | ... | | ... | |
| | | COMMON FILM | ... | ... | | ... | | ... | |
| 03 | | SECOND FILM | ... | ... | | ... | ○ | ... | |
| | | COMMON FILM | ... | ... | | ... | | ... | |

F I G. 1 4

COORDINATE VALUE FILE 151

| SET ID | FIRST STACK/ FIRST REFERENCE COORDINATES | SECOND STACK/ SECOND REFERENCE COORDINATES |
|---|---|---|
| 01 | (x1, y1) | (x1+Sx, y1+Ty) |
| 02 | (x2, y2) | (x2+Sx, y2+Ty) |
| 03 | (x3, y3) | (x3+Sx, y3+Ty) |

FIG. 16

RESULT DB 152

| FIRST STACK | SECOND STACK | | | | OPTICAL CONSTANTS | | |
|---|---|---|---|---|---|---|---|
| SET ID | FILM | MEASURED SPECTRA | FILM THICKNESS | ABNORMALITY FLAG | REFRACTIVE INDEX | ABNORMALITY FLAG | EXTINCTION COEFFICIENT | ABNORMALITY FLAG |
| 01 | FIRST FILM | ... | ... | ○ | ... | | ... | ○ |
|  | LOWER LAYER FILM | ... | ... | | ... | | ... | |
| 02 | FIRST FILM | ... | ... | | ... | | ... | |
|  | LOWER LAYER FILM | ... | ... | | ... | | ... | |
| 03 | FIRST FILM | ... | ... | | ... | ○ | ... | |
|  | LOWER LAYER FILM | ... | ... | | ... | | ... | |

F I G. 1 9 B
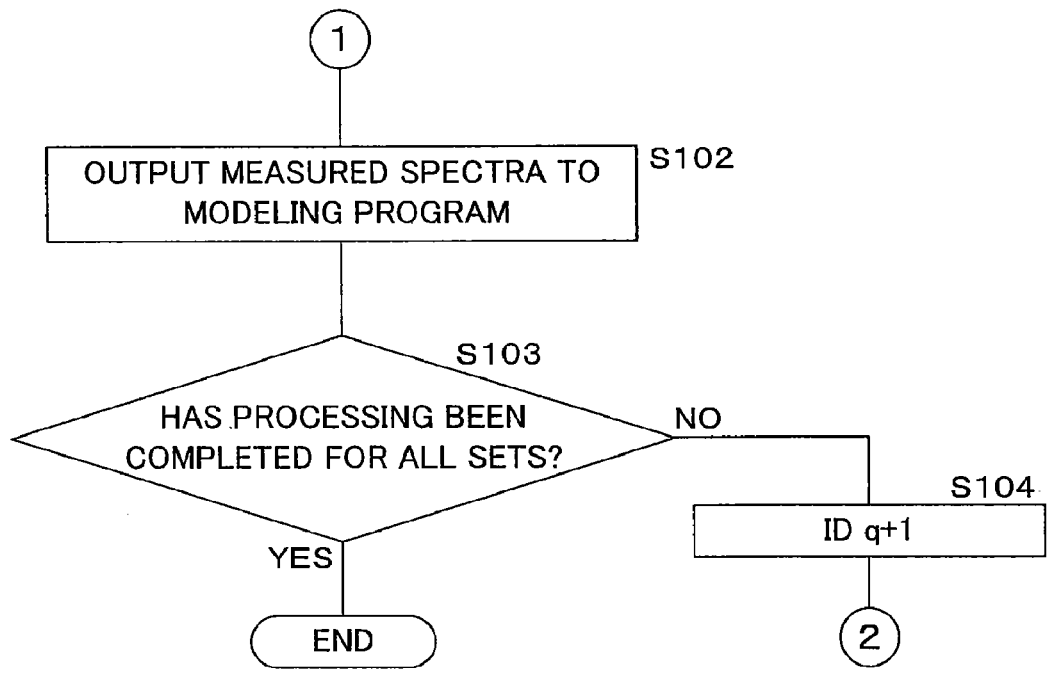

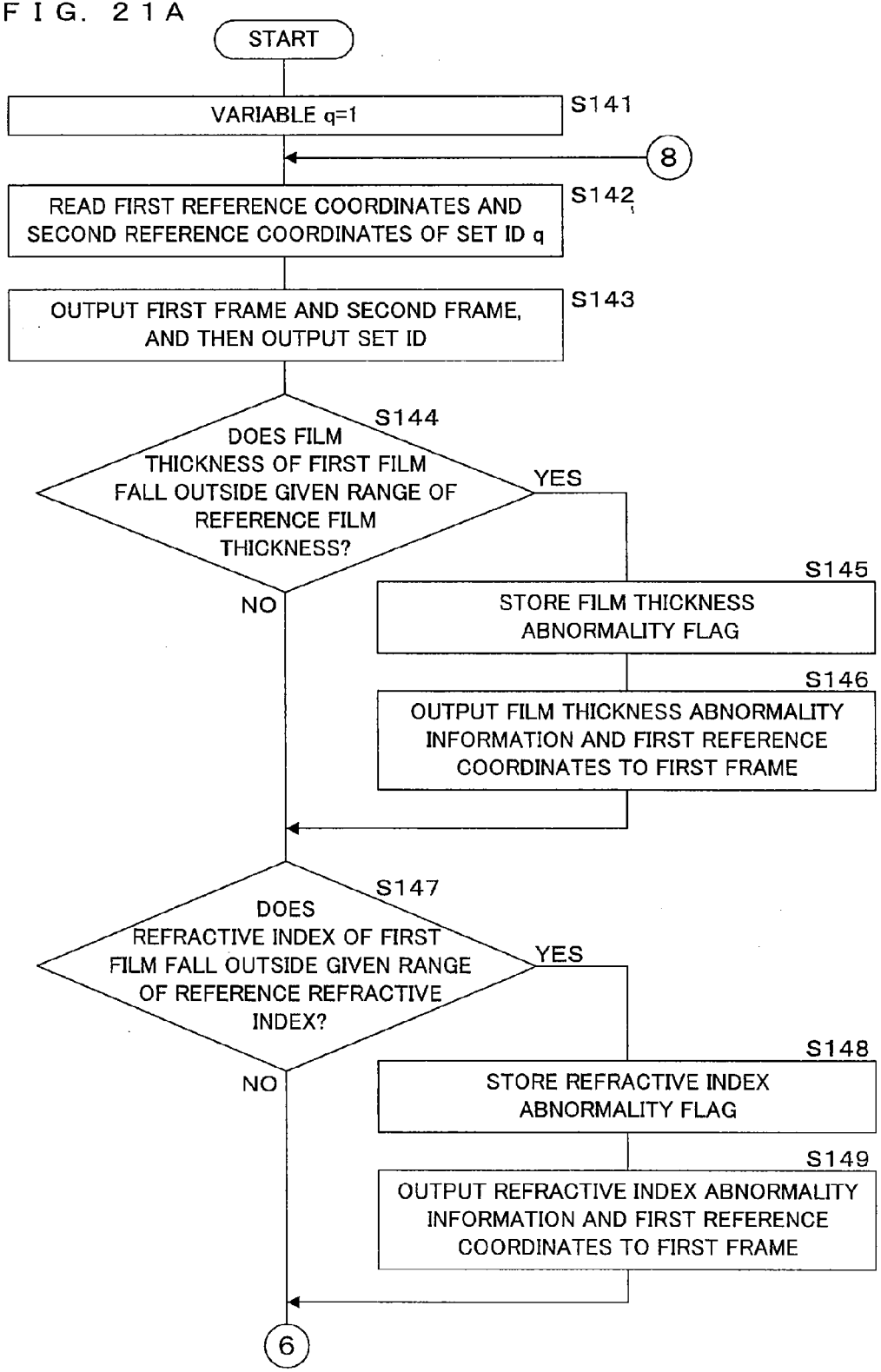

FIG. 23

ENTER CHECK MARKS FOR COMMON ITEMS

□ FILM THICKNESS  □ OPTICAL CONSTANTS   301c
☑ FILM THICKNESS  ☑ OPTICAL CONSTANTS   300c 30
32  302
31
301
300

41 ENTER    CANCEL

F I G. 24C
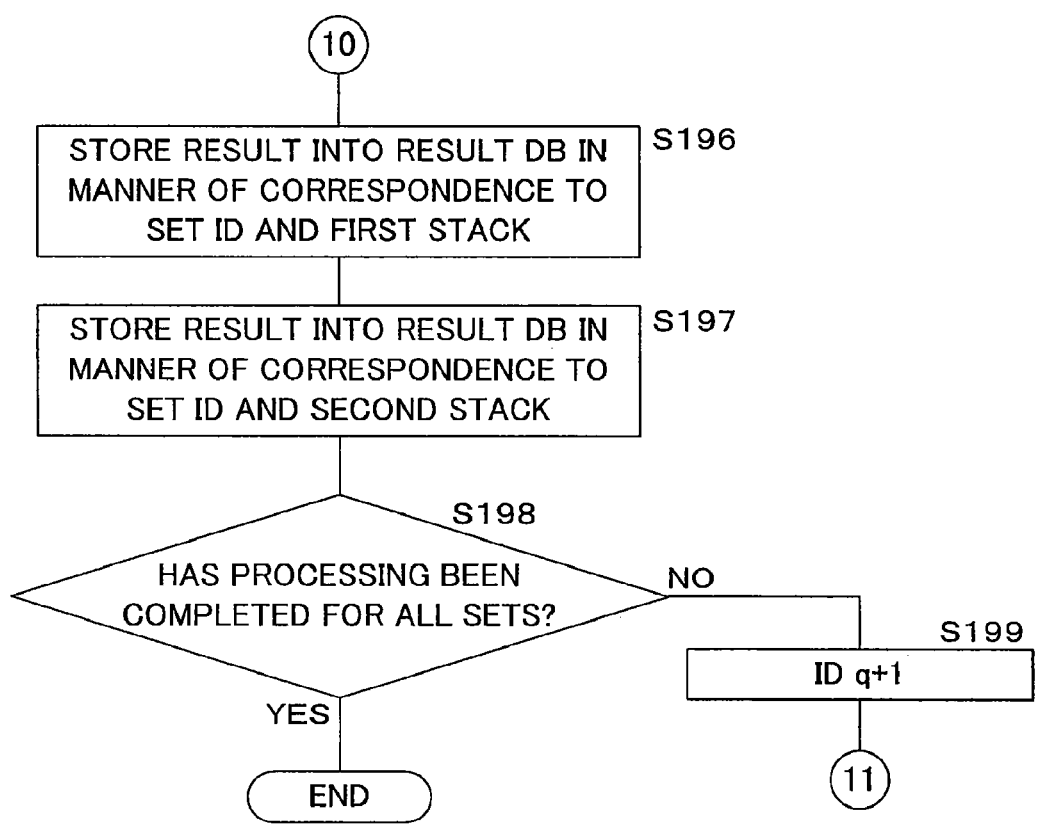

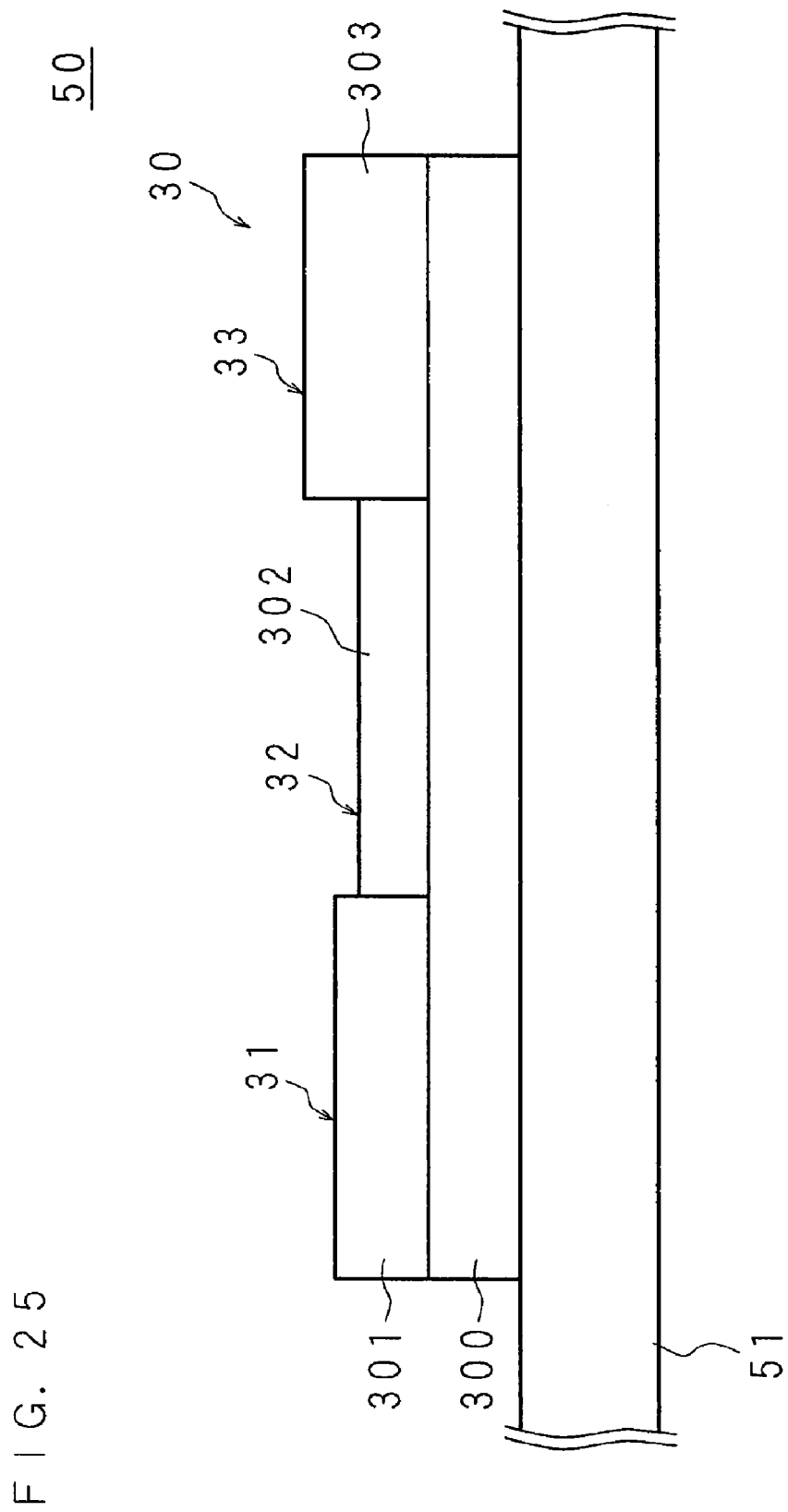

FIG. 27

COORDINATE VALUE FILE 151

| SET ID | FIRST STACK/ FIRST REFERENCE COORDINATES | SECOND STACK/ SECOND REFERENCE COORDINATES | THIRD STACK/ THIRD REFERENCE COORDINATES |
|---|---|---|---|
| 01 | (x1, y1) | (x1+Sx, y1+Ty) | (x1+Sx+Ux, y1+Ty+Vy) |
| 02 | (x2, y2) | (x2+Sx, y2+Ty) | (x2+Sx+Ux, y2+Ty+Vy) |
| 03 | (x3, y3) | (x3+Sx, y3+Ty) | (x3+Sx+Ux, y3+Ty+Vy) |

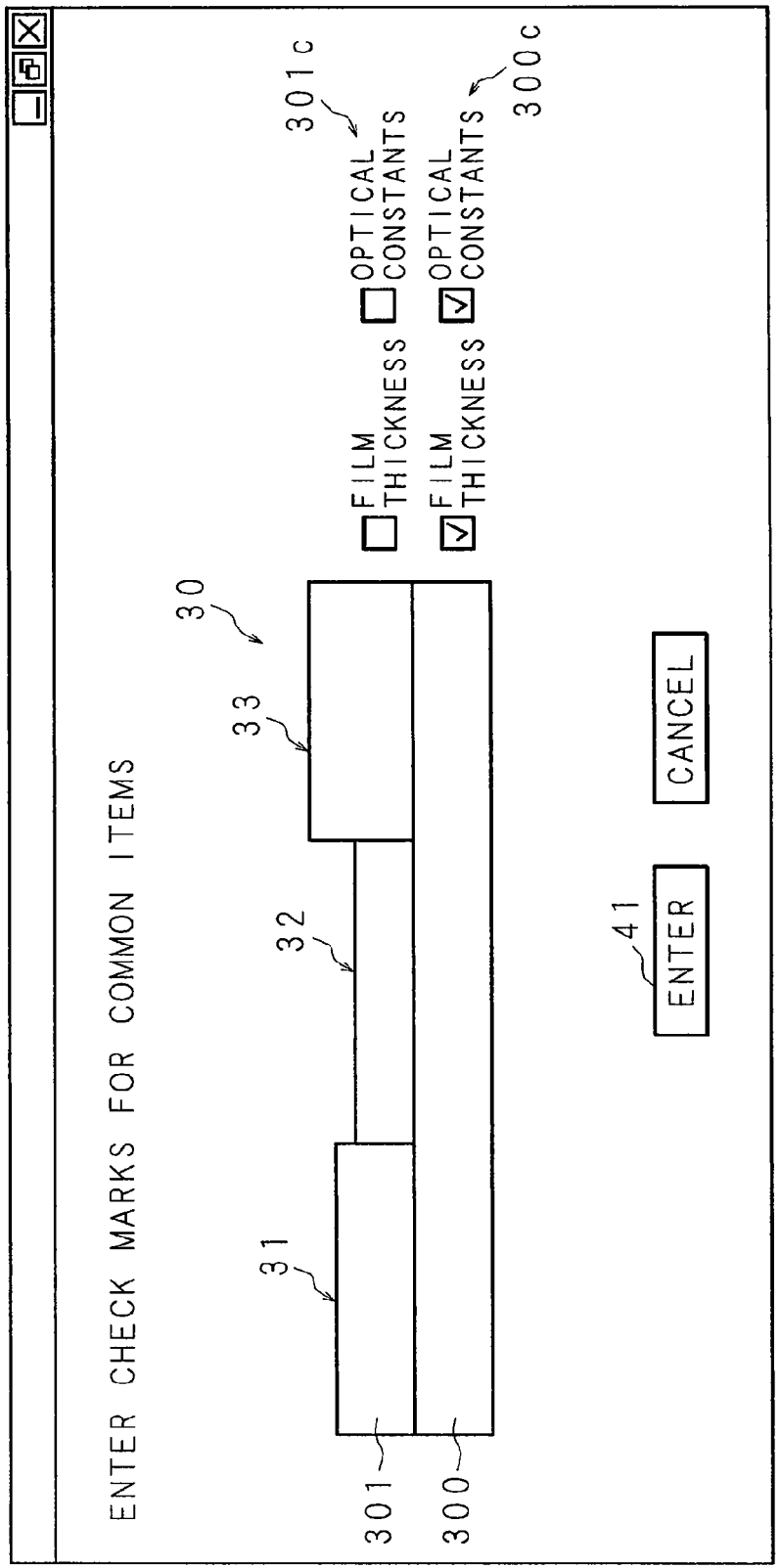

US 8,199,336 B2

OPTICAL MEASUREMENT APPARATUS, SPECTROSCOPIC ELLIPSOMETER, RECORDING MEDIUM, AND MEASUREMENT METHOD

CROSS-REFERENCE TO RELATED APPLICATIONS

This application is based upon and claims the benefit of priority of the prior Japanese Patent Application No. 2008-287232, filed on Nov. 8, 2008, the entire contents of which are incorporated herein by reference.

FIELD

The present invention relates to: an optical measurement apparatus measuring a film thickness or an optical constant of a sample; a spectroscopic ellipsometer; a recording medium storing a program causing a computer provided in an optical measurement apparatus to perform operation; and a measurement method.

BACKGROUND

Spectroscopic ellipsometers are known for their capability to irradiate light onto a sample and then measure the polarization state of reflected light so as to calculate the film thickness and the optical constant of each layer. Especially in the case of film stacks composed of semiconductor or the like, such a spectroscopic ellipsometer is used for irradiating light and thereby calculating the film thickness and the optical constant (see, for example, Japanese Patent Application Laid-Open No. 2004-286468).

Nevertheless, conventional measuring apparatuses including that described in Japanese Patent Application Laid-Open No. 2004-286468 have a problem that a large amount of time and effort are necessary in the measurement for such characterization. Further, in the apparatus described in Japanese Patent Application Laid-Open No. 2004-286468, complicated processing and condition setting are necessary to perform calculation of the film thickness and the optical constant of a multilayer film stack such as an ONO (Oxide Nitride Oxide). Thus, it is difficult to measure efficiently an ONO film stack distributed over a large area on a wafer.

SUMMARY

The present invention has been devised in view of such situations, and provides an optical measurement apparatus in which by using the characteristics of a sample where a plurality of stacks having a partly common structure are distributed, the film thickness or the optical constant of each layer is easily calculated over a target measurement area of the sample.

According to an aspect of the embodiments, an optical measurement apparatus includes:

a storage processing part storing into a storage part a plurality of main reference positions where measurement is to be performed and at least one movement value relative to each main reference position;

a main measuring part moving a measurement position to one of the main reference positions stored in the storage part, then irradiating light, and then measuring a change in a state of reflected light;

an auxiliary measuring part moving the measurement position to an auxiliary reference position based on the movement value relative to one of the main reference positions stored in the storage part, then irradiating light, and then measuring a change in a state of reflected light;

a main calculating part performing analysis on the basis of a main model corresponding to the main reference position stored in the storage part and the change in the state of light measured by the main measuring part, and calculating a film thickness or an optical constant; and an auxiliary calculating part performing analysis on the basis of an auxiliary model corresponding to the auxiliary reference position stored in the storage part and the change in the state of light measured by the auxiliary measuring part, and calculating a film thickness or an optical constant.

According to the above-mentioned aspect of the optical measurement apparatus, analysis is performed on the basis of the main model corresponding to the main reference position and the measured change in the state of light, so that the film thickness or the optical constant concerning the main reference position is calculated. Further, analysis is performed on the basis of the auxiliary model corresponding to the auxiliary reference position stored in the storage part and the measured change in the state of light, so that the film thickness or the optical constant concerning the auxiliary reference position is calculated. This permits easy calculation of the film thickness or the optical constant in each stack of the sample where a plurality of stacks having a partly common structure to each other are distributed. As a result, merely when the sample is placed once, the position and the characteristics of each stack having abnormality are recognized over a measurement target area of the sample.

The object and advantages of the invention will be realized and attained by the elements and combinations particularly pointed out in the claims. It is to be understood that both the foregoing general description and the following detailed description are exemplary and explanatory and are not restrictive of the embodiment, as claimed.

BRIEF DESCRIPTION OF DRAWINGS

FIG. 4A is a plan view of another sample and FIG. 4B is an enlarged view of a part of FIG. 4A

FIG. 6 is an explanation diagram illustrating a record layout of a coordinate value file.

FIG. 7 is an explanation diagram illustrating a conceptual image of a relevant information input screen.

FIG. 8 is an explanation diagram illustrating a record layout of a result DB.

FIG. 14 is an explanation diagram illustrating a record layout of a coordinate value file according to Embodiment 2.

FIG. 16 is an explanation diagram illustrating a record layout of a result DB according to Embodiment 2.

FIGS. 19A and 19B are flow charts illustrating a procedure of measurement processing according to Embodiment 2.

FIGS. 21A to 21C are flow charts illustrating a procedure of abnormality detection processing according to Embodiment 2.

FIG. 23 is an explanation diagram illustrating a conceptual image of a relevant information input screen according to Embodiment 3.

FIGS. 24A to 24C are flow charts illustrating a procedure of fitting processing according to Embodiment 3.

FIG. 25 is a schematic cross section of a sample according to Embodiment 4.

FIG. 27 is an explanation diagram illustrating a record layout of a coordinate value file according to Embodiment 4.

FIG. 28 is an explanation diagram illustrating a conceptual image of a relevant information input screen according to Embodiment 4.

| DESCRIPTION OF EMBODIMENTS | |
|---|---|
| 1 | Spectroscopic ellipsometer |
| 1A | Portable recording medium |
| 2 | Xenon lamp |
| 3 | Light irradiator |
| 4 | Stage |
| 5 | Light obtainer |
| 6 | Rail |
| 7 | Spectrometer |
| 8 | Data acquisition device |
| 9 | Motor controller |
| 10 | Computer |
| 11 | CPU |
| 13 | Input part |
| 14 | Display part |
| 15 | Storage part |
| 30 | Set |
| 31 | First stack |
| 32 | Second stack |
| 33 | Third stack |

-continued

| DESCRIPTION OF EMBODIMENTS | |
|---|---|
| 50 | Sample |
| 51 | Substrate |
| 151 | Coordinate value file |
| 152 | Result DB |
| 153 | Model file |
| 154 | Relevant file |
| 300 | Common film |
| 301 | First film |
| 302 | Second film |
| 303 | Third film |
| M1 to M6 | First motor to sixth motor |

DESCRIPTION OF EMBODIMENTS

Figure 1:
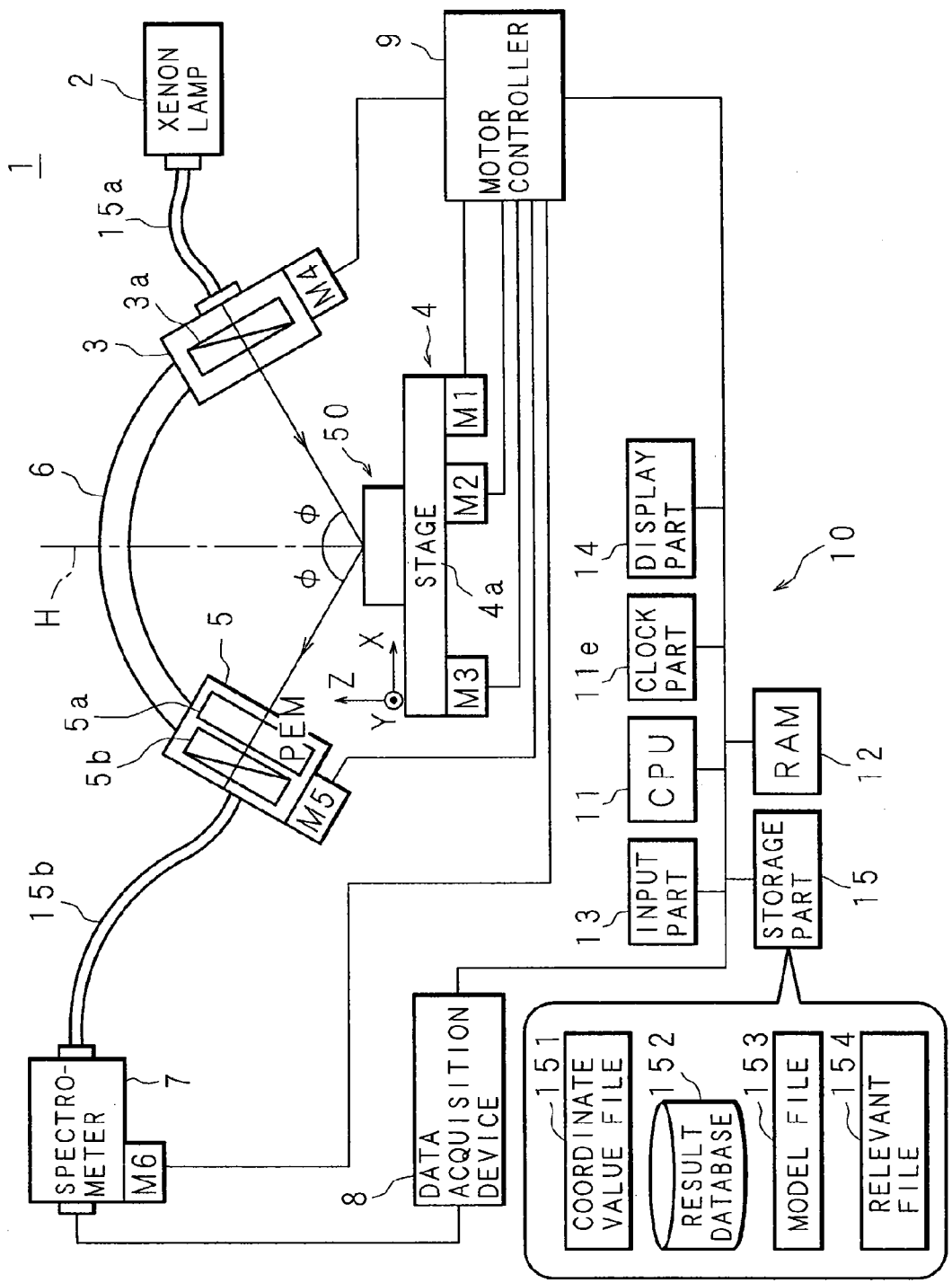
FIG. 1 is a block diagram illustrating a hardware configuration of an optical measurement apparatus.

FIG. 1 is a block diagram illustrating a hardware configuration of an optical measurement apparatus. The optical measurement apparatus 1 measuring a change in the state of light is, for example, a spectroscopic ellipsometer, a polarimeter, an interferometer, or an apparatus constructed from a combination of these. The following description is given for an example that the optical measurement apparatus 1 is a spectroscopic ellipsometer 1. The spectroscopic ellipsometer 1 is constructed from a xenon lamp 2, a light irradiator 3, a stage 4, a light obtainer 5, a spectrometer 7, a data acquisition device 8, a motor controller 9, a computer 10, and the like. The spectroscopic ellipsometer 1 measures a sample 50 in which individual sets each composed of a plurality of regularly arranged stacks having common layers in part are distributed.

Figure 2B:
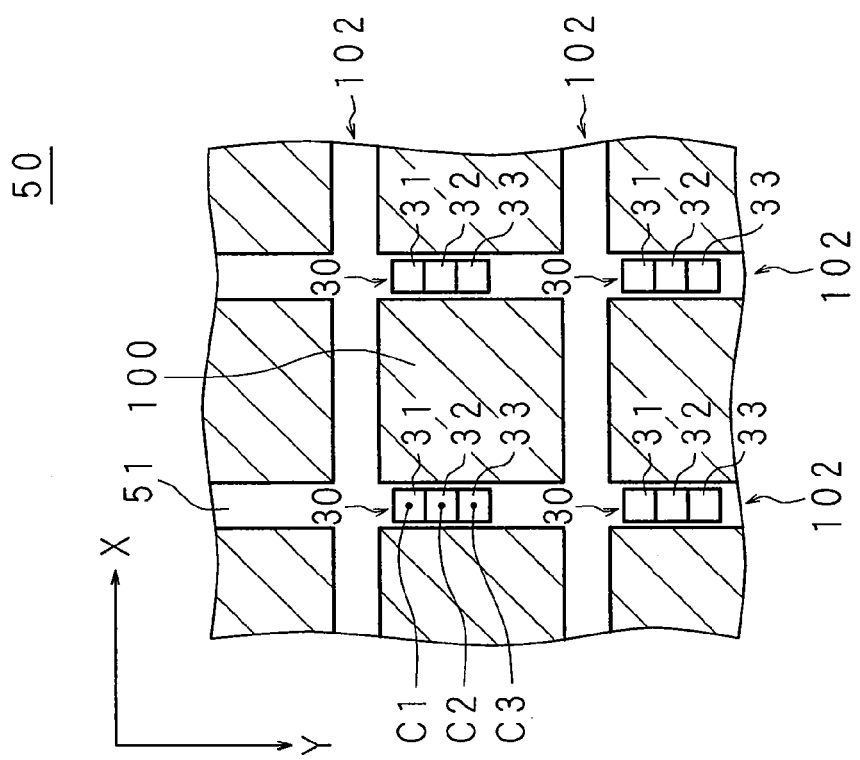
FIG. 2A is a plan view of a sample and FIG. 2B is an enlarged view of a part of FIG. 2A.

The spectroscopic ellipsometer 1 irradiates polarized light onto the sample 50 formed by stacking a plurality of films, then acquires light reflected by the sample 50, and measures the polarization state of the reflected light. Then, on the basis of the measurement result and a model corresponding to the sample 50, the spectroscopic ellipsometer 1 analyzes the characteristics of each film layer of the sample 50. FIG. 2 is a plan view of the sample 50. FIG. 3 is a schematic cross section of the sample 50. The sample 50 contains a substrate 51 and sets 30, 30, 30, . . . . For example, the sample 50 is composed of an ONO film. For example, the substrate 51 is a silicon wafer and a common film 300 is stacked on the substrate 51. For example, the common film 300 is a silicon dioxide film. A second film 302 is stacked on an approximately center part of the common film 300, while a third film 303 is stacked on an edge part of the common film 300 adjusted to the second film 302.

For example, the second film 302 and the third film 303 are silicon nitride films. Further, a fourth film 304 is stacked on the third film 303. For example, the fourth film 304 is a silicon dioxide film. A first stack 31 to a third stack 33 have a step shape as illustrated in FIG. 3. The present embodiment is described for an exemplary case that silicon dioxide films and silicon nitride films are employed. However, this example is merely illustrative, and employable materials are not limited to these. Further, although three layers are employed in the present description, the number of layers is not limited to this in actual implementation. Furthermore, although a Si substrate is employed for the ONO film in the present description, an SOI substrate for a TFT (Thin Film Transistor) device or the like, a transparent substrate such as a plastic plate or film, and a flexible metal substrate may similarly be employed. Further, in addition to the semiconductor field, the present technique may similarly be applied to the FPD (Flat Panel Display) field. The first stack 31 is formed from the common film 300. The second stack 32 is formed from the common film 300 and the second film 302. The third stack 33 is formed from the common film 300, the third film 303, and the fourth film 304. The present embodiment is described for an exemplary case that an ONO film is employed. However, this example is merely illustrative, and employable materials are not limited to this. Further, in the description of the present embodiment, the first stack 31, the second stack 32, and the third stack 33 link are connected to each other. However, actual implementation is not limited to this. That is, the first stack 31, the second stack 32, and the third stack 33 may be formed separately from each other with given spacing on the substrate 51. This point is common to the other embodiments described later. In this case, three films are stacked separately on the substrate 51. These are a first common film 300, a second common film 300, and a third common film 300. Then, the first common film 300 serves as the first stack 31. A second film 302 is formed on the second common film 300 so that the second stack 32 is obtained. Further, a third film 303 is formed on the third common film 300, and then a fourth film 304 is formed on the third film 303 so that the third stack 33 is obtained.

Figure 2A:
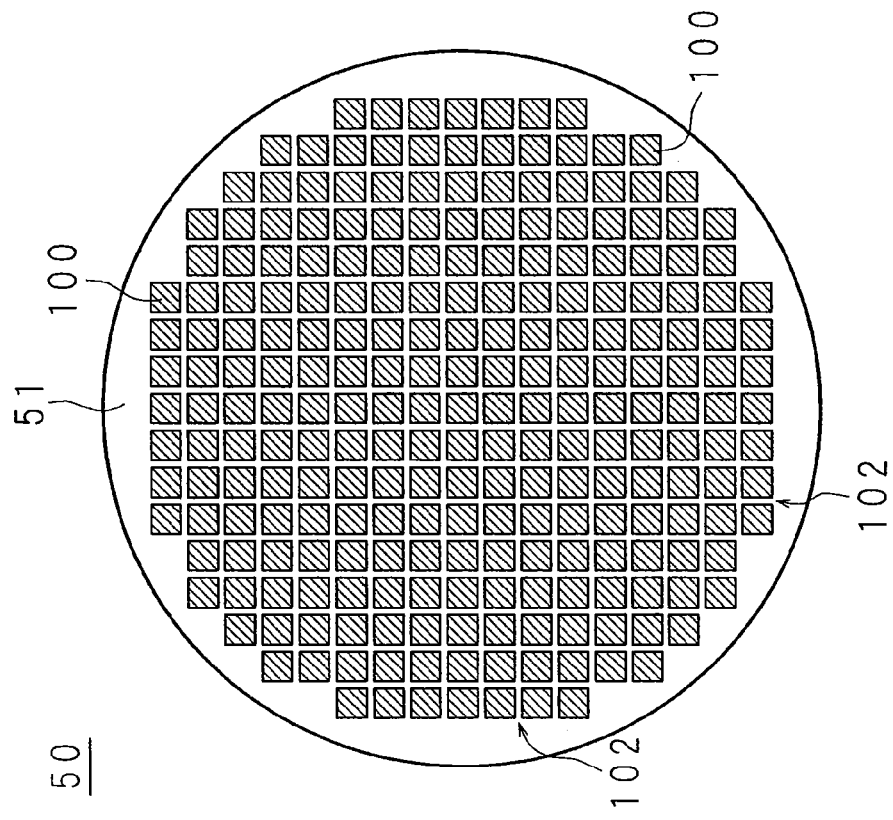
Figure 3:
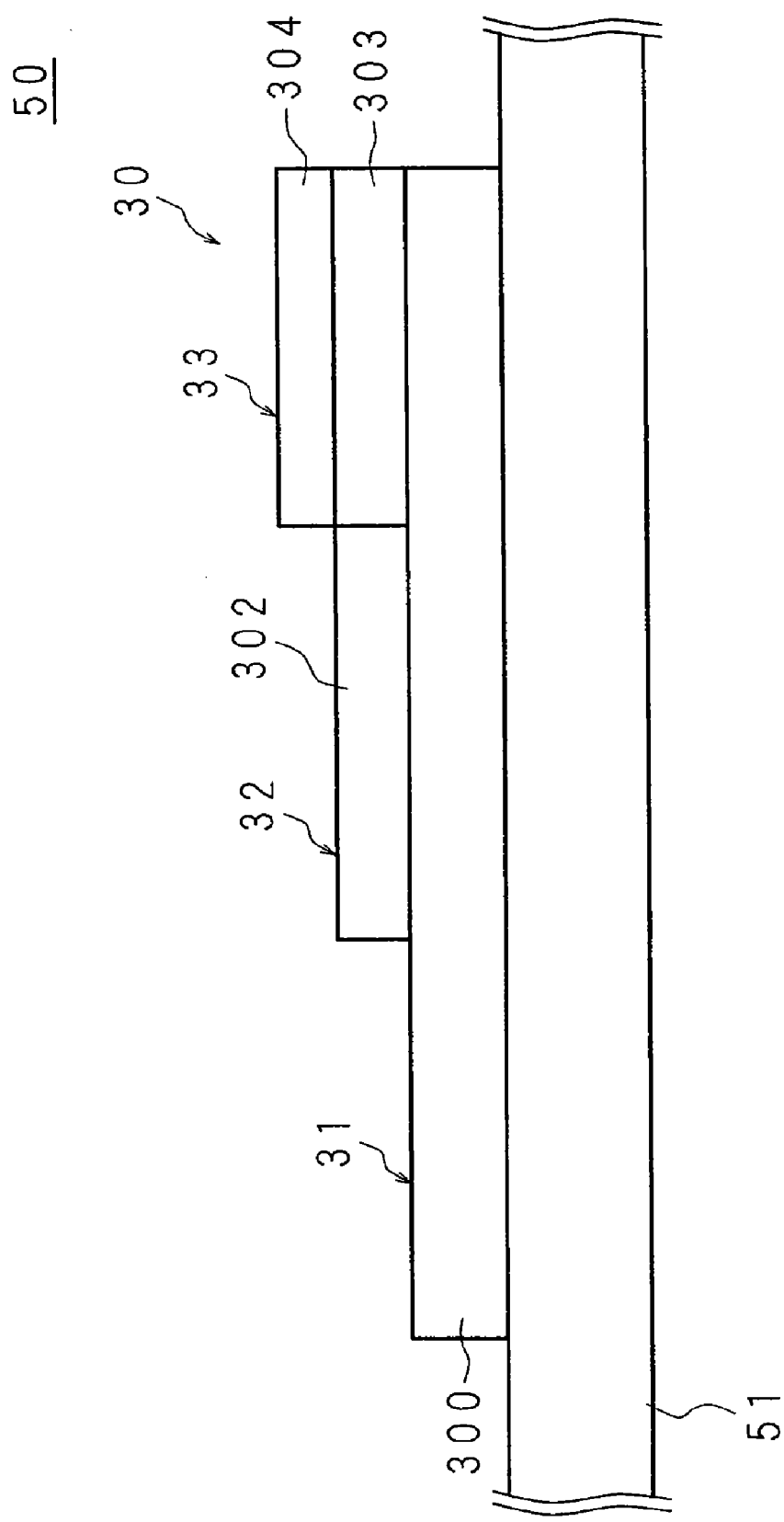
FIG. 3 is a schematic cross section of a sample.

FIG. 2A is a plan view of the entire sample 50. FIG. 2B is an enlarged plan view of a part of FIG. 2A. On the substrate 51, a plurality of approximately square-shaped chips 100, 100, 100, . . . are provided in a grid arrangement. Given spacing is formed by a scribe line 102 between a chip 100 and another chip 100. In the following description, an upper left point in the plan view of the substrate 51 in FIG. 2B is adopted as the origin having coordinates (0, 0). Then, the rightward direction from the origin is adopted as the positive X-direction, while the downward direction from the origin is adopted as the positive Y-direction. The sets 30, 30, 30, . . . are distributed regularly at given coordinate positions on each scribe line 102. The present embodiment is described for an exemplary case that such sets 30 and 30 are formed respectively on the scribe lines 102 and 102 on the right and left of the chip 100. When measurement is to be performed on the first stack 31, the measurement is performed around first (main) reference coordinates adopted as a first reference position C1. When measurement is to be performed on the second stack 32, the measurement is performed around auxiliary reference coordinates adopted as an auxiliary reference position C2. Similar, when measurement is to be performed on the third stack 33, the measurement is performed around auxiliary reference coordinates adopted as an auxiliary reference position C3. Here, in the present embodiment, the measurement point has been set up approximately at the center of each of the first stack 31 to the third stack 33. However, this setting is merely illustrative, and actual implementation is not limited to this. The first reference coordinates adopted as the formation position of the first stack 31 are stored in advance. Further, each set 30 may be arranged not on the scribe line 102 but on a test pattern. FIG. 4 is a plan view of a sample 50 according to another layout. FIG. 4A is a plan view of the entirety of the sample 50. FIG. 4B is an enlarged plan view of a part of FIG. 4A. A plurality of test patterns 101, 101, . . . are provided in the outer periphery of the substrate 51. Thus, the set 30 may be formed on each test pattern 101.

Returning to FIG. 1, the hardware configuration of the spectroscopic ellipsometer 1 is described below. The spectroscopic ellipsometer 1 analyzing the first stack 31 to the third stack 33 of the sample 50 having the structure described above is divided roughly into a measurement and analysis part and a drive part. The former part includes a measuring apparatus composed of a pair of the light irradiator 3 and the light obtainer 5. In the measurement and analysis part of the spectroscopic ellipsometer 1, the xenon lamp 2 and the light irradiator 3 are connected to each other through a first optical fiber cable 15a. The spectroscopic ellipsometer 1 irradiates polarized light onto the sample 50 placed on the stage 4, and then acquires reflected light from the sample 50 by means of the light obtainer 5. The light obtainer 5 is connected to the spectrometer 7 through a second optical fiber cable 15b. The spectrometer 7 performs measurement for each wavelength, and then transmits the measurement result in the form of an analog signal to the data acquisition device 8. The data acquisition device 8 converts the analog signal into a necessary value, and then transmits the data to the computer 10. The computer 10 performs analysis.

Further, in the drive part of the spectroscopic ellipsometer 1, a first motor M1 to a sixth motor M6 are provided in the stage 4, the light irradiator 3, the light obtainer 5, and the spectrometer 7. The driving of the first motor M1 to the sixth motor M6 is controlled by the motor controller 9 connected to the computer 10, so that the stage 4, the light irradiator 3, the light obtainer 5, and the spectrometer 7 are controlled into appropriate positions and orientations in accordance with the measurement. On the basis of instructions outputted from the computer 10, the motor controller 9 controls the driving of the first motor M1 to the sixth motor M6.

Next, the above-mentioned components of the spectroscopic ellipsometer 1 are individually described below in detail. First, the xenon lamp 2 is a light source, and generates white light containing a plurality of wavelength components. The generated white light is transferred to the light irradiator 3 through the first optical fiber cable 15a. The light irradiator 3 is arranged on a half circular arc rail 6, and has a polarizer 3a in the inside. Thus, the white light is polarized by the polarizer 3a, and then the polarization light is irradiated onto the sample 50. Further, the light irradiator 3 moves along the rail 6 when the fourth motor M4 is driven. This permits adjustment of the angle (incident angle φ) of the irradiated light relative to the perpendicular line H to the stage surface 4a of the stage 4.

The stage 4 is arranged in a slidable manner on a movement rail portion (not illustrated). Then, when the first motor M1 to the third motor M3 are driven, the stage 4 moves respectively in the X-direction, the Y-direction (a direction perpendicular to the page of FIG. 1), and the Z-direction serving as the height direction in FIG. 1. The movement of the stage 4 permits desired setting of the position of light incidence onto the sample 50, and hence surface analysis of the sample 50 is achieved. Here, the present embodiment is described for an exemplary case that the stage 4 is moved in the X-direction and the Y-direction. However, actual implementation is not limited to this. For example, the stage 4 may be fixed. Then, the light irradiator 3 and the light obtainer 5 may be moved so that the irradiation position may be moved in the X-direction and the Y-direction. Further, the stage surface 4a of the stage 4 on which the sample 50 is placed is black-colored in order to avoid reflection of light.

The light obtainer 5 acquires the light reflected by the sample 50, and then measures the polarization state of the acquired light. The light obtainer 5 is arranged on the rail 6 similarly to the light irradiator 3, and includes a PEM (Photo Elastic Modulator) 5a and an analyzer 5b. Then, the light reflected by the sample 50 is guided to the analyzer 5b through the PEM 5a. The light obtainer 5 is allowed to move along the rail 6 by the driving of the fifth motor M5. The light obtainer 5 is controlled in linkage with the movement of the light irradiator 3 by the motor controller 9 such that the reflection angle φ becomes equal to the incident angle φ. Here, the PEM 5a provided in the light obtainer 5 performs phase modulation on the acquired light at a necessary frequency (for example, 50 kHz), so that elliptically polarized light is obtained from the linearly polarized light. Further, the analyzer 5b acquires and measures a polarized light component selectively from the various polarized light components obtained by the phase modulation in the PEM 5a.

The spectrometer 7 includes a reflection mirror, a diffraction grating, a photo multiplier (PMT: Photo Multiplier Tube), and a control unit. In the spectrometer 7, the light transferred from the light obtainer 5 through the second optical fiber cable 15b is reflected by the reflection mirror and guided onto the diffraction grating. The angle of the diffraction grating is adjusted by the sixth motor M6, so that the wavelength of the emitted light is adjusted. The light advanced to the inside of the spectrometer 7 is amplified by the PMT so that the measurement signal (light) is stabilized even in the case of a low light intensity. Further, the control unit generates an analog signal corresponding to the measurement wavelength, and then transmits the signal to the data acquisition device 8.

On the basis of the signal from the spectrometer 7, the data acquisition device 8 calculates the amplitude ratio $\Psi$ and the phase difference $\Delta$ of the polarization states (p-polarization and s-polarization) of the reflected light for each wavelength, and then transmits the calculated results to the computer 10. Here, the amplitude ratio $\Psi$ and the phase difference $\Delta$ satisfy the relation of the following equation (1) for the complex reflection coefficient Rp of p-polarization and the complex reflection coefficient Rs of s-polarization.

$$Rp/Rs = \tan \Psi \cdot \exp(i \cdot \Delta) \quad (1)$$

Here, i denotes the imaginary unit (throughout this specification). Further, Rp/Rs is referred to as the polarization change amount $\rho$.

The computer 10 analyzes the sample 50 on the basis of the amplitude ratio $\Psi$ and the phase difference $\Delta$ of the polarization states obtained by the data acquisition device 8 and on the basis of a model corresponding to the sample. The computer 10 further controls the movement of the stage 4 and the like. The computer 10 includes a CPU (Central Processing Unit) 11, a display part 14, an input part 13, a storage part 15, a clock part 11e, and a RAM (Random Access Memory) 12. The CPU 11 is connected to the individual hardware parts of the computer 10 through a bus, and controls these parts. The CPU 11 further executes various kinds of software-based functions in accordance with various kinds of programs stored in the storage part 15.

The RAM 12 is a semiconductor device or the like, and writes and reads necessary information in accordance with instructions from the CPU 11. The display part 14 is a liquid crystal display unit, an organic electroluminescence display unit, or the like. The input part 13 is constructed from a keyboard, a mouse, and the like. The input part 13 may be a touch panel stacked on the display part 14. The clock part 11e outputs date and time information to the CPU 11. The storage part 15 is constructed from a hard disk, a large-capacity memory, or the like, and stores, in advance, various kinds of programs like computer programs for analysis and computer programs for movement control for the stage 4. The storage part 15 further stores: data of various kinds of menu images to be displayed on the display part 14; known data concerning the sample 50; a plurality of models; a plurality of dispersion equations used for generating models; generated models; reference data corresponding to various kinds of samples; reference values used in comparison processing concerning interference patterns; and the like.

In addition, the storage part 15 stores a coordinate value file 151, a result database (DB, hereinafter) 152, a model file 153, a relevant file 154, and the like. Here, these files and DB may be stored in a DB server or the like not illustrated. In the analysis of the sample 50, the computer 10 analyzes the refractive indices and the extinction coefficients (collectively referred to as optical constants, in some cases hereinafter) as the optical characteristics of: the common film 300 constituting the first stack 31; the common film 300 and the second film 302 constituting the second stack 32; and the common film 300, the third film 303, and the fourth film 304 constituting the third stack 33. The computer 10 analyzes also the film thicknesses and the like of these layers. With reference to the coordinate value file 151, the CPU 11 successively moves the stage and performs measurement of the first stack 31 to the third stack 33.

Figure 5:
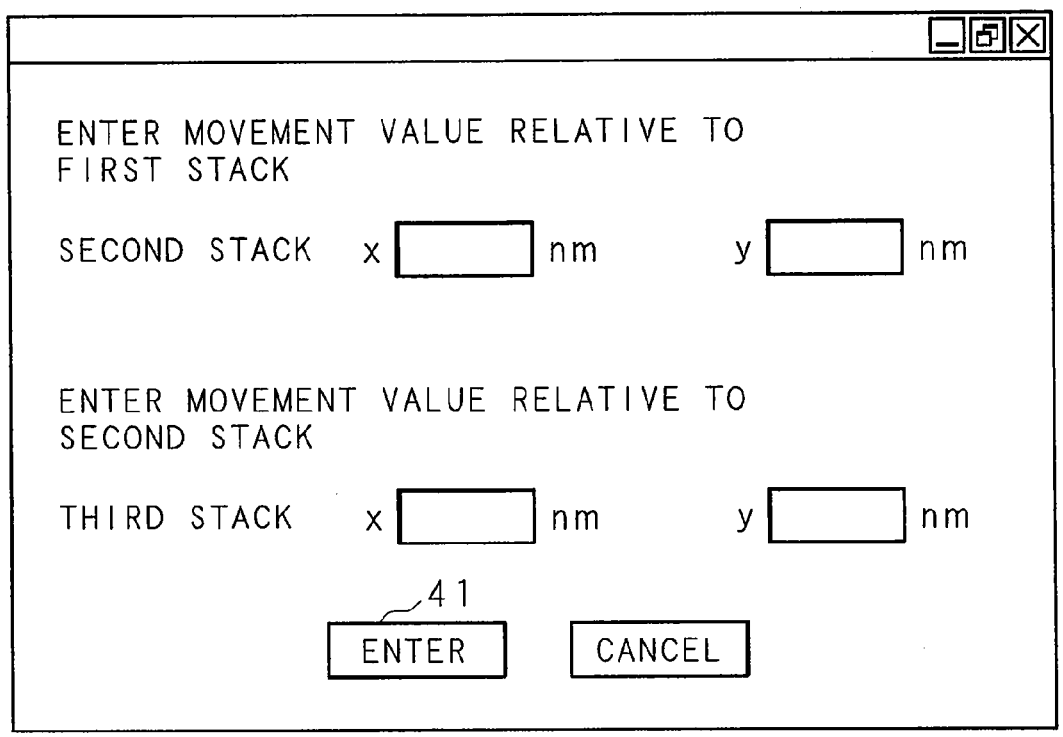
FIG. 5 is an explanation diagram illustrating a conceptual image of a movement value input screen.

FIG. 5 is an explanation diagram illustrating a conceptual image of a movement value input screen. The CPU 11 reads from the storage part 15 the movement value input screen image illustrated in FIG. 5, and then outputs the image onto the display part 14. Through the input part 13, the user inputs a movement value relative to the first stack 31 as the movement value for the second stack 32. Further, through the input part 13, the user inputs a movement value relative to the second stack 32 as the movement value for the third stack 33. Here, a movement value relative to the first stack 31 may be inputted as the movement value for the third stack 33. When the movement values in the X-direction and the Y-direction are inputted through the input part 13 and then the determination button 41 is operated, the CPU 11 receives the inputted movement values for the second stack 32 and the third stack 33. Here, the present embodiment is described for an exemplary case that each is inputted by the unit of nm. However, the movement value may be inputted by another unit such as μm.

The CPU 11 reads the coordinate step number per unit length stored in the storage part 15, and then multiply the coordinate step number by the movement values (length) so as to obtain movement coordinate step numbers for each of the second stack 32 and the third stack 33. Then, the CPU 11 adds to the first reference coordinates the calculated movement coordinate step numbers for the second stack 32, so as to obtain the second reference coordinates. Further, the CPU 11 adds to the second reference coordinates the movement coordinate step numbers for the third stack 33, so as to obtain the third reference coordinates. The CPU 11 stores into the coordinate value file 151 the second reference coordinates and the third reference coordinates have been calculated.

FIG. 6 is an explanation diagram illustrating a record layout of a coordinate value file 151. The coordinate value file 151 stores for each set 30 the first reference coordinates of the first stack 31, the auxiliary reference coordinates of the second stack 32 (referred to as the second reference coordinates, hereinafter), and the auxiliary reference coordinates of the third stack 33 (referred to as the third reference coordinates, hereinafter). The coordinate value file 151 has a set ID field, a first reference coordinate field, a second reference coordinate field, and a third reference coordinate field. Each set ID field stores a unique ID for identifying one of the sets 30, 30, 30, . . . . Each first reference coordinate field stores coordinate values where measurement on the first stack 31 is to be performed. Here, the present embodiment is described for an exemplary case that coordinate values are stored. However, distances may be stored that are uniquely converted from the coordinate values.

Each second reference coordinate field stores coordinate values where measurement on the second stack 32 is to be performed. Since the second film 302 is formed at a position deviated from the first stack 31 by a given distance, the movement value from the first reference coordinates adopted as the first reference position is inputted in advance through the input part 13. Further, the third reference coordinate field for the third stack is provided. The CPU 11 reads the coordinate step number per unit length stored in the storage part 15, and then calculates the movement coordinate step numbers. The CPU 11 adds the calculated movement coordinate step numbers to the first reference coordinates, so as to obtain the second reference coordinates. In the example of FIG. 6, the movement coordinate step numbers are (Sx, Ty). Thus, the second reference coordinates for the set ID 01 become (x1+Sx, y1+Ty). Further, the movement coordinate step numbers of the third stack 33 relative to the second stack 32 are (Ux, Vy). Thus, the third reference coordinates for the set ID 01 become (x1+Sx+Ux, y1+Ty+Vy). Here, the movement values may be concerning any one or both of the X-direction and the Y-direction. With reference to the coordinate value file 151, the CPU 11 controls the movement of the stage, then performs measurement on the first stack 31 at the first reference coordinates, and then performs measurement on the second stack 32 at the second reference coordinates. Similarly, measurement is performed on the third stack 33 at the third reference coordinates.

The relevant file 154 stores relevant information indicating whether the film thickness or the optical constants of each layer constituting the first stack 31 to the third stack 33 are common to or correlated to each other. With reference to the relevant information input screen through the input part 13, the user inputs relevant information. FIG. 7 is an explanation diagram illustrating a conceptual image of a relevant information input screen. Models for the first stack 31 to the third stack 33 are stored in advance in the model file 153. With reference to the first (main) model to the third model stored in the model file 153, the CPU 11 generates a relevant information input screen image, and then outputs the image onto the display part 14. The first model corresponds to the first stack 31, and is constructed from the common film 300. The second model corresponds to the second stack 32, and is constructed from the common film 300 and the second film 302 stacked thereon. The third model corresponds to the third stack 33, and is constructed from the common film 300, the third film 303, and the fourth film 304 stacked thereon. The present embodiment is described for an exemplary case that the film thickness and the optical constants of the common film 300 are common in the parameters in the first model to the third model. Further, obviously, the film thickness or the optical constants of the second film 302 of the second model and the third film 303 of the third model which are stacked on the common film 300 may be set common.

The CPU 11 displays check boxes 300c for lower layer and check boxes 301c for upper layer used for inputting relevant information corresponding to each layer. The user clicks (sets) layers and common parameters through the input part 13. In the present embodiment, both of the film thickness and the optical constants are assumed to be common parameters. However, any one of these may solely be a common parameter. When a common film thickness serving as the initial value of the common film 300 and dispersion equation parameters corresponding to the optical constants are inputted through the input part 13, the CPU 11 stores these information pieces into the storage part 15. In the example of FIG. 7, the film thickness and the optical constants of the common film 300 are common parameters as indicated by the corresponding check boxes 300c. When receiving an input of the determination button 41, the CPU 11 stores into the relevant file 154 the relevant information received through the input part 13, that is, the layer and the common parameters. In the process of analysis (referred to as fitting, hereinafter), the CPU 11 performs fitting with taking such relevant information into consideration, that is, with the condition that the film thickness and the optical constants of the common film 300 are common in the first stack 31 to the third stack 33.

On the basis of the measured amplitude ratio Ψ and phase difference Δ, when the complex refractive index of ambient around the substrate 51 and the sample 50 is known, the CPU 11 of the computer 10 uses a modeling program stored in advance in the storage part 15. Then, models corresponding to the items of the sample 50 set up by the user and the material structure of the sample 50 are generated and then stored into the model file 153. In the present embodiment, a first model for the first stack 31 corresponding to the first reference position, an auxiliary model for the second stack 32 corresponding to the auxiliary reference position (referred to as a second model, hereinafter), and an auxiliary model for the third stack 33 corresponding to the auxiliary reference position (referred to as a third model, hereinafter) are stored in the model file 153. By using the first model stored in the analysis stage, the CPU 11 calculates the film thickness and the complex refractive index of the common film 300 of the first stack 31. Similarly, by using the second model, the CPU 11 calculates the film thicknesses and the complex refractive indices of the common film 300 and the second film 302 of the second stack 32. Further, by using the third model, the CPU 11 calculates the film thicknesses and the complex refractive indices of the common film 300, the third film 303, and the fourth film 304 of the third stack 33.

With the refractive index n and the extinction coefficient k of a film layer to be analyzed, the complex refractive index N satisfies the relation expressed by the following optical equation (2).

$$N = n - ik \quad (2)$$

Further, when the incident angle is $\phi$ and the wavelength of light irradiated by the light irradiator 3 is $\lambda$, the amplitude ratio Ψ and the phase difference Δ measured by the ellipsometer outputted from the data acquisition device 8 satisfy the relation of the following equation (3) with the film thickness d, the refractive index n, and the extinction coefficient k each of the second film 302, the third film 303, the fourth film 304, and the common film 300 to be analyzed.

$$(d, n, k) = F(\rho) = F(\Psi(\lambda, \phi), \Delta(\lambda, \phi)) \quad (3)$$

By using the film thickness of each layer to be analyzed and a dispersion equation expressing the wavelength dependence of the complex dielectric constant and having a plurality of parameters, the CPU 11 of the computer 10 performs the processing (fitting) of changing the film thickness, the dispersion equation parameters, and the like such as to minimize the difference between the model spectra ($\Psi_M(\lambda_i)$, $\Delta_M(\lambda_i)$) (polarization state) obtained from the stored model by theoretical calculation and the measured spectra ($\Psi_E(\lambda_i)$, $\Delta_E(\lambda_i)$) (polarization state) representing the measurement result outputted from the data acquisition device 8. An example of an employable dispersion equation is given in the following equation (4). This dispersion equation is merely illustrative, and actual implementation is not limited to this.

$$\varepsilon = \varepsilon_\infty + \frac{(\varepsilon_s - \varepsilon_\infty)\varpi_t^2}{\varpi_t^2 - \varpi^2 + i\Gamma_0\varpi} + \frac{\varpi_p^2}{-\varpi^2 + i\Gamma_D\varpi} + \sum_{j=1}^{2} \frac{f_j\varpi_{oj}^2}{\varpi_{oj}^2 - \varpi^2 + i\gamma_j\varpi} \quad (4)$$

In equation (4), $\in$ in the left-hand part denotes the complex dielectric constant, while $\in_\infty$ represents the dielectric constant at high frequencies (the high frequency dielectric constant), and $\in_s$ represents the dielectric constant at low frequencies (the static dielectric constant). $\omega_{oj}$, $\omega_t$, and $\omega_p$ represent the oscillator, transverse and plasma frequency respectively. $\Gamma_0$, $\Gamma_D$, and $\gamma_j$ are the damping factors. $f_i$ represents the oscillator strength parameter. $f_j = (\in_{sj} - \in_\infty)$ holds. Further, the complex dielectric constant $\in$ (corresponding to $\in(\lambda)$) and the complex refractive index N (corresponding to $N(\lambda)$) satisfy the following equation (5).

$$\in(\lambda) = N^2(\lambda) \quad (5)$$

The procedure of fitting is described below. When the sample 50 is measured, T measurement data pairs are denoted by Exp (i=1, 2, . . . , T) and the calculated data pairs from T models are denoted by Mod (i=1, 2, . . . , T). Further, the measurement error is assumed to have a normal distribution with a standard deviation $\sigma_i$. Then, the mean square error $\chi^2$ according to the least square method is obtained by the following equation (6). Here, P indicates the number of parameters. A smaller value of mean square error $\chi^2$ indicates better agreement between the measurement result and the generated model. Thus, when a plurality of models are compared, a model having the smallest value of mean square error $\chi^2$ corresponds to the best model.

$$\chi^2 = [1/(2T-P)]\sum_{i=1}^{T}(\text{Exp}_i - \text{Mod}_i)^2/\sigma_i^2 \quad (6)$$

The above-mentioned series of processing concerning the sample analysis performed by the CPU 11 of the computer 10 is set forth in a computer program for analysis stored in the storage part 15. In the spectroscopic ellipsometer 1 according to the present embodiment, a plurality of model types (model structures) for the sample 50 generated in advance are stored in the model file 153 in the storage part 15. On the basis of the processing set forth in the computer program (modeling program) stored in the storage part 15, these model type structures are read and used for analysis.

The above-mentioned fitting based on a model is executed on each of the first stack 31 to the third stack 33. In the process of fitting, the CPU 11 performs fitting with taking the above-mentioned relevant information into consideration, that is, with the condition that the film thickness and the optical constants of the common film 300 are common in the first stack 31 to the third stack 33. As a result, the CPU 11 obtains the film thickness and the dispersion equation parameters of the common film 300 of the first stack 31. Similarly, the CPU 11 calculates the film thickness and the dispersion equation parameters of each of the common film 300 and the second film 302 of the second stack 32. Further, the CPU 11 calculates the film thickness and the dispersion equation parameters of each of the common film 300, the third film 303, and the fourth film 304 of the third stack 33. Here, since the condition that the film thickness and the dispersion equation parameters of the common film 300 are the same is adopted, the film thickness of the common film 300 becomes the same in the first stack 31 to the third stack 33. Further, similarly to the film thickness, the refractive index and the extinction coefficient of the common film 300 obtained from the film thickness and the dispersion equation parameters are common in the first stack 31 to the third stack 33. With reference to the dispersion equation parameters and the like of the common film 300 of the first stack 31, the CPU 11 calculates the optical constants (the refractive index n, the extinction coefficient k) of the common film 300. Similarly, with reference to the dispersion equation parameters and the like of each of the common film 300 and the second film 302 of the second stack 32, the CPU 11 calculates the optical constants (the refractive index n and the extinction coefficient k) of each of the common film 300 and the second film 302. Further, with reference to the dispersion equation parameters and the like of each of the common film 300, the third film 303, and the fourth film 304 of the third stack 33, the CPU 11 calculates the optical constants (the refractive index n and the extinction coefficient k) of all the films: common film 300, the third film 303, and the fourth film 304.

The CPU 11 stores into the result DB 152 the film thicknesses, the optical constants, and the like obtained by the fitting. FIG. 8 is an explanation diagram illustrating a record layout of the result DB 152. The result DB 152 has a set ID field, a film field, a measured spectra field, a film thickness field, abnormality flag fields for film thickness, refractive index, and extinction coefficient, a refractive index field, and an extinction coefficient field. The CPU 11 executes processing of storage, retrieval, and the like of necessary information in an interactive manner by using an access interface corresponding to a database format such as SQL (Structured Query Language) in a schema in which keys of the fields in the result DB 152 are related to each other.

The result DB 152 stores the measured spectra, the film thickness, the optical constants, and the like of each of the first stack 31 to the third stack 33. Here, the example of FIG. 8 illustrates the contents of storage for the second stack 32. The set ID field stores each set ID described above. The film field stores the name of each film in the stack. In the example of FIG. 8, the second film 302 serving as an upper layer and the common film 300 of the second stack 32 are stored. The measured spectra field stores the measured spectra ($\Psi_E(\lambda_i)$, $\Delta_E(\lambda_i)$) of each film of each set ID obtained by measurement.

The film thickness field stores the film thickness of each film of each set ID obtained by fitting between the model spectra ($\Psi_M(\lambda_i)$, $\Delta_M(\lambda_i)$) (abbreviated as $\Psi_M$ and $\Delta_M$, hereinafter) obtained by theoretical calculation based on the first model for the first stack 31, the second model for the second stack 32, or the third model for the third stack 33 and the measured spectra ($\Psi_E(\lambda_i)$, $\Delta_E(\lambda_i)$) (abbreviated as $\Psi_E$ and $\Delta_E$, hereinafter). The refractive index field and the extinction coefficient field respectively store the refractive index and the extinction coefficient of each film of each set ID calculated from the dispersion equation parameters obtained by fitting.

Each abnormality flag field stores a flag indicating abnormality when each of the film thickness and the optical constants of each film of each set ID falls outside a given range of reference film thickness or reference optical constant (reference refractive index or reference extinction coefficient) stored in advance. In the example of FIG. 8, each open circle indicates an abnormality flag. As seen from the figure, abnormality is present in the film thickness and the extinction coefficient of the second film 302 of the set ID 01. The reference film thickness and the given range are stored in advance in the storage part 15. As for the reference film thickness and the given range, appropriate values may be inputted through the input part 13 by the user, and then stored into the storage part 15. Each given range indicates an allowable error, and may be expressed, for example, as the reference film thickness±several nm. Alternatively, the range may be expressed as 99% to 101% (±1%) or the like of the reference film thickness.

Figure 9A:
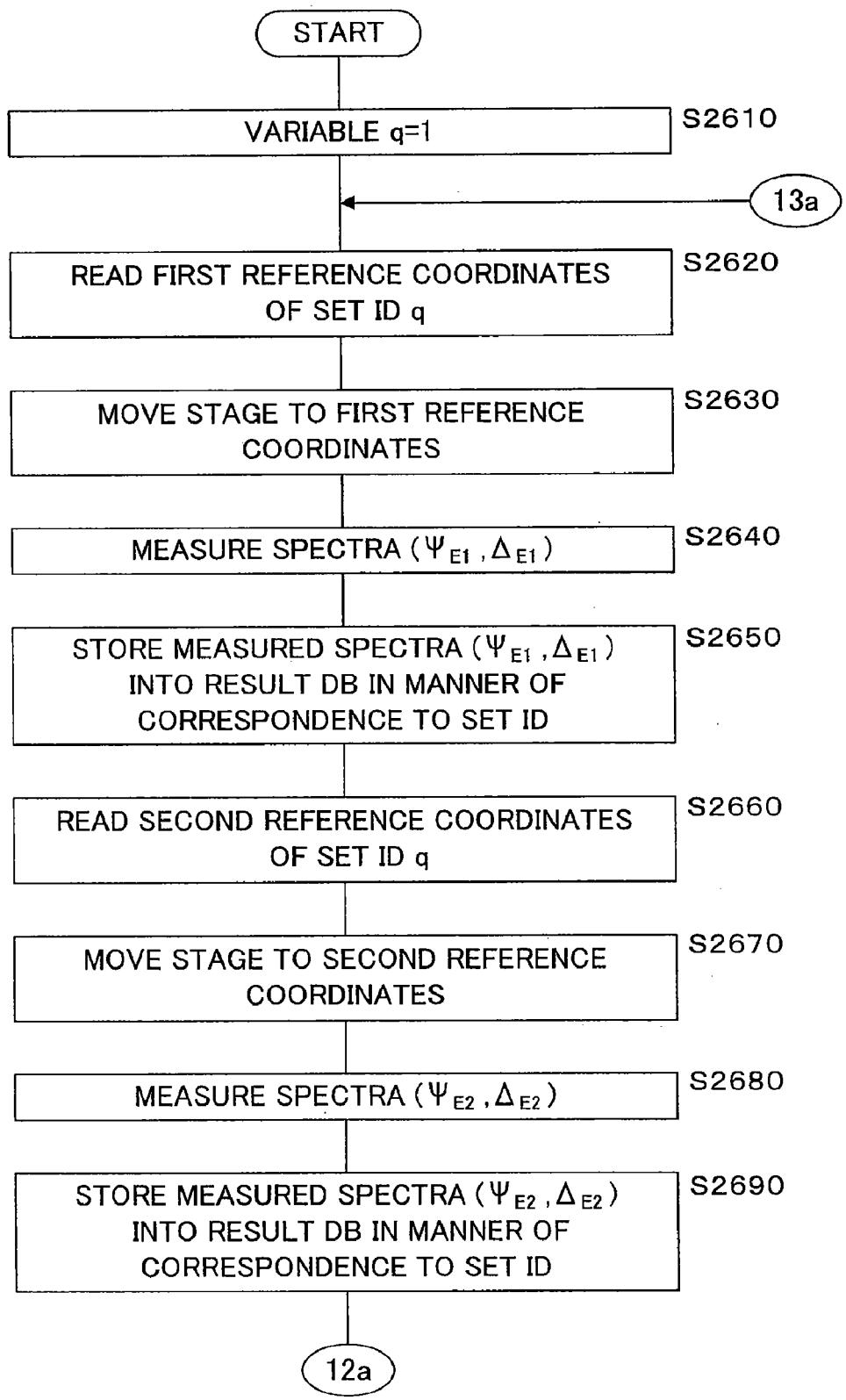
FIGS. 9A and 9B are flow charts illustrating a procedure of measurement processing.
Figure 9B:
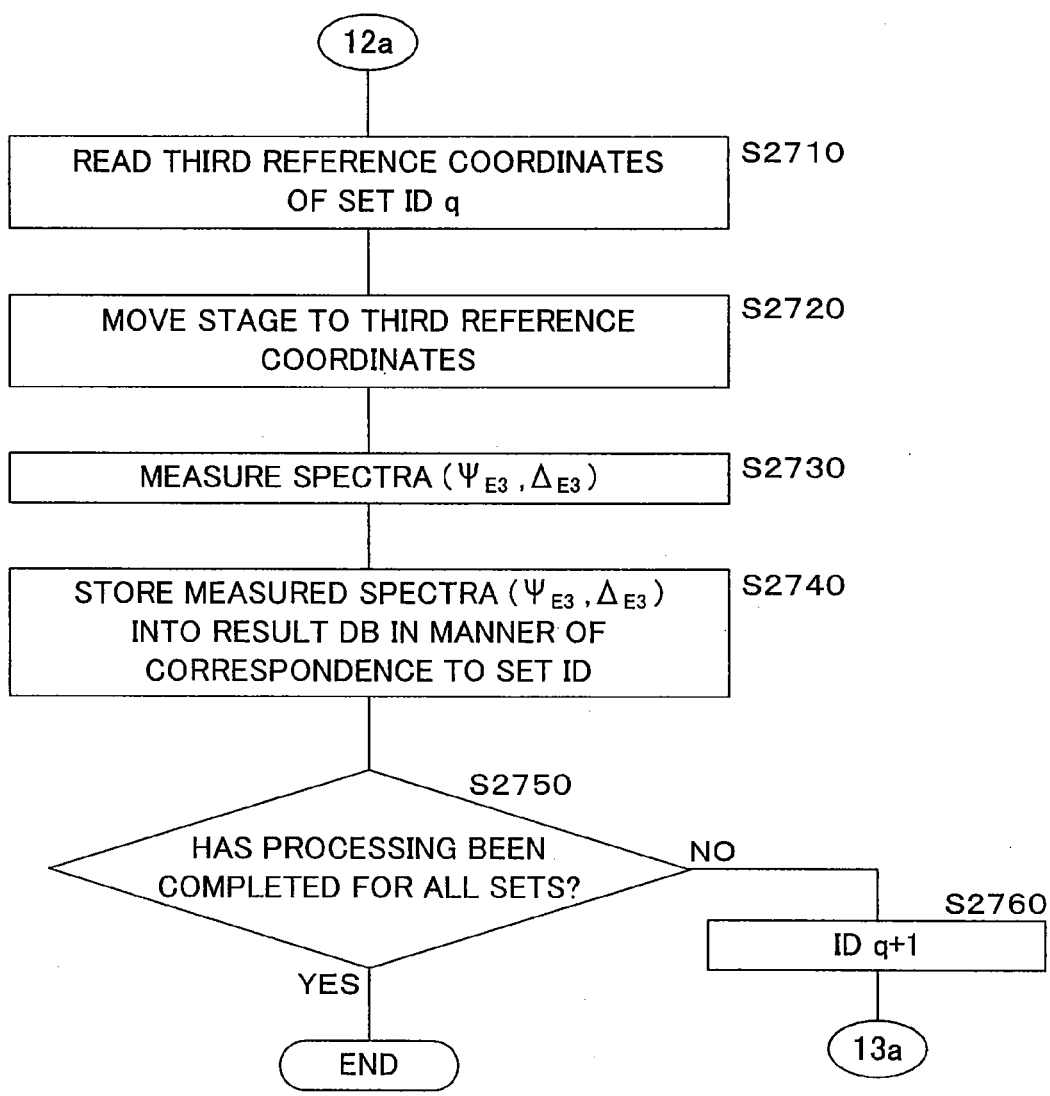
Figure 10A:
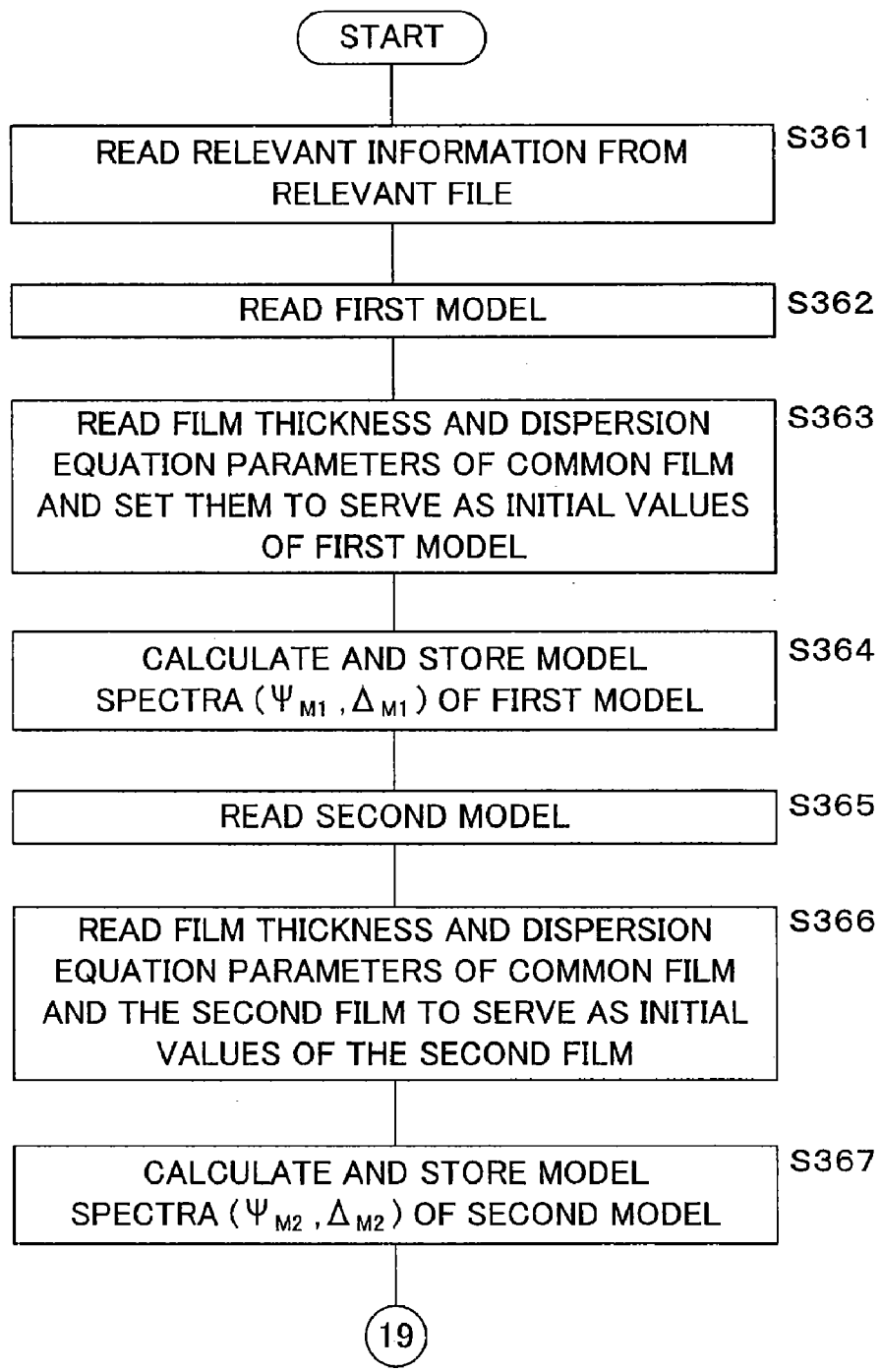
FIGS. 10A to 10C are flow charts illustrating a procedure of fitting processing.
Figure 10B:
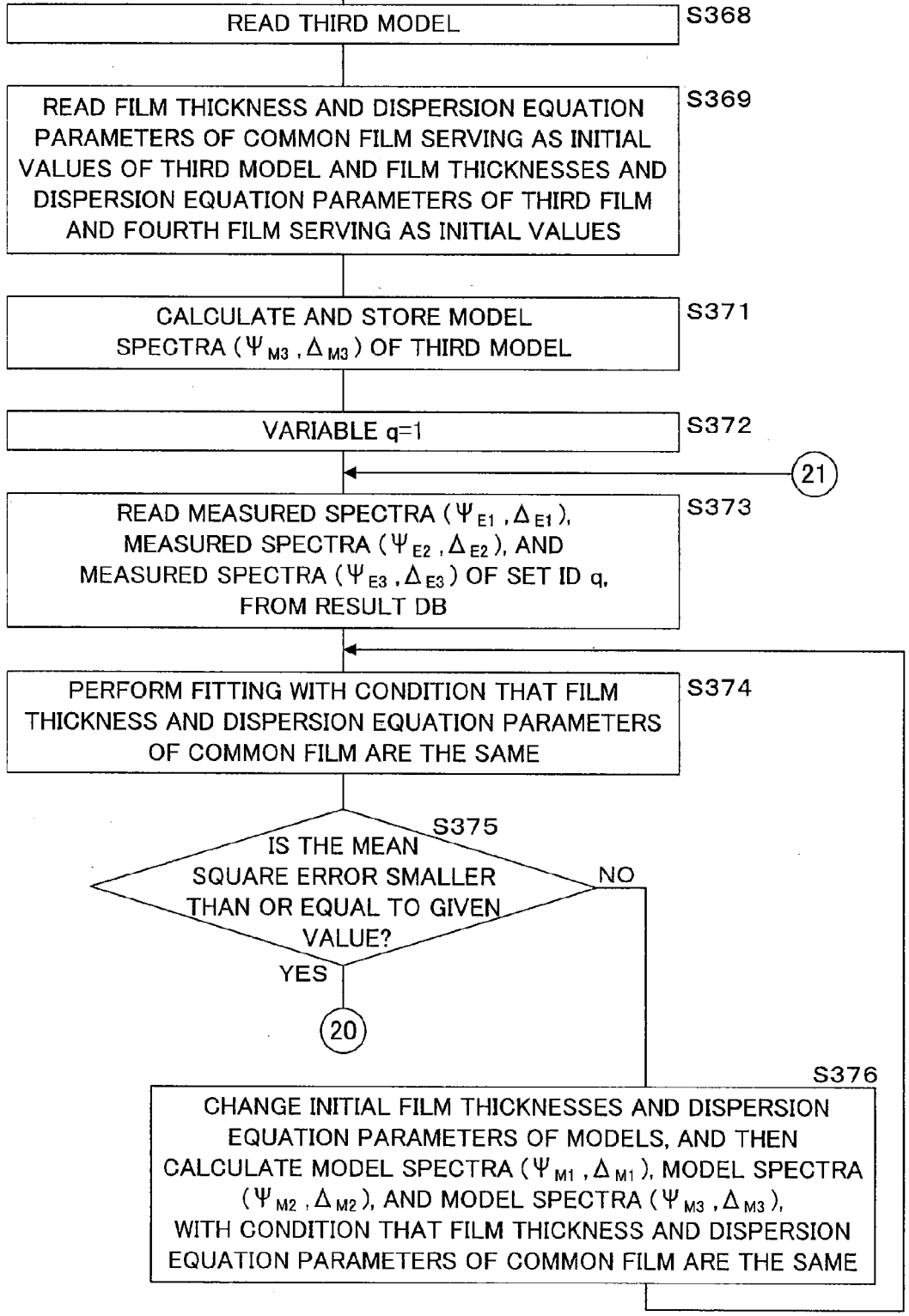
Figure 10C:
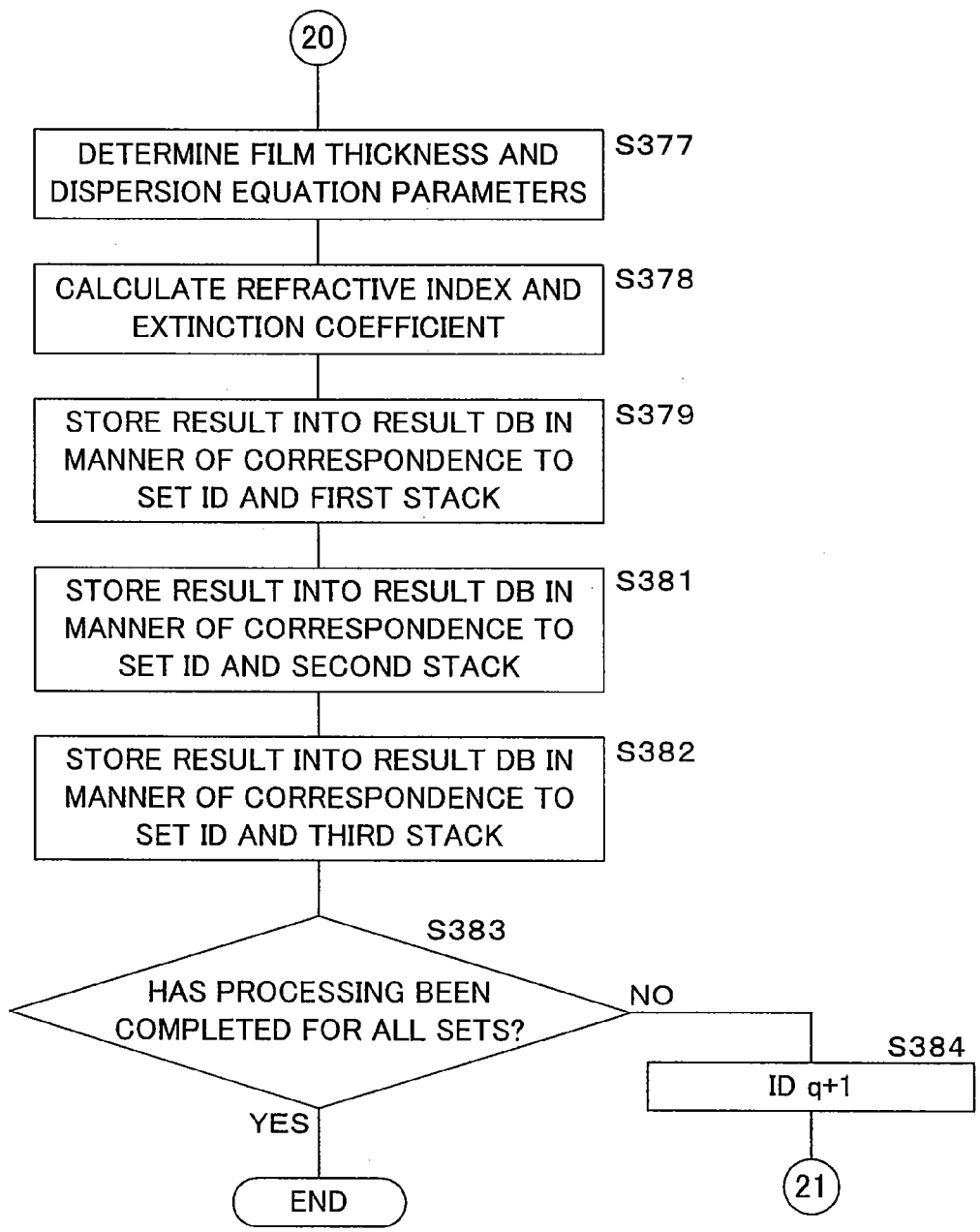

FIGS. 9A and 9B are flow charts illustrating a procedure of measurement processing. The CPU 11 substitutes 1 into the variable q (step S2610). The CPU 11 reads from the coordinate value file 151 the first reference coordinates of the set ID q (step S2620). When the variable q is 1, the first reference coordinates of the set ID "01" are read. The CPU 11 controls the first motor M1 and the second motor M2 through the motor controller 9 so as to move the stage to the first reference coordinates (step S2630). Then, measurement preparation for the first stack 31 is completed. Then, the CPU 11 of the spectroscopic ellipsometer 1 controls the light irradiator 3 and the light obtainer 5 so as to irradiate light onto the first stack 31, and then acquires a measured spectra ($\Psi_{E1}$, $\Delta_{E1}$) (step S2640). The CPU 11 receives the measured spectra ($\Psi_{E1}$, $\Delta_{E1}$) outputted from the data acquisition device 8, and then stores the data into the result DB 152 in a manner of correspondence to the set ID (step S2650).

The CPU 11 reads from the coordinate value file 151 the second reference coordinates of the set ID q (step S2660). The CPU 11 controls the first motor M1 and the second motor M2 through the motor controller 9 so as to move the stage to the second reference coordinates (step S2670). Then, measurement preparation for the second stack 32 is completed. Then, the CPU 11 of the spectroscopic ellipsometer 1 controls the light irradiator 3 and the light obtainer 5 so as to irradiate light onto the second stack 32, and then acquires a measured spectra ($\Psi_{E2}$, $\Delta_{E2}$) (step S2680).

The CPU 11 receives the measured spectra ($\Psi_{E2}$, $\Delta_{E2}$) outputted from the data acquisition device 8, and then stores the data into the result DB 152 in a manner of correspondence to the set ID (step S2690). The CPU 11 reads from the coordinate value file 151 the third reference coordinates of the set ID q (step S2710). The CPU 11 controls the first motor M1 and the second motor M2 through the motor controller 9 so as to move the stage to the third reference coordinates (step S2720). Then, measurement preparation for the third stack 33 is completed. Then, the CPU 11 of the spectroscopic ellipsometer 1 controls the light irradiator 3 and the light obtainer 5 so as to irradiate light onto the third stack 33, and then acquires a measured spectra ($\Psi_{E3}$, $\Delta_{E3}$) (step S2730).

The CPU 11 receives the measured spectra ($\Psi_{E3}$, $\Delta_{E3}$) outputted from the data acquisition device 8, and then stores the data into the result DB 152 in a manner of correspondence to the set ID (step S2740). The CPU 11 determines whether the processing has been completed for all sets 30 (step S2750). When it is determined that the processing is not yet completed for all sets 30 (NO at step S2750), the CPU 11 increments the variable q (step S2760). Then, the CPU 11 returns the procedure to step S2620, and then acquires the measured spectra of the next set 30. In contrast, when it is determined that the processing has been completed for all sets 30 (YES at step S2750), the CPU 11 terminates the series of processing.

FIGS. 11A to 11C are flow charts illustrating a procedure of fitting processing. The CPU 11 reads the relevant information stored in the relevant file 154 (step S361). The present embodiment is described for a case that the film thickness, the dispersion equation parameters, and the optical constants of the common film 300 are common. The CPU 11 reads from the model file 153 the first model stored in correspondence to the first stack 31 in advance in the storage part 15 (step S362). In accordance with the read-out first model, the CPU 11 reads from the storage part 15 the film thickness and the dispersion equation parameters of the common film 300 serving as the initial values of the first model stored in advance (step S363). On the basis of the first model, the initial film thickness, and the parameters having been read, the CPU 11 calculates the model spectra ($\Psi_{M1}$, $\Delta_{M1}$) of the first model, and then stores the result into the storage part 15 (step S364).

The CPU 11 reads from the model file 153 the second model stored in correspondence to the second stack 32 in advance in the storage part 15 (step S365). In accordance with the read-out second model, the CPU 11 reads from the storage part 15: the film thickness and the dispersion equation parameters of the common film 300 serving as the initial values of the second model stored in advance; and the film thickness and the dispersion equation parameters of the second film 302 serving as the initial values of the second model (step S366). On the basis of the second model, the initial film thickness, and the parameters having been read, the CPU 11 calculates the model spectra ($\Psi_{M2}$, $\Delta_{M2}$) of the second model, and then stores the result into the storage part 15 (step S367).

The CPU 11 reads from the model file 153 the third model stored in correspondence to the third stack 33 in advance in the storage part 15 (step S368). In accordance with the read-out third model, the CPU 11 reads from the storage part 15: the film thickness and the dispersion equation parameters of the common film 300 serving as the initial values of the third model stored in advance; and the film thickness and the dispersion equation parameters of the third film 303 and the fourth film 304 serving as the initial values of the third model (step S369). On the basis of the third model, the initial film thickness, and the parameters having been read, the CPU 11 calculates the model spectra ($\Psi_{M3}$, $\Delta_{M3}$) of the third model, and then stores the result into the storage part 15 (step S371).

The CPU 11 substitutes 1 into the variable q (step S372). Then, the CPU 11 reads from the result DB 152: the measured spectra ($\Psi_{E1}$, $\Delta_{E1}$) concerning the first stack 31 of the set ID q; the measured spectra ($\Psi_{E2}$, $\Delta_{E2}$) concerning the second stack 32; and the measured spectra ($\Psi_{E3}$, $\Delta_{E3}$) concerning the third stack 33 (step S373).

The CPU 11 performs the processing (fitting) of comparing with each other the measured spectra ($\Psi_{E1}$, $\Delta_{E1}$) corresponding to (concerning) the first stack 31, the model spectra ($\Psi_{M1}$, $\Delta_{M1}$) of the first model, the measured spectra ($\Psi_{E2}$, $\Delta_{E2}$) concerning the second stack 32, the model spectra ($\Psi_{M2}$, $\Delta_{M2}$) of the second model, the measured spectra ($\Psi_{E3}$, $\Delta_{E3}$) concerning the third stack 33, and the model spectra ($\Psi_{M3}$, $\Delta_{M3}$) of the third model, which have been read for the purpose of fitting, and then changing the film thicknesses, the dispersion equation parameters, and the like such as to minimize the difference between each measured spectra and modeled spectra with the condition that the film thickness and the dispersion equation parameters of the common film 300 are the same (step S374). As a result of the fitting, the CPU 11 obtains a mean square error $\chi^2$ according to the least square method. The mean square error $\chi^2$ at step S374 is calculated in accordance with equation (7).

$$\chi^2 = \frac{1}{2T_1 - P_1} \sum_{i=1}^{T_1} (\text{Exp}_i - \text{Mod}_i)^2 / \sigma_i^2 + \qquad (7)$$

$$\frac{1}{2T_2 - P_2} \sum_{i=1}^{T_2} (\text{Exp}_i - \text{Mod}_i)^2 / \sigma_i^2 +$$

-continued $$\frac{1}{2T_3 - P_3} \sum_{i=1}^{T_3} (\text{Exp}_i - \text{Mod}_i)^2 / \sigma_i^2$$

Here, when measurement is performed on the first stack 31, T1 measurement data pairs are Exp (i=1, 2, ..., T1) and the calculated data pairs of T1 models are Mod (i=1, 2, ..., T1). When measurement is performed on the second stack 32, T2 measurement data pairs are Exp (i=1, 2, ..., T2) and the calculated data pairs of T2 models are Mod (i=1, 2, ..., T2). When measurement is performed on the third stack 33, T3 measurement data pairs are Exp (i=1, 2, ..., T3) and the calculated data pairs of T3 models are Mod (i=1, 2, ..., T3). Further, P1 indicates the number of parameters in the measurement of the first stack 31, P2 indicates the number of parameters in the measurement of the second stack 32, and P3 indicates the number of parameters in the measurement of the third stack 33.

As a result of the fitting, the CPU 11 determines whether the calculated mean square error is smaller than or equal to a given value (step S375). This given value is stored in the storage part 15. When it is determined that the calculated mean square error is not smaller than or equal to the given value (NO at step S375), the CPU 11 goes to step S376. With the condition that the film thickness and the dispersion equation parameters of the common film 300 are the same, the CPU 11 appropriately changes the film thicknesses and the dispersion equation parameters having been set up as initial values of the models, and then re-calculates the model spectra set $\Psi_{M1}$ and $\Delta_{M1}$, the model spectra ($\Psi_{M2}$, $\Delta_{M2}$), and the model spectra ($\Psi_{M3}$, $\Delta_{M3}$) (step S376).

When it is determined that the calculated mean square error is smaller than or equal to the given value (YES at step S375), the CPU 11 determines the film thickness and the dispersion equation parameters of the first stack 31, the film thickness and the dispersion equation parameters of each layer of the second stack 32, and the film thickness and the dispersion equation parameters of each layer of the third stack 33 (step S377). Here, since the condition that the film thickness and the dispersion equation parameters of the common film 300 are the same is adopted, the film thickness of the common film 300 becomes the same in the first stack 31 to the third stack 33. Further, similarly to the film thickness, the refractive index and the extinction coefficient of the common film 300 obtained from the dispersion equation parameters are common in the first stack 31 to the third stack 33. With reference to the dispersion equation parameters and the like of the common film 300, the CPU 11 calculates the refractive index and the extinction coefficient of the common film 300 of the first stack 31, then with reference to the dispersion equation parameters and the like of the common film 300 and the second film 302, calculates the refractive indices and the extinction coefficients of the common film 300 and the second film 302 of the second stack 32, and then with reference to the dispersion equation parameters and the like of the common film 300, the third film 303, and the fourth film 304, calculates the refractive indices and the extinction coefficients of the common film 300, the third film 303, and the fourth film 304 of the third stack 33 (step S378).

The CPU 11 stores into the result DB 152 the film thickness, the refractive index, and the extinction coefficient of the common film 300 in a manner of correspondence to the set ID and the first stack 31 (step S379). Similarly, the CPU 11 stores into the result DB 152 the film thickness, the refractive index, and the extinction coefficient of each of the common film 300 and the second film 302 in a manner of correspondence to the set ID and the second stack 32 (step S381). The CPU 11 stores into the result DB 152 the film thickness, the refractive index, and the extinction coefficient of each of the common film 300, the third film 303, and the fourth film 304 in a manner of correspondence to the set ID and the third stack 33 (step S382).

The CPU 11 determines whether the processing has been completed for all sets 30 (step S383). When it is determined that the processing is not yet completed for all sets 30 (NO at step S383), the CPU 11 increments the variable q (step S384). The CPU 11 returns the procedure to step S373 so as to perform fitting on the next set 30. In contrast, when it is determined that the processing has been completed for all sets 30 (YES at step S383), the CPU 11 terminates the series of processing.

Embodiment 2

Figure 11:
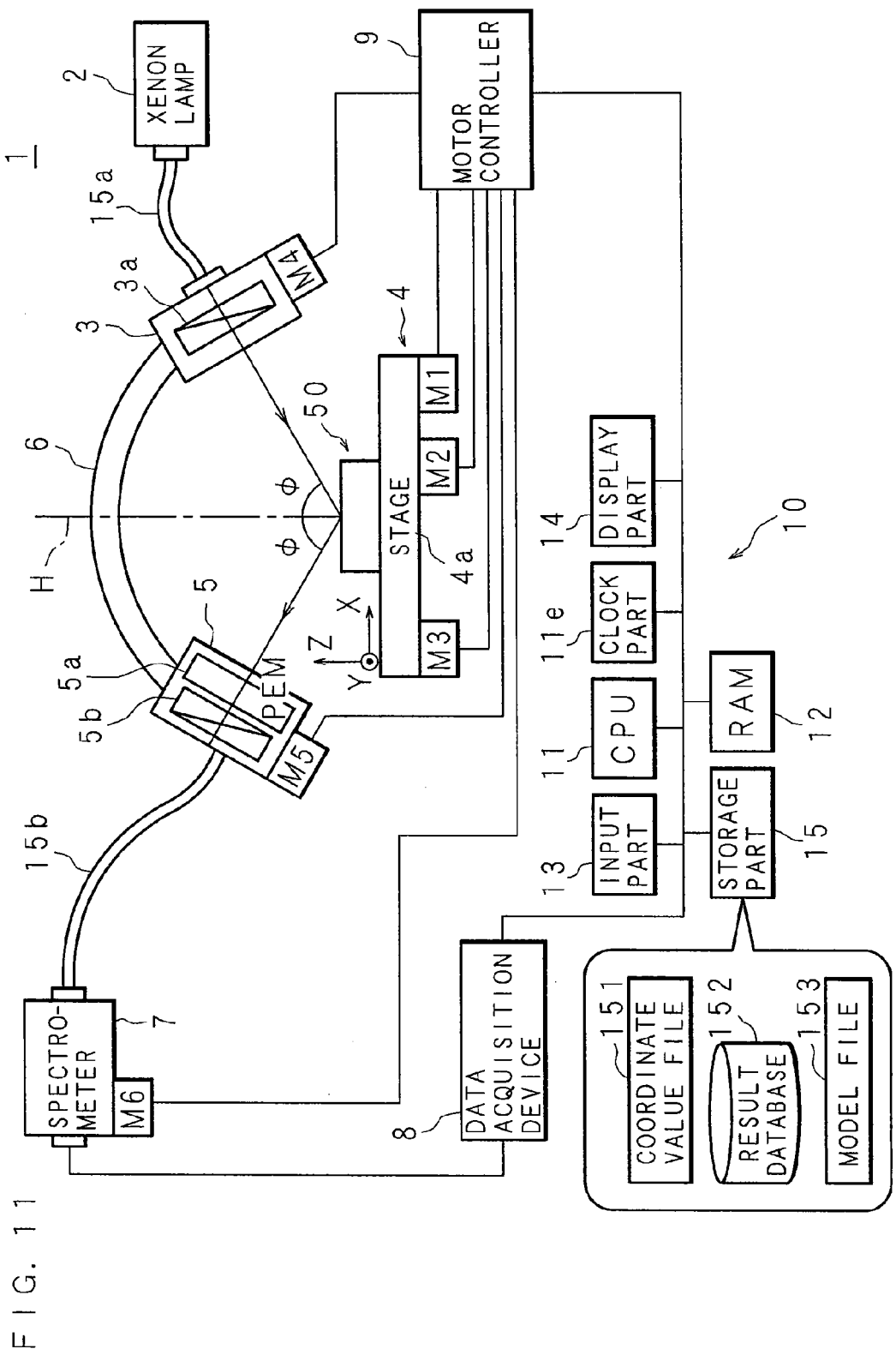
FIG. 11 is a block diagram illustrating a hardware configuration of an optical measurement apparatus according to Embodiment 2.

FIG. 11 is a block diagram illustrating a hardware configuration of an optical measurement apparatus according to Embodiment 2. The optical measurement apparatus 1 measuring a change in the state of light is, for example, a spectroscopic ellipsometer, a polarimeter, an interferometer, or an apparatus constructed from a combination of these. The following description is given for an example that the optical measurement apparatus 1 is a spectroscopic ellipsometer 1. The spectroscopic ellipsometer 1 is constructed from a xenon lamp 2, a light irradiator 3, a stage 4, a light obtainer 5, a spectrometer 7, a data acquisition device 8, a motor controller 9, a computer 10, and the like. The spectroscopic ellipsometer 1 measures a sample 50 in which individual sets each composed of a plurality of regularly arranged stacks having common layers in part are distributed.

Figure 12:
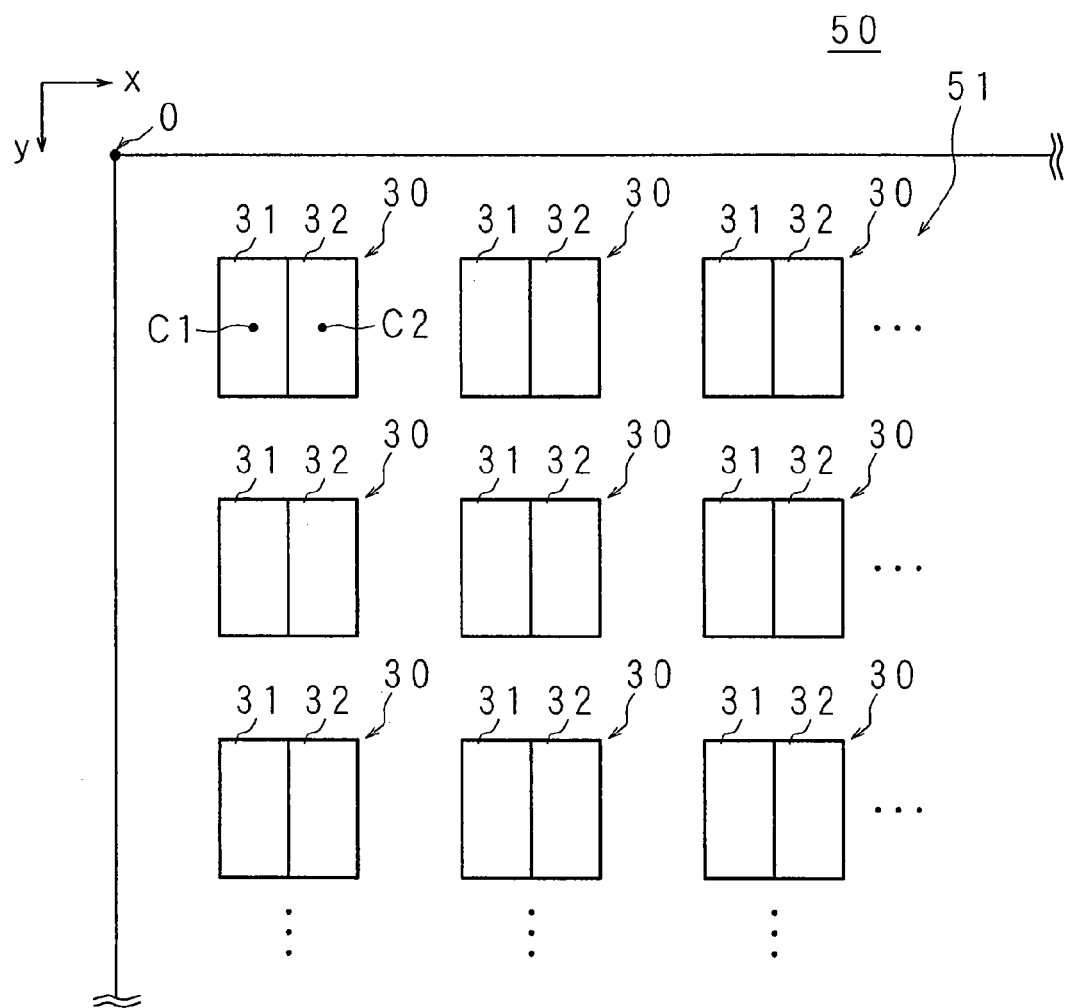
FIG. 12 is a plan view of a sample according to Embodiment 2.
Figure 13:
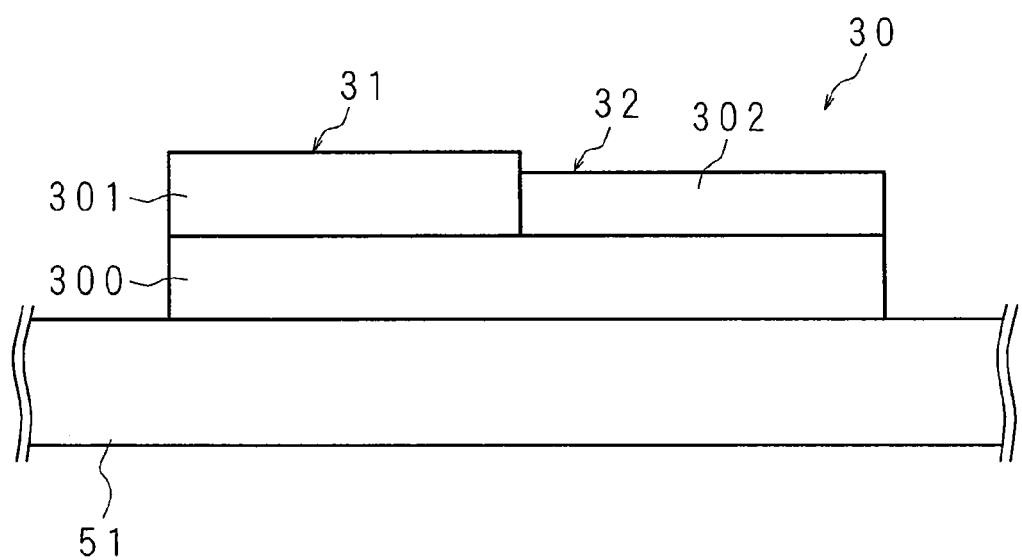
FIG. 13 is a schematic cross section of a sample according to Embodiment 2.

The spectroscopic ellipsometer 1 irradiates polarized light onto the sample 50 formed by depositing (stacking) a plurality of films, then acquires light reflected by the sample 50, and measures the polarization state of the reflected light. Then, on the basis of the measurement result and a model corresponding to the sample 50, the spectroscopic ellipsometer 1 analyzes the characteristics of each film layer of the sample 50. FIG. 12 is a plan view of the sample 50 according to Embodiment 2. FIG. 13 is a schematic cross section of the sample 50 according to Embodiment 2. The sample 50 contains a substrate 51 and sets 30, 30, 30, .... For example, the substrate 51 is a transparent substrate composed of glass, plastics, or the like, or alternatively, is a plastic plate or film, a flexible metal substrate, or a wafer. As illustrated in FIG. 13, on the substrate 51, a common film (referred to as a lower layer film) 300 is formed by CVD (Chemical Vapor Deposition), ALD (Atomic Layer Deposition), thermal oxidation, sputtering, or the like.

For example, the lower layer film 300 is a silicon oxide film (SiO2) formed on a wafer by CVD. A first film 301 is formed on one part of the upper surface of the lower layer film 300. For example, the first film 301 is an amorphous silicon film, and is formed on the lower layer film 300 by CVD or the like. On the other part of the upper surface of the lower layer film 300, a second film 302 is formed. The second film 302 is composed of a material different from that of the first film, and is a polysilicon film or the like formed on the lower layer film 300 by CVD or the like. In the following description, the stack obtained by stacking the first film 301 on the lower layer film 300 is referred to as a first stack 31, while the stack obtained by stacking the second film 302 on the lower layer film 300 is referred to as a second stack 32. Further, the combination of the first stack 31 and the second stack 32 is referred to as a set 30.

For simplicity of description, the present embodiment is described for an exemplary case that the lower layer film 300 common in the first stack 31 and the second stack 32 is composed of a single layer. However, actual implementation is not limited to this. That is, it is sufficient that the lower layer film 300 is common in the first stack 31 and the second stack 32, and hence the lower layer film 300 may be formed by stacking a plurality of films. Further, the lower layer film 300 may be replaced by a plurality of films that surround the upper side and the lower side of the first film 301 and the second film 302. Further, electrodes, a protective cover, or the like may be added (formed) to the first stack 31 and the second stack 32.

The first film 301 and the second film 302 are formed from mutually different substances whose film thicknesses or optical characteristics including each refractive index and each extinction coefficient are different from each other. The present embodiment is described for an exemplary case that the first film 301 and the second film 302 are formed from mutually different substances whose film thicknesses and optical constants are different from each other. As illustrated in FIG. 12, the sets 30 are distributed on the plane of the substrate 51 surface. In the following description, an upper left point in the plan view of the substrate 51 is adopted as the origin having coordinates (0, 0). Then, the rightward direction from the origin is adopted as the positive X-direction, while the downward direction from the origin is adopted as the positive Y-direction.

The first stacks 31 and the second stacks 32 constituting the sets 30 are formed and distributed at given coordinate positions in accordance with the circuit design. When measurement is to be performed on the first stack 31, the measurement is performed around the first reference coordinates adopted as the first reference position C1. When measurement is to be performed on the second stack 32, the measurement is performed around auxiliary reference coordinates adopted as an auxiliary reference position C2. Here, in the present embodiment, the measurement point has been set up approximately at the center of each of the first stack 31 and the second stack 32. However, this setting is merely illustrative, and actual implementation is not limited to this. The first reference coordinates adopted as the formation position of the first stack 31 are stored in advance.

Returning to FIG. 11, the hardware configuration of the spectroscopic ellipsometer 1 is described below. The spectroscopic ellipsometer 1 analyzing the first stack 31 and the second stack 32 of the sample 50 having the structure described above is divided roughly into a measurement and analysis part and a drive part. The former part includes a measuring apparatus composed of a pair of the light irradiator 3 and the light obtainer 5. In the measurement and analysis part of the spectroscopic ellipsometer 1, the xenon lamp 2 and the light irradiator 3 are connected to each other through a first optical fiber cable 15a. The spectroscopic ellipsometer 1 irradiates polarized light onto the sample 50 placed on the stage 4, and then acquires reflected light from the sample 50 by means of the light obtainer 5. The light obtainer 5 is connected to the spectrometer 7 through a second optical fiber cable 15b. The spectrometer 7 performs measurement for each wavelength, and then transmits the measurement result in the form of an analog signal to the data acquisition device 8. The data acquisition device 8 converts the analog signal into a necessary value, and then transmits the data to the computer 10. The computer 10 performs analysis.

Further, in the drive part of the spectroscopic ellipsometer 1, a first motor M1 to a sixth motor M6 are provided in the stage 4, the light irradiator 3, the light obtainer 5, and the spectrometer 7. The driving of the first motor M1 to the sixth motor M6 is controlled by the motor controller 9 connected to the computer 10, so that the stage 4, the light irradiator 3, the light obtainer 5, and the spectrometer 7 are controlled into appropriate positions and orientations in accordance with the measurement. On the basis of instructions outputted from the computer 10, the motor controller 9 controls the driving of the first motor M1 to the sixth motor M6.

Next, the above-mentioned components of the spectroscopic ellipsometer 1 are individually described below in detail. First, the xenon lamp 2 is a light source, and generates white light containing a plurality of wavelength components. The generated white light is transferred to the light irradiator 3 through the first optical fiber cable 15a. The light irradiator 3 is arranged on a half circular arc rail 6, and has a polarizer 3a in the inside. Thus, the white light is polarized by the polarizer 3a, and then the polarization light is irradiated onto the sample 50. Further, the light irradiator 3 moves along the rail 6 when the fourth motor M4 is driven. This permits adjustment of the angle (incident angle $\phi$)) of the irradiated light relative to the perpendicular line H to the stage surface 4a of the stage 4.

The stage 4 is arranged in a slidable manner on a movement rail portion (not illustrated). Then, when the first motor M1 to the third motor M3 are driven, the stage 4 moves respectively in the X-direction, the Y-direction (a direction perpendicular to the page of FIG. 11), the Z-direction serving as the height direction in FIG. 11. The movement of the stage 4 permits desired setting of the position of light incidence onto the sample 50, and hence surface analysis of the sample 50 is achieved. Here, the present embodiment is described for an exemplary case that the stage 4 is moved in the X-direction and the Y-direction. However, actual implementation is not limited to this. For example, the stage 4 may be fixed. Then, the light irradiator 3 and the light obtainer 5 may be moved so that the irradiation position may be moved in the X-direction and the Y-direction. Further, the stage surface 4a of the stage 4 on which the sample 50 is placed is black-colored in order to avoid reflection of light.

The light obtainer 5 acquires the light reflected by the sample 50, and then measures the polarization state of the acquired light. The light obtainer 5 is arranged on the rail 6 similarly to the light irradiator 3, and includes a PEM (Photo Elastic Modulator) 5a and an analyzer 5b. Then, the light reflected by the sample 50 is guided to the analyzer 5b through the PEM 5a. The light obtainer 5 is allowed to move along the rail 6 by the driving of the fifth motor M5. The light obtainer 5 is controlled in linkage with the movement of the light irradiator 3 by the motor controller 9 such that the reflection angle $\phi$ becomes equal to the incident angle $\phi$. Here, the PEM 5a provided in the light obtainer 5 performs phase modulation on the acquired light at a necessary frequency (for example, 50 kHz), so that elliptically polarized light is obtained from the linearly polarized light. Further, the analyzer 5b acquires and measures a polarized light component selectively from the various polarized light components obtained by the phase modulation in the PEM 5a.

The spectrometer 7 includes a reflection mirror, a diffraction grating, a photo multiplier (PMT: Photo Multiplier Tube), and a control unit. In the spectrometer 7, the light transferred from the light obtainer 5 through the second optical fiber cable 15b is reflected by the reflection mirror and guided onto the diffraction grating. The angle of the diffraction grating is adjusted by the sixth motor M6, so that the wavelength of the emitted light is adjusted. The light advanced to the inside of the spectrometer 7 is amplified by the PMT so that the measurement signal (light) is stabilized even in the case of a low light intensity. Further, the control unit generates an analog signal corresponding to the measurement wavelength, and then transmits the signal to the data acquisition device 8.

On the basis of the signal from the spectrometer 7, the data acquisition device 8 calculates the amplitude ratio Ψ and the phase difference Δ of the polarization states (p-polarization and s-polarization) of the reflected light for each wavelength, and then transmits the calculated results to the computer 10. Here, the amplitude ratio Ψ and the phase difference Δ satisfy the relation of the above-mentioned equation (1) for the complex reflection coefficient Rp of p-polarization and the complex reflection coefficient Rs of s-polarization.

The computer 10 analyzes the sample 50 on the basis of the amplitude ratio Ψ and the phase difference Δ of the polarization states obtained by the data acquisition device 8 and on the basis of a model corresponding to the sample. The computer 10 further controls the movement of the stage 4 and the like. The computer 10 includes a CPU (Central Processing Unit) 11, a display part 14, an input part 13, a storage part 15, a clock part 11e, and a RAM (Random Access Memory) 12. The CPU 11 is connected to the individual hardware parts of the computer 10 through a bus, and controls these parts. The CPU 11 further executes various kinds of software-based functions in accordance with various kinds of programs stored in the storage part 15.

The RAM 12 is a semiconductor device or the like, and writes and reads necessary information in accordance with instructions from the CPU 11. The display part 14 is a liquid crystal display unit, an organic electroluminescence display unit, or the like. The input part 13 is constructed from a keyboard, a mouse, and the like. The input part 13 may be a touch panel stacked on the display part 14. The clock part 11e outputs date and time information to the CPU 11. The storage part 15 is constructed from a hard disk, a large-capacity memory, or the like, and stores, in advance, various kinds of programs like computer programs for analysis and computer programs for movement control for the stage 4. The storage part 15 further stores: data of various kinds of menu images to be displayed on the display part 14; known data concerning the sample 50; a plurality of models; a plurality of dispersion equations used for generating models; generated models; reference data corresponding to various kinds of samples; reference values used in comparison processing concerning interference fringes; and the like.

In addition, the storage part 15 stores a coordinate value file 151, a result database (DB, hereinafter) 152, a model file 153, and the like. Here, these files and DB may be stored in a DB server or the like not illustrated. In the process of analysis of the sample 50, the computer 10 analyzes the refractive indices and the extinction coefficients (collectively referred to as optical constants, in some cases hereinafter) as the optical characteristics of: the lower layer film 300 and the first film 301 constitutes the first stack 31; and the lower layer film 300 and the second film 302 constitutes the second stack 32. The computer 10 analyzes also the film thicknesses and the like of these layers. With reference to the coordinate value file 151, the CPU 11 successively moves the stage and performs measurement of the first stack 31 and the second stack 32.

FIG. 14 is an explanation diagram illustrating a record layout of the coordinate value file 151 according to Embodiment 2. The coordinate value file 151 stores for each set 30 the first reference coordinates of the first stack 31 and the auxiliary reference coordinates of the second stack 32 (referred to as the second reference coordinates, hereinafter). The coordinate value file 151 has a set ID field, a first reference coordinate field, and a second reference coordinate field. Each set ID field stores a unique ID for identifying one of the sets 30, 30, 30, . . . . Each first reference coordinate field stores coordinate values where measurement on the first stack 31 is to be performed. Here, the present embodiment is described for an exemplary case that coordinate values are stored. However, distances may be stored that are uniquely converted from the coordinate values.

Figure 15:
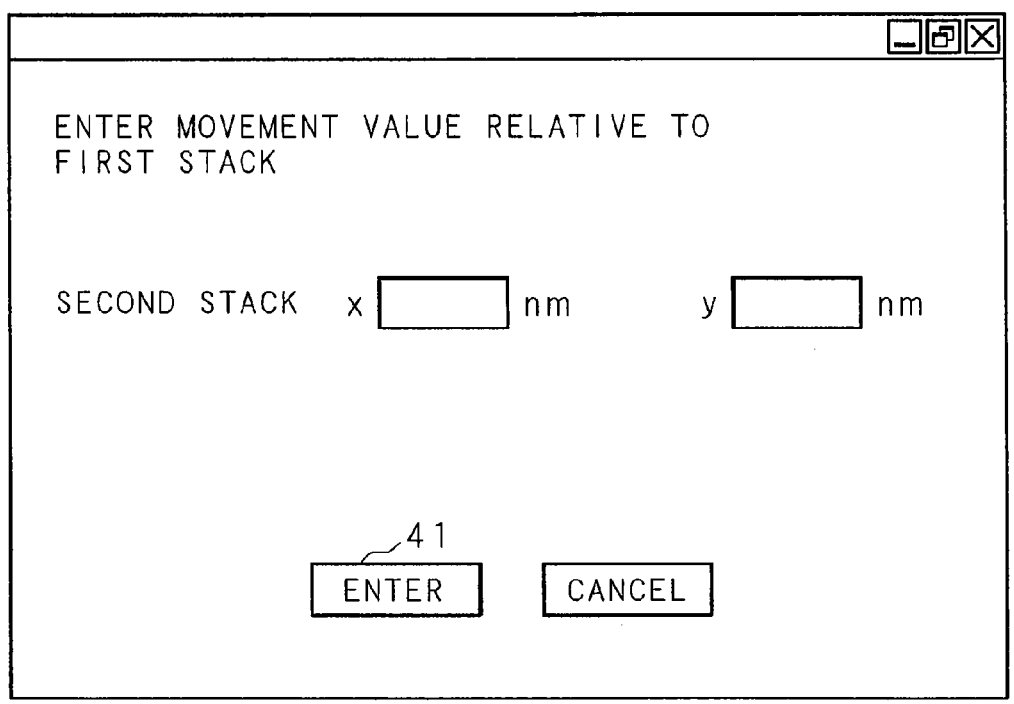
FIG. 15 is an explanation diagram illustrating a conceptual image of a movement value input screen according to Embodiment 2.

Each second reference coordinate field stores coordinate values where measurement on the second stack 32 is to be performed. Since the second film 302 is formed at a position deviated from the first film 301 by a given distance, the movement value from the first reference coordinates adopted as the first reference position is inputted in advance through the input part 13. FIG. 15 is an explanation diagram illustrating a conceptual image of a movement value input screen according to Embodiment 2. The CPU 11 reads from the storage part 15 the movement value input screen image illustrated in FIG. 15, and then outputs the image onto the display part 14. The user inputs a movement value through the input part 13. When the movement values in the X-direction and the Y-direction are inputted through the input part 13 and then the determination button 41 is operated, the CPU 11 receives the inputted movement values. Here, the present embodiment is described for an exemplary case that each is inputted by the unit of nm. However, the movement value may be inputted by another unit such as μm.

The CPU 11 reads the coordinate step number per unit length stored in the storage part 15, and then calculates the movement coordinate step numbers. The CPU 11 adds the calculated movement coordinate step numbers to the first reference coordinates, so as to obtain the second reference coordinates. In the example of FIG. 14, the movement coordinate step numbers are (Sx, Ty). Thus, the second reference coordinates for the set ID 01 become (x1+Sx, y1+Ty). Here, the movement values may be concerning any one or both of the X-direction and the Y-direction. With reference to the coordinate value file 151, the CPU 11 controls the movement of the stage, then performs measurement on the first stack 31 at the first reference coordinates, and then performs measurement on the second stack 32 at the second reference coordinates.

On the basis of the measured amplitude ratio Ψ and phase difference Δ, when the complex refractive index of ambient around the substrate 51 and the sample 50 is known, the CPU 11 of the computer 10 uses a modeling program stored in advance in the storage part 15. Then, models corresponding to the items of the sample 50 set up by the user and the material structure of the sample 50 are generated and then stored into the model file 153. In the present embodiment, a first model for the first stack 31 corresponding to the first reference position and an auxiliary model for the second stack 32 corresponding to the auxiliary reference position (referred to as a second model, hereinafter) are stored in the model file 153. By using the first model stored in the analysis stage, the CPU 11 calculates the film thicknesses and the complex refractive indices of the lower layer film 300 and the first film 301 of the first stack 31. Similarly, by using the second model, the CPU 11 calculates the film thicknesses and the complex refractive indices of the lower layer film 300 and the second film 302 of the second stack 32.

With the refractive index n and the extinction coefficient k of a film layer to be analyzed, the complex refractive index N satisfies the relation of equation (2) given above.

Further, when the incident angle is $\phi$ and the wavelength of light irradiated by the light irradiator 3 is $\lambda$, the amplitude ratio $\Psi$ and the phase difference $\Delta$ measured by the ellipsometer outputted from the data acquisition device 8 satisfy the relation of the above-mentioned equation (3) with the film thickness d, the refractive index n, and the extinction coefficient k each of the first film 301, the second film 302, and the lower layer film 300 to be analyzed.

By using the film thickness of each layer to be analyzed and a dispersion equation expressing the wavelength dependence of the complex dielectric constant and having a plurality of parameters, the CPU 11 of the computer 10 performs the processing (fitting) of changing the film thickness, the dispersion equation parameters, and the like such as to minimize the difference between the model spectra ($\Psi_M(\lambda_i)$, $\Delta_M(\lambda_i)$) (polarization state) obtained from the stored model by theoretical calculation and the measured spectra ($\Psi_E(\lambda_i)$, $\Delta_E(\lambda_i)$) (polarization state) representing the measurement result outputted from the data acquisition device 8. Here, an example of an employable dispersion equation is equation (4) given above.

In equation (4), $\in$ in the left-hand part denotes the complex dielectric constant, while $\in_\infty$ represents the dielectric constant at high frequencies (the high frequency dielectric constant), and $\in_s$ represents the dielectric constant at low frequencies (the static dielectric constant). $\omega_{oj}$, $\omega_t$, and $\omega_p$ represent the oscillator, transverse and plasma frequency respectively. $\Gamma_0$, $\Gamma_D$, and $\gamma_j$ are the damping factors. $f_j$ represents the oscillator strength parameter. $f_j (= \in_{sj} - \in_\infty)$ holds. Further, the complex dielectric constant $\in$ (corresponding to $\in(\lambda)$) and the complex refractive index N (corresponding to $N(\lambda)$) satisfy the equation (5) given above.

The procedure of fitting is described below. When the sample 50 is measured, T measurement data pairs are denoted by Exp (i=1, 2, . . . , T) and the calculated data pairs from T models are denoted by Mod (i=1, 2, . . . , T). Further, the measurement error is assumed to have a normal distribution with a standard deviation $\sigma_i$. Then, the mean square error $\chi^2$ according to the least square method is obtained by equation (6) given above. Here, P indicates the number of parameters. A smaller value of mean square error $\chi^2$ indicates better agreement between the measurement result and the generated model. Thus, when a plurality of models are compared, a model having the smallest value of mean square error $\chi^2$ corresponds to the best model.

The above-mentioned series of processing concerning the sample analysis performed by the CPU 11 of the computer 10 is set forth in a computer program for analysis stored in the storage part 15. In the spectroscopic ellipsometer 1 according to the present embodiment, a plurality of model types (model structures) for the sample 50 generated in advance are stored in the model file 153 in the storage part 15. On the basis of the processing set forth in the computer program (modeling program) stored in the storage part 15, these model type structures are read and used for analysis.

The above-mentioned fitting based on a model is executed on each of the first stack 31 and the second stack 32. As a result, the CPU 11 obtains the film thickness and the dispersion equation parameters of each of the lower layer film 300 and the first film 301 of the first stack 31. Similarly, the CPU 11 calculates the film thickness and the dispersion equation parameters of each of the lower layer film 300 and the second film 302 of the second stack 32. With reference to the dispersion equation parameters and the like of each of the lower layer film 300 and the first film 301 of the first stack 31, the CPU 11 calculates the optical constants (the refractive index n and the extinction coefficient k) of each of the lower layer film 300 and the first film 301. Similarly, with reference to the dispersion equation parameters and the like of each of the lower layer film 300 and the second film 302 of the second stack 32, the CPU 11 calculates the optical constants (the refractive index n and the extinction coefficient k) of each of the lower layer film 300 and the second film 302.

The CPU 11 stores into the result DB 152 the film thicknesses, the optical constants, and the like obtained by the fitting. FIG. 16 is an explanation diagram illustrating a record layout of the result DB 152 according to Embodiment 2. The result DB 152 has a set ID field, a film field, a measured spectra field, a film thickness field, abnormality flag fields for film thickness, refractive index, and extinction coefficient, a refractive index field, and an extinction coefficient field. The CPU 11 executes processing of storage, retrieval, and the like of necessary information in an interactive manner by using an access interface corresponding to a database format such as SQL (Structured Query Language) in a schema in which keys of the fields in the result DB 152 are related to each other.

The result DB 152 stores the measured spectra, the film thickness, the optical constants, and the like of each of the first stack 31 and the second stack 32. Here, the example of FIG. 16 illustrates the contents of storage for the first stack 31. The set ID field stores each set ID described above. The film field stores the name of each film constituting the stack. In the example of FIG. 16, the first film 301 serving as an upper layer and the lower layer film 300 of the first stack 31 are stored. The measured spectra field stores the measured spectra ($\Psi_E(\lambda_i)$, $\Delta_E(\lambda_i)$) of each film of each set ID obtained by measurement.

The film thickness field stores the film thickness of each film of each set ID obtained by fitting between the model spectra ($\Psi_M(\lambda_i)$, $\Delta_M(\lambda_i)$) (abbreviated as $\Psi_M$ and $\Delta_M$, hereinafter) obtained by theoretical calculation based on the first model for the first stack 31 or the second model for the second stack 32 and the measured spectra ($\Psi_E(\lambda_i)$, $\Delta_E(\lambda_i)$) (abbreviated as $\Psi_E$ and $\Delta_E$, hereinafter). The refractive index field and the extinction coefficient field respectively store the refractive index and the extinction coefficient of each film of each set ID calculated from the dispersion equation parameters obtained by fitting.

Each abnormality flag field stores a flag indicating abnormality when each of the film thickness and the optical constants of each film of each set ID falls outside a given range of reference film thickness or reference optical constant (reference refractive index or reference extinction coefficient) stored in advance. In the example of FIG. 16, each open circle indicates an abnormality flag. As seen from the figure, abnormality is present in the film thickness and the extinction coefficient of the first film 301 of the set ID 01. The reference film thickness and the given range are stored in advance in the storage part 15. As for the reference film thickness and the given range, appropriate values may be inputted through the input part 13 by the user, and then stored into the storage part 15. Each given range indicates an allowable error, and may be expressed, for example, as the reference film thickness±several nm. Alternatively, the range may be expressed as 99% to 101% (±1%) or the like of the reference film thickness.

Similarly, as for the refractive index and the extinction coefficient, a reference refractive index, a reference extinction coefficient, and given ranges are stored in advance in the storage part 15. Here, the exemplary layout of the result DB 152 is merely illustrative. Thus, as long as the relation between data pieces is maintained, arbitrary data layout may be adopted depending on the design. When measurement processing has been completed on all sets 30, the CPU 11 outputs a result onto the display part 14.

Figure 17:
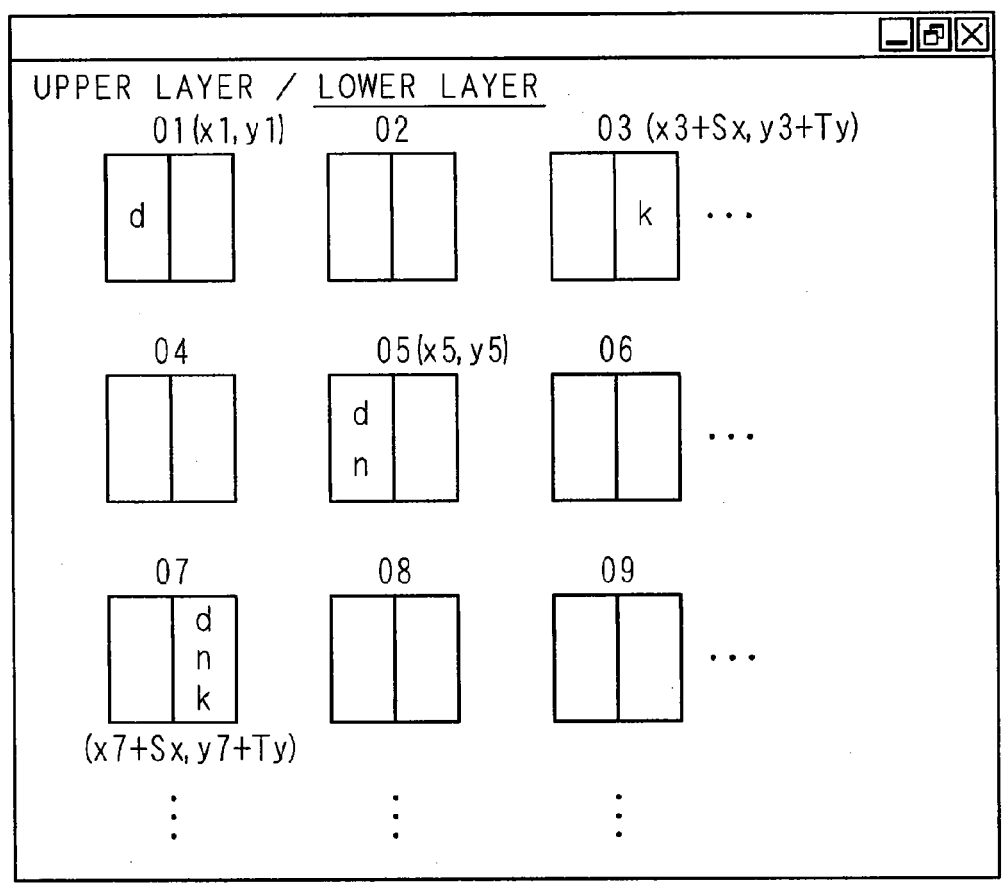
FIG. 17 is an explanation diagram illustrating a conceptual image of a result display screen according to Embodiment 2.

FIG. 17 is an explanation diagram illustrating a conceptual image of a result display screen according to Embodiment 2. With reference to the first reference coordinates and the second reference coordinates in the coordinate value file 151, the CPU 11 outputs, onto the display part 14, rectangular frames each indicating the first stack 31 and the second stack 32 constituting each set 30. As illustrated in FIG. 17, frames indicating the first stacks 31 and frames indicating the second stacks 32 are displayed on the display part 14 together with set IDs indicating the sets 30. With reference to the result DB 152, the CPU 11 searches abnormality flags concerning the film thickness, the refractive index, and the extinction coefficient of each film other than the lower layer film 300, that is, of each of the first films 301 and the second films 302. When an abnormality flag is set up concerning the film thickness of a first film 301, the CPU 11 displays "d" indicating the film thickness, into a frame concerning the first film of the corresponding set ID.

Similarly, when an abnormality flag is set up concerning the refractive index of a first film 301, the CPU 11 displays "n" indicating the refractive index, into a frame concerning the first film of the corresponding set ID. Further, when an abnormality flag is set up concerning the extinction coefficient of a first film 301, the CPU 11 displays "k" indicating the extinction coefficient, into a frame concerning the first film of the corresponding set ID. Similarly, as for the second films 302, a signal "d", "n", or "k" indicating the abnormality is outputted into a frame concerning the second film of the corresponding set ID.

Further, with reference to the coordinate value file 151, the CPU 11 outputs onto the display part 14 the coordinate values of the first stack 31 or the second stack 32 in which at least one abnormality flag is set up. In the example of FIG. 17, as seen from figure, abnormality is present in the film thickness of the first film 301 concerning the first stack 31 of the set ID 01 indicated by the first reference coordinates (x1, y1). Further, as seen from the figure, abnormality is present in all of the film thickness, the refractive index, and the extinction coefficient of the second film 302 concerning the second stack 32 of the set ID 07 indicated by the second reference coordinates (x7+Sx, y7+Ty). As illustrated in FIG. 17, the present embodiment has been described for an exemplary case that abnormality is present in the first stacks 31 and the second stacks 32 serving as upper layers. However, obviously, the abnormality state of the lower layer film 300 serving as a lower layer may similarly be illustrated. When the hyperlink "Lower layer" displayed in FIG. 17 is clicked, the CPU 11 performs the following processing. With reference to the first reference coordinates in the coordinate value file 151, the CPU 11 outputs, onto the display part 14, rectangular frames indicating the lower layer films 300. Similarly to the display for the first stacks 31 and the second stacks 32, frames indicating the lower layer films 300 and set IDs indicating the sets 30 are displayed on the display part 14. With reference to the result DB 152, the CPU 11 searches abnormality flags concerning the film thickness, the refractive index, and the extinction coefficient of each lower layer film 300. When an abnormality flag is set up concerning the film thickness of a lower layer film 300, the CPU 11 displays "d" indicating the film thickness, into the frame of the corresponding set ID. Similarly, when an abnormality flag is set up concerning the refractive index of a lower layer film 300, the CPU 11 displays "n" indicating the refractive index, into the frame of the corresponding set ID. Further, when an abnormality flag is set up concerning the extinction coefficient of a lower layer film 300, the CPU 11 displays "k" indicating the extinction coefficient, into the frame of the corresponding set ID. Further, with reference to the coordinate value file 151, the CPU 11 outputs onto the display part 14 the coordinate values of the lower layer film 300 in which at least one abnormality flag is set up. For convenience of page space, the screen displaying abnormality in the lower layer film 300 and the screen displaying abnormality in the first stack 31 and the second stack 32 have been illustrated separately. However, obviously, these screens may be integrated into one.

Figure 18:
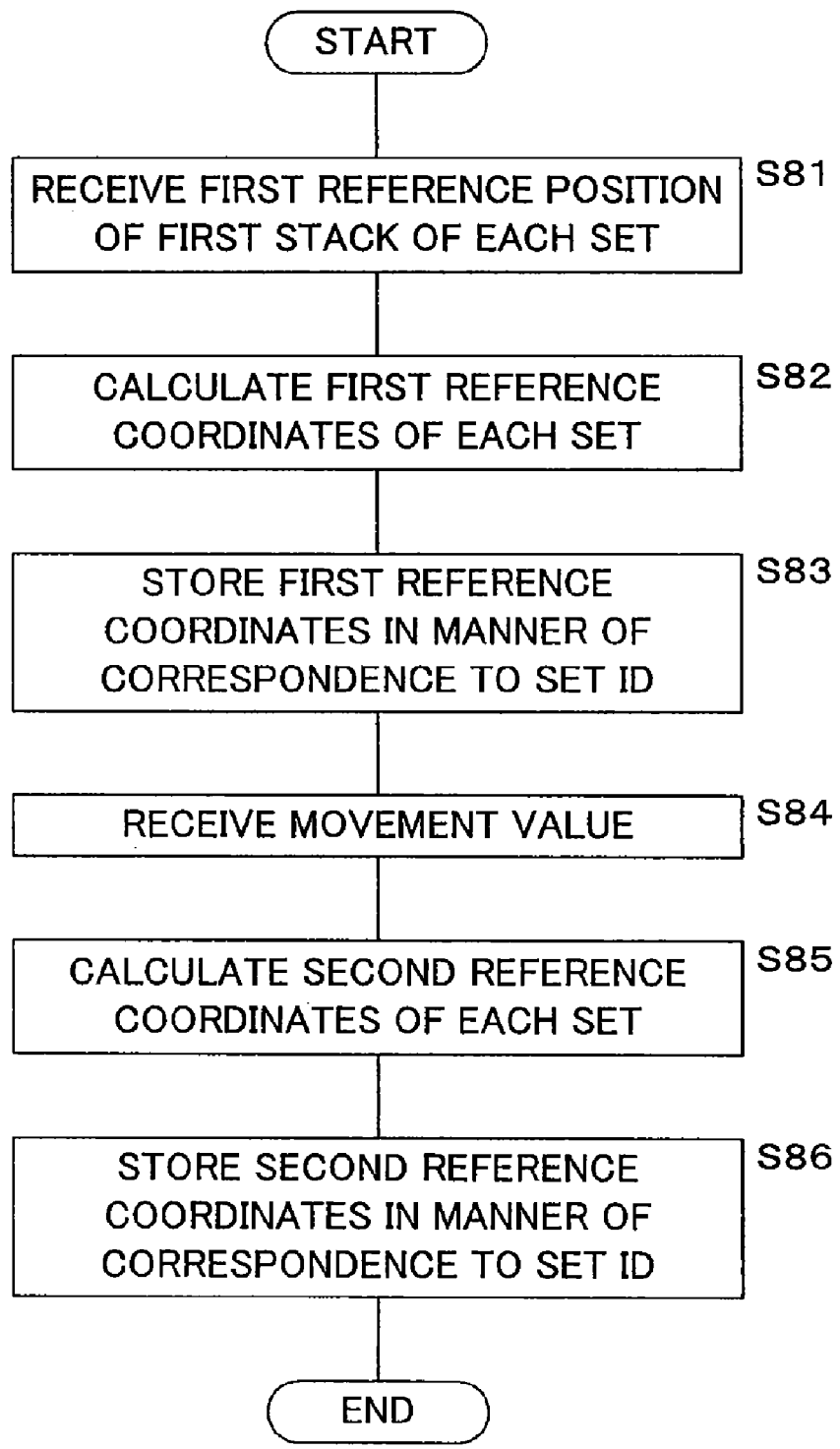
FIG. 18 is a flow chart illustrating a procedure of storage processing for coordinate values according to Embodiment 2.

The procedure of each software processing executed in the above-mentioned hardware configuration is described below with reference to each flow chart. FIG. 18 is a flow chart illustrating a procedure of storage processing for coordinate values according to Embodiment 2. The CPU 11 receives the first reference position of the first stack 31 of each set 30 (step S81). As for the first reference position, the user may input appropriate numerical values through the input part 13. Alternatively, the CPU 11 may receive a first reference position acquired by reading a recording medium (not illustrated) or a first reference position acquired by download through a communication network. With reference to the coordinate value per unit length stored in the storage part 15, the CPU 11 calculates the first reference coordinates of each set 30 corresponding to the first received reference position (step S82).

The CPU 11 stores into the coordinate value file 151 the calculated first reference coordinates in a manner of correspondence to the set ID (step S83). The CPU 11 reads the movement value input screen image stored in the storage part 15, and then outputs the image onto the display part 14. The CPU 11 receives the movement value inputted through the input part 13 (step S84). On the basis of the coordinate value per unit length, the movement value, and the first reference coordinates having been received, the CPU 11 calculates the second reference coordinates of each set (step S85). The CPU 11 stores into the coordinate value file 151 the second reference coordinates in a manner of correspondence to the set ID (step S86).

Figure 19A:
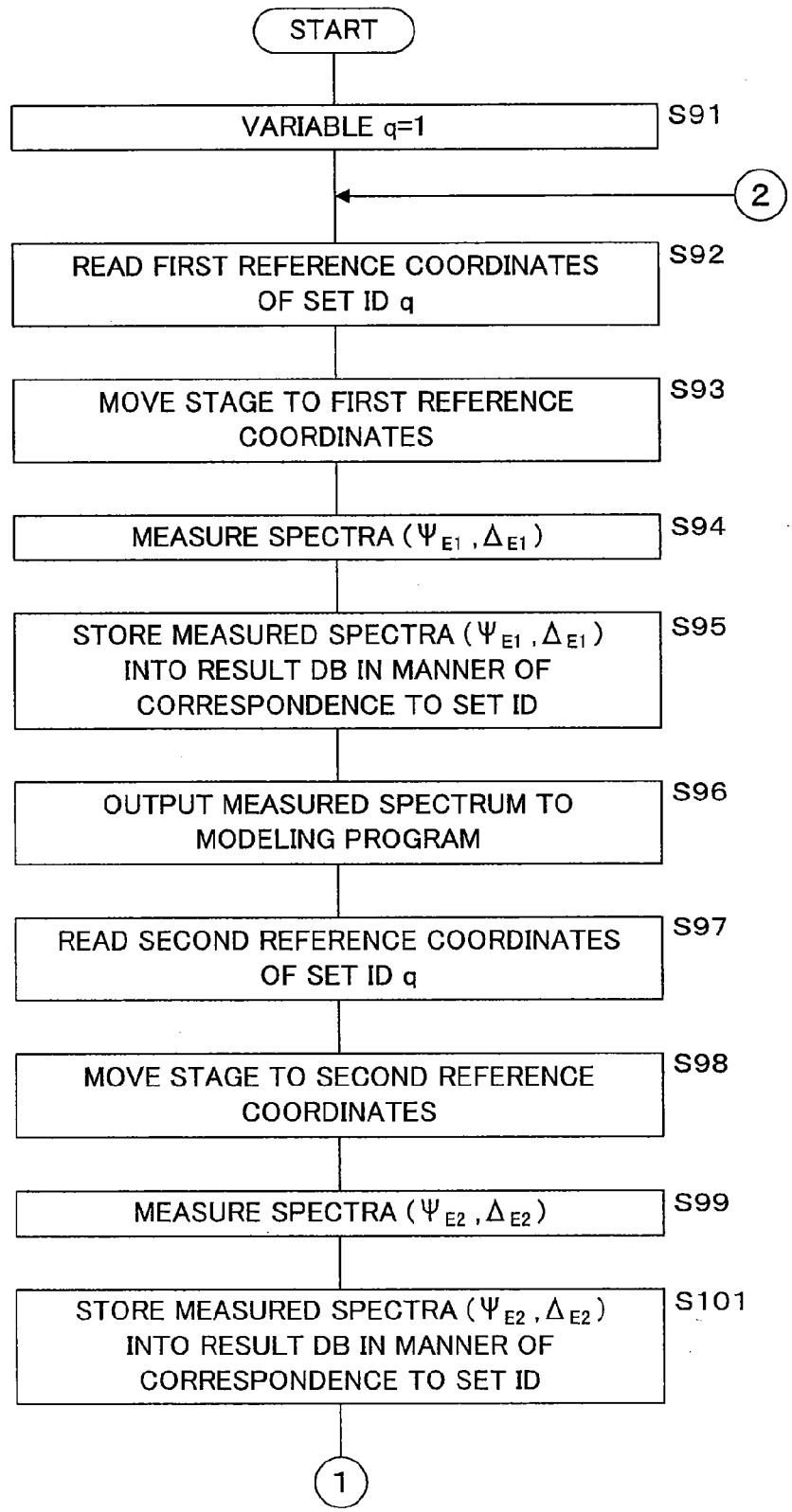
Figure 20A:
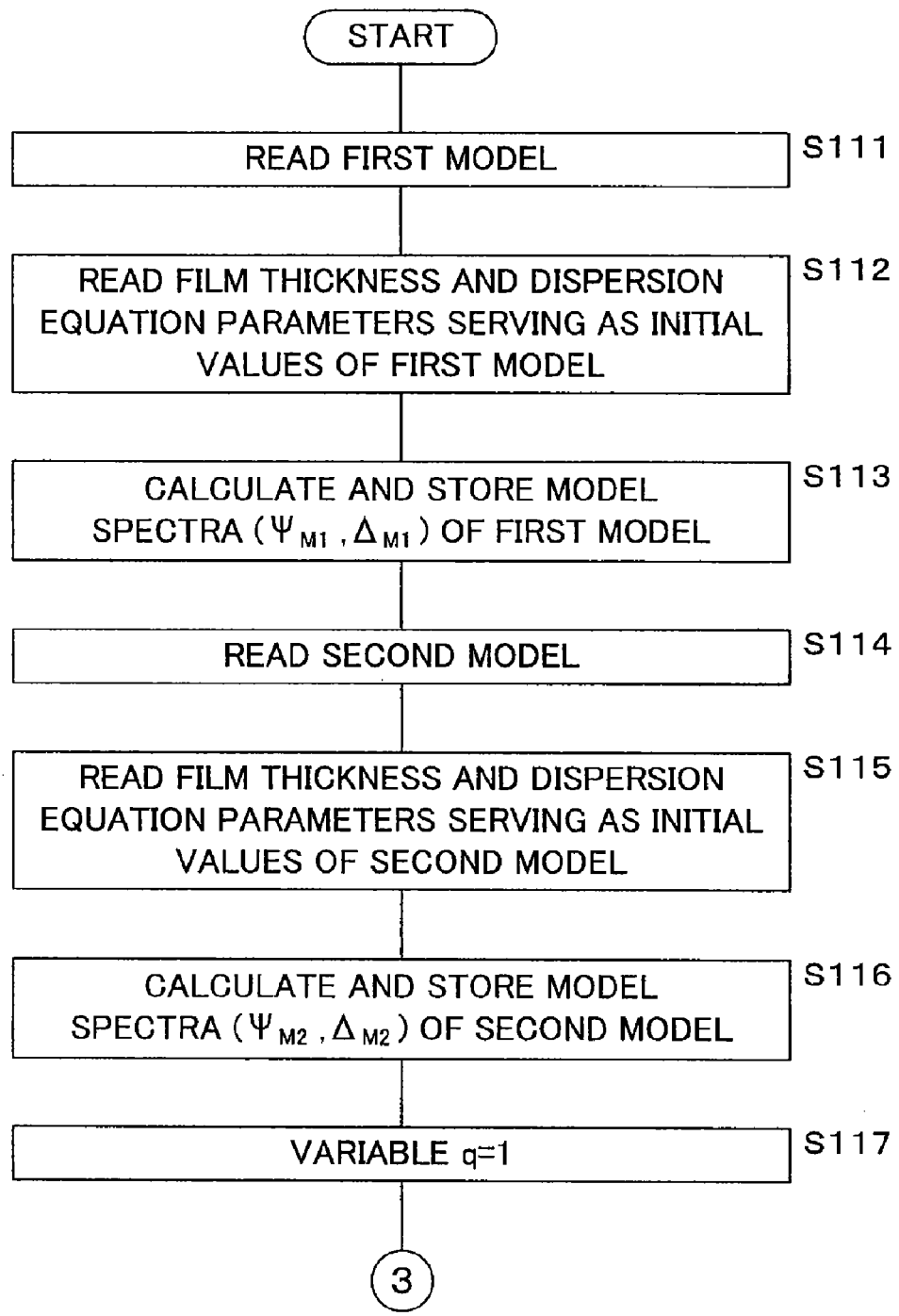
FIGS. 20A to 20C are flow charts illustrating a procedure of calculating a film thickness and optical constants according to Embodiment 2.
Figure 20B:
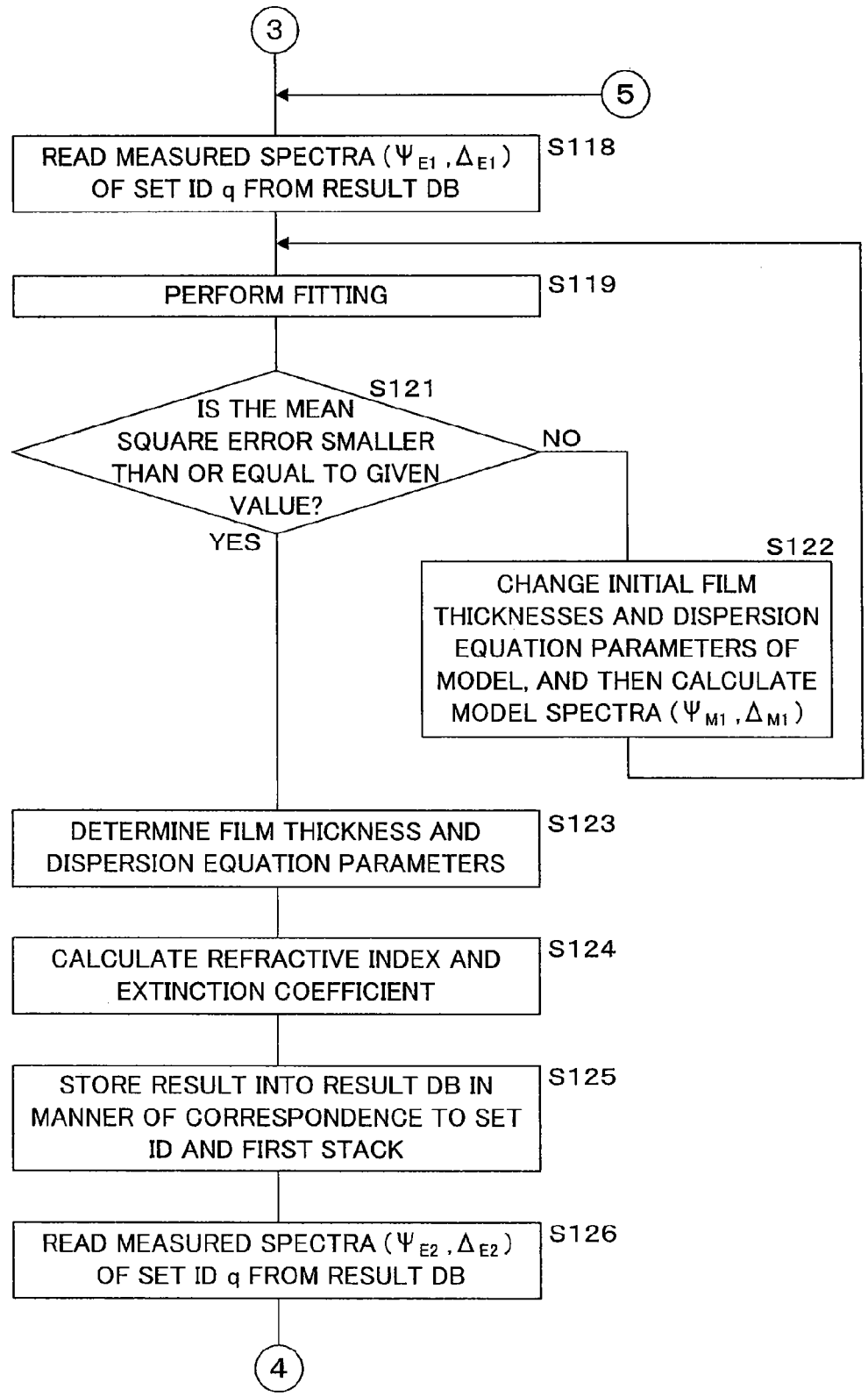
Figure 20C:
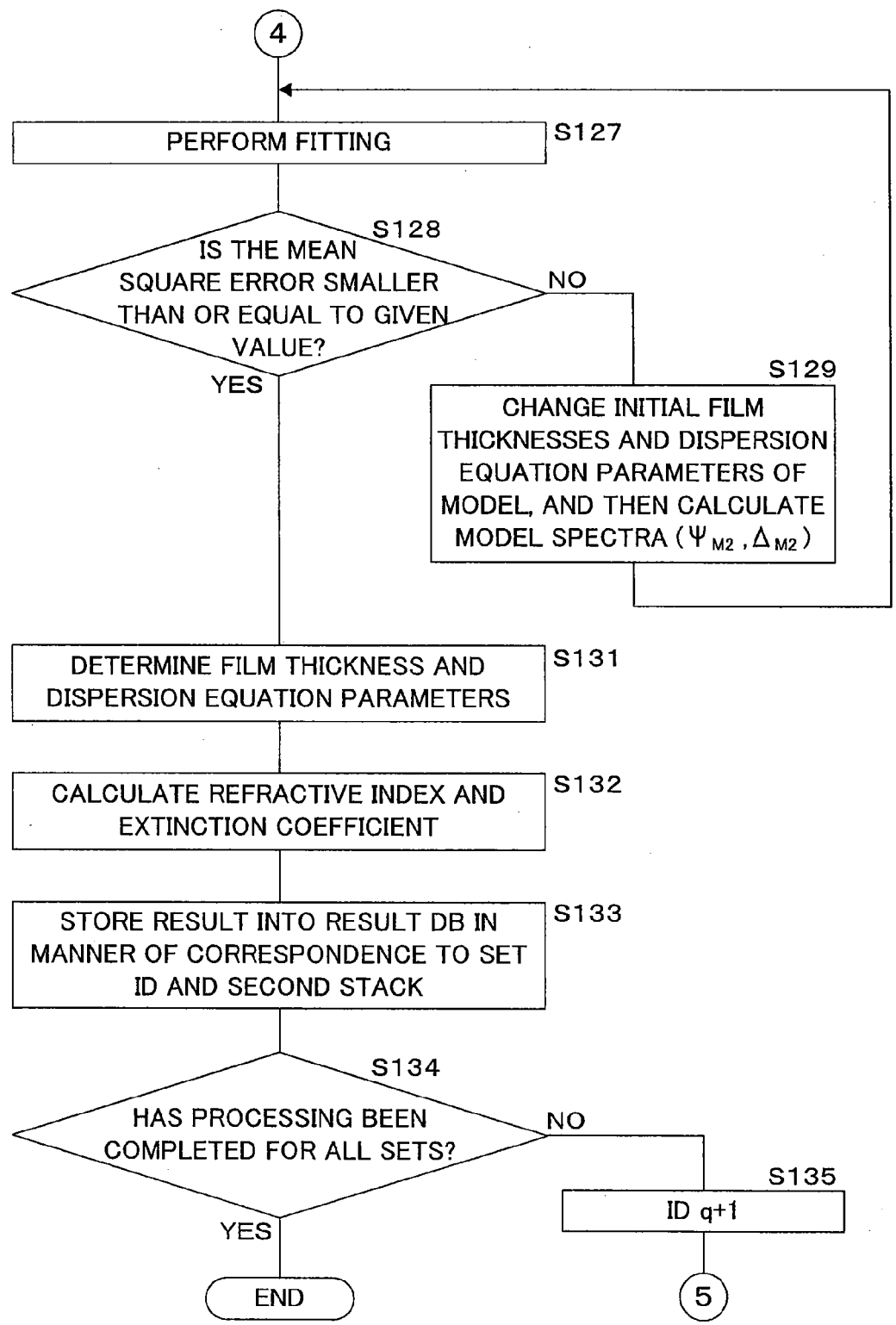

FIGS. 19A and 19B are flow charts illustrating a procedure of measurement processing according to Embodiment 2. The CPU 11 substitutes 1 into the variable q (step S91). The CPU 11 reads from the coordinate value file 151 the first reference coordinates of the set ID q (step S92). When the variable q is 1, the first reference coordinates of the set ID "01" are read. The CPU 11 controls the first motor M1 and the second motor M2 through the motor controller 9 so as to move the stage to the first reference coordinates (step S93). Then, measurement preparation for the first stack 31 is completed. Then, the CPU 11 of the spectroscopic ellipsometer 1 controls the light irradiator 3 and the light obtainer 5 so as to irradiate light onto the first stack 31, and then acquires a measured spectra $(\Psi_{E1}, \Delta_{E1})$ (step S94). The CPU 11 receives the measured spectra $(\Psi_{E1}, \Delta_{E1})$ outputted from the data acquisition device 8, and then stores the data into the result DB 152 in a manner of correspondence to the set ID (step S95).

For the purpose of fitting, the CPU 11 outputs the measured spectra $(\Psi_{E1}, \Delta_{E1})$ to the modeling program (step S96). The fitting processing is described later. The CPU 11 reads from the coordinate value file 151 the second reference coordinates of the set ID q (step S97). The CPU 11 controls the first motor M1 and the second motor M2 through the motor controller 9 so as to move the stage to the second reference coordinates (step S98). Then, measurement preparation for the second stack 32 is completed. Then, the CPU 11 of the spectroscopic ellipsometer 1 controls the light irradiator 3 and the light obtainer 5 so as to irradiate light onto the second stack 32, and then acquires a measured spectra $(\Psi_{E2}, \Delta_{E2})$ (step S99).

The CPU 11 receives the measured spectra $(\Psi_{E2}, \Delta_{E2})$ outputted from the data acquisition device 8, and then stores the data into the result DB 152 in a manner of correspondence to the set ID (step S101). Here, analysis need not be performed immediately after the measurement, and may be performed later. For the purpose of fitting, the CPU 11 outputs the measured spectra ($\Psi_{E2}$, $\Delta_{E2}$) to the modeling program (step S102). The CPU 11 determines whether the processing has been completed for all sets 30 (step S103). When it is determined that the processing is not yet completed for all sets 30 (NO at step S103), the CPU 11 increments the variable q (step S104). Then, the CPU 11 returns the procedure to step S92, and then acquires the measured spectra of the next set 30. In contrast, when it is determined that the processing has been completed for all sets 30 (YES at step S103), the CPU 11 terminates the series of processing.

Figure 24A:
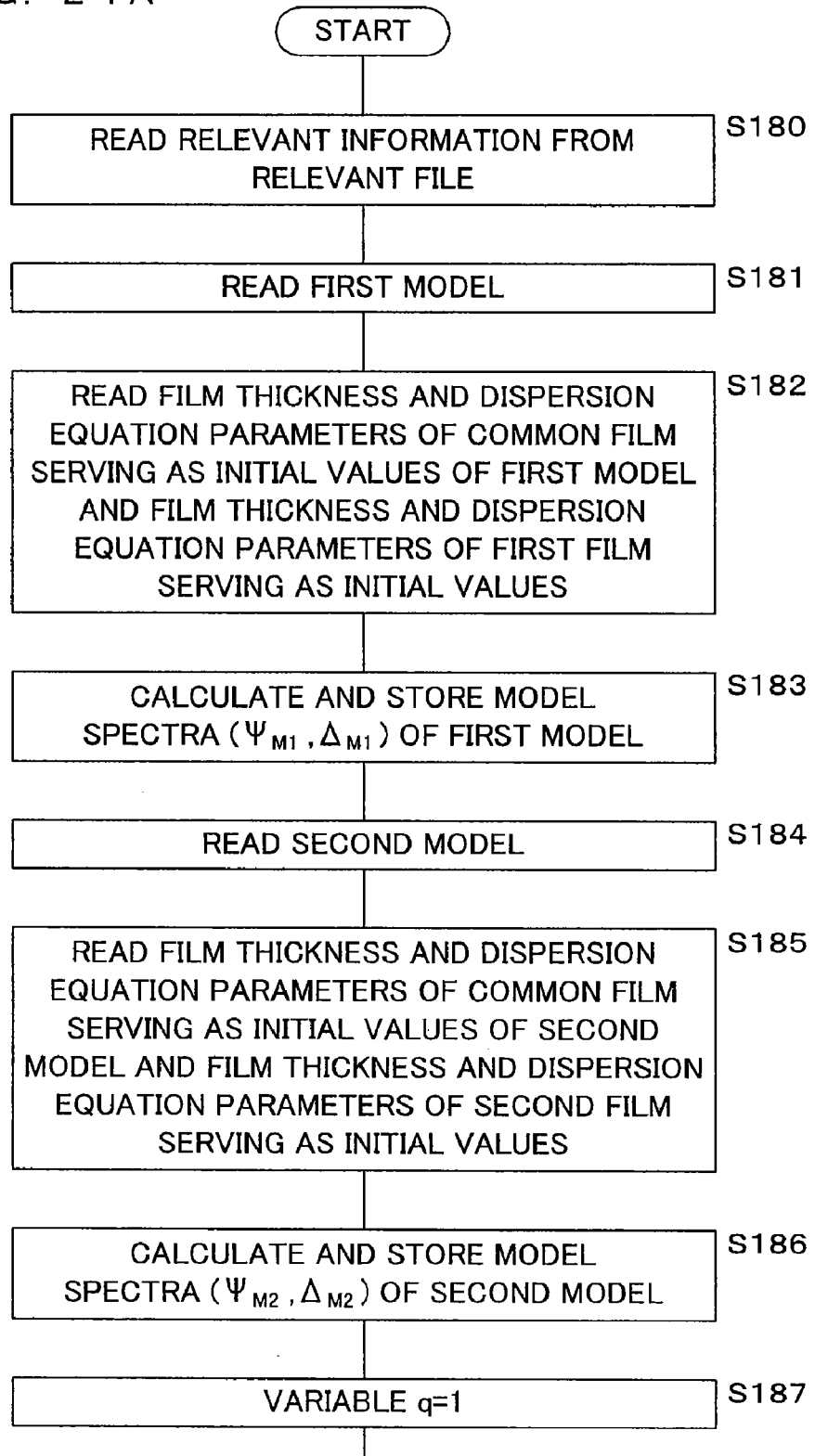
Figure 24B:
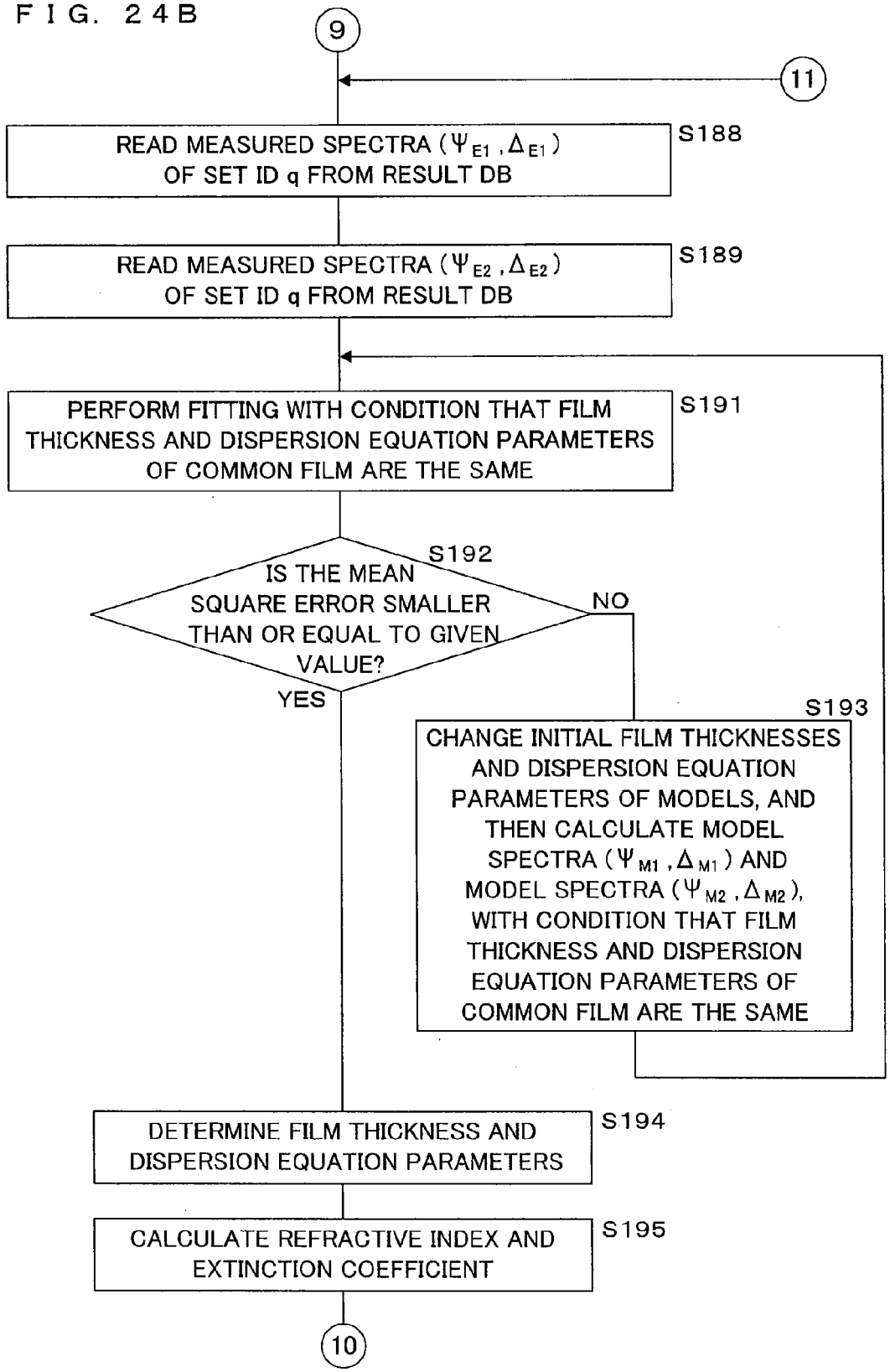

FIGS. 24A to 24C are flow charts illustrating a procedure of calculating a film thickness and optical constants according to Embodiment 2. The CPU 11 reads the first model from the model file 153 (step S111). In accordance with the read-out first model, the CPU 11 reads from the storage part 15 a plurality of film thicknesses and a plurality of dispersion equation parameters serving as the initial values stored in advance (step S112). On the basis of the first model, the initial film thickness, and the parameters having been read, the CPU 11 calculates the model spectra ($\Psi_{M1}$, $\Delta_{M1}$) of the first model, and then stores the result into the storage part 15 (step S113).

The CPU 11 reads the second model from the model file 153 (step S114). In accordance with the read-out second model, the CPU 11 reads from the storage part 15 a plurality of film thicknesses and a plurality of dispersion equation parameters serving as the initial values stored in advance (step S115). On the basis of the second model, the initial film thickness, and the parameters having been read, the CPU 11 calculates the model spectra ($\Psi_{M2}$, $\Delta_{M2}$) of the second model, and then stores the result into the storage part 15 (step S116).

The CPU 11 substitutes 1 into the variable q (step S117). The CPU 11 reads from the result DB 152 the measured spectra ($\Psi_{E1}$, $\Delta_{E1}$) of the set ID q (step S118). On the basis of the read-out measured spectra ($\Psi_{E1}$, $\Delta_{E1}$) and the model spectra ($\Psi_{M1}$, $\Delta_{M1}$) of the first model, the CPU 11 performs fitting (step S119). Specifically, the CPU 11 performs the processing (fitting) of comparing with each other the measured spectra ($\Psi_{E1}$, $\Delta_{E1}$) and the model spectra ($\Psi_{M1}$, $\Delta_{M1}$) of the first model having been read for the fitting, and then changing the film thickness, the dispersion equation parameters, and the like so as to minimize the difference between the measured spectra and the model spectra. As a result of the fitting, the CPU 11 obtains a mean square error $\chi^2$ according to the least square method. The mean square error $\chi^2$ is calculated in accordance with equation (2) given above.

As a result of the fitting, the CPU 11 determines whether the calculated mean square error is smaller than or equal to a given value (step S121). This given value is stored in the storage part 15. When it is determined that the calculated mean square error is not smaller than or equal to the given value (NO at step S121), the CPU 11 appropriately changes the film thickness and the dispersion equation parameters having been set up as initial values in the first model, and then re-calculates the model spectra ($\Psi_{M1}$, $\Delta_{M1}$) of the first model (step S122). This change may be performed by the CPU 11, or alternatively by the operator. After that, the procedure goes to step S119 again, so that similar processing is repeated.

When it is determined that the calculated mean square error $\chi^2$ is smaller than or equal to the given value (YES at step S121), the CPU 11 determines that the film thickness and the dispersion equation parameters obtained at that time by fitting are the values to be adopted (step S123). As a result, the film thickness of each of the lower layer film 300 and the first film 301 of the first stack 31 is obtained. Here, in processing at step S121, the processing is performed until the value becomes smaller than or equal to the given value. However, actual implementation is not limited to this. That is, the initial film thickness and dispersion equation parameters to be set into each model within a given time may be changed successively, and then a film thickness and dispersion equation parameters realized at the time when the minimum mean square error is obtained within the given time may be adopted as the obtained result.

With reference to the dispersion equation parameters and the like of the lower layer film 300 and the first film 301, the CPU 11 calculates the refractive index and the extinction coefficient of each of the lower layer film 300 and the first film 301 of the first stack 31(step S124). The CPU 11 stores into the result DB 152 the film thickness, the refractive index, and the extinction coefficient of each of the lower layer film 300 and the first film 301 in a manner of correspondence to the set ID and the first stack 31 (step S125).

The CPU 11 reads from the result DB 152 the measured spectra ($\Psi_{E2}$, $\Delta_{E2}$) of the set ID q (step S126). On the basis of the read-out measured spectra ($\Psi_{E2}$, $\Delta_{E2}$) and the model spectra ($\Psi_{E2}$, $\Delta_{M2}$) of the second model, the CPU 11 performs fitting (step S127). Specifically, the CPU 11 performs the processing (fitting) of comparing with each other the measured spectra ($\Psi_{E2}$, $\Delta_{E2}$) and the model spectra ($\Psi_{M2}$, $\Delta_{M2}$) of the second model having been read for the fitting, and then changing the film thickness, the dispersion equation parameters, and the like so as to minimize the difference between the measured spectra and the model spectra. As a result of the fitting, the CPU 11 obtains a mean square error $\chi^2$ according to the least square method. The mean square error $\chi^2$ is calculated in accordance with equation (2) given above.

As a result of the fitting, the CPU 11 determines whether the calculated mean square error is smaller than or equal to a given value (step S128). When it is determined that the calculated mean square error is not smaller than or equal to the given value (NO at step S128), the CPU 11 appropriately changes the film thickness and the dispersion equation parameters having been set up as initial values in the second model, and then re-calculates the model spectra ($\Psi_{M2}$, $\Delta_{M2}$) of the second model (step S129). After that, the procedure goes to step S127 again, so that similar processing is repeated.

When it is determined that the calculated mean square error $\chi^2$ is smaller than or equal to the given value (YES at step S128), the CPU 11 determines that the film thickness and the dispersion equation parameters obtained at that time by fitting are the values to be adopted (step S131). As a result, the film thickness of each of the lower layer film 300 and the second film 302 of the second stack 32 is obtained. With reference to the dispersion equation parameters and the like of the lower layer film 300 and the second film 302, the CPU 11 calculates the refractive index and the extinction coefficient of each of the lower layer film 300 and the second film 302 concerning the second stack 32 (step S132). The CPU 11 stores into the result DB 152 the film thickness, the refractive index, and the extinction coefficient of each of the lower layer film 300 and the second film 302 in a manner of correspondence to the set ID and the second stack 32 (step S133).

The CPU 11 determines whether the processing has been completed for all sets 30 (step S134). When it is determined that the processing is not yet completed for all sets 30 (NO at step S134), the CPU 11 increments the variable q (step S135). The CPU 11 returns the procedure to step S118 so as to perform calculation of the film thickness and the optical constants of the next set 30. In contrast, when it is determined that the processing has been completed for all sets 30 (YES at step S134), the CPU 11 terminates the series of processing. According to this approach, merely when the coordinate value file 151 is generated and the corresponding models are prepared in the beginning, the film thicknesses and the optical constants of the first stack 31 and the second stack 32 of each set 30 serving as a measurement object are acquired.

Figure 21B:
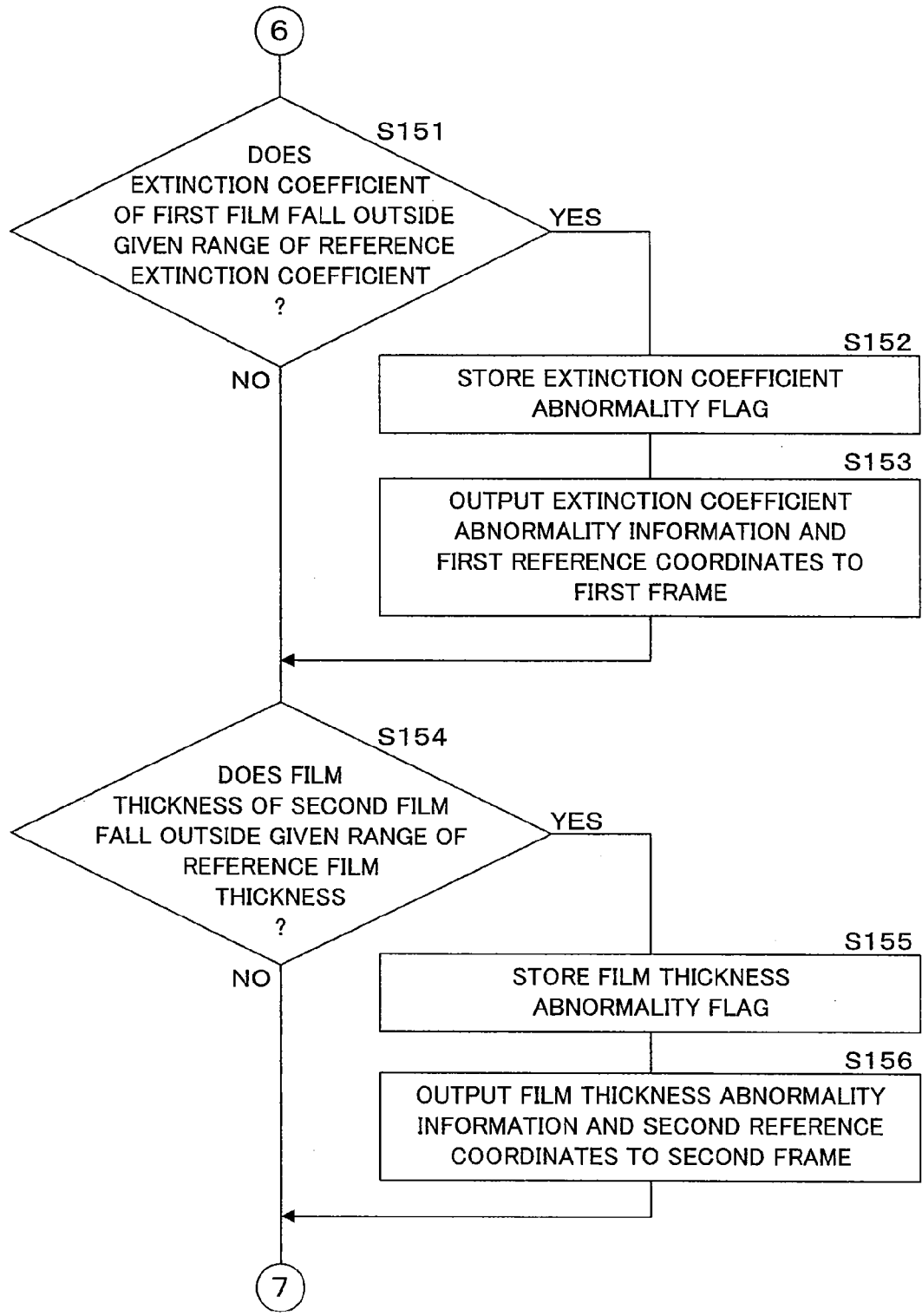
Figure 21C:
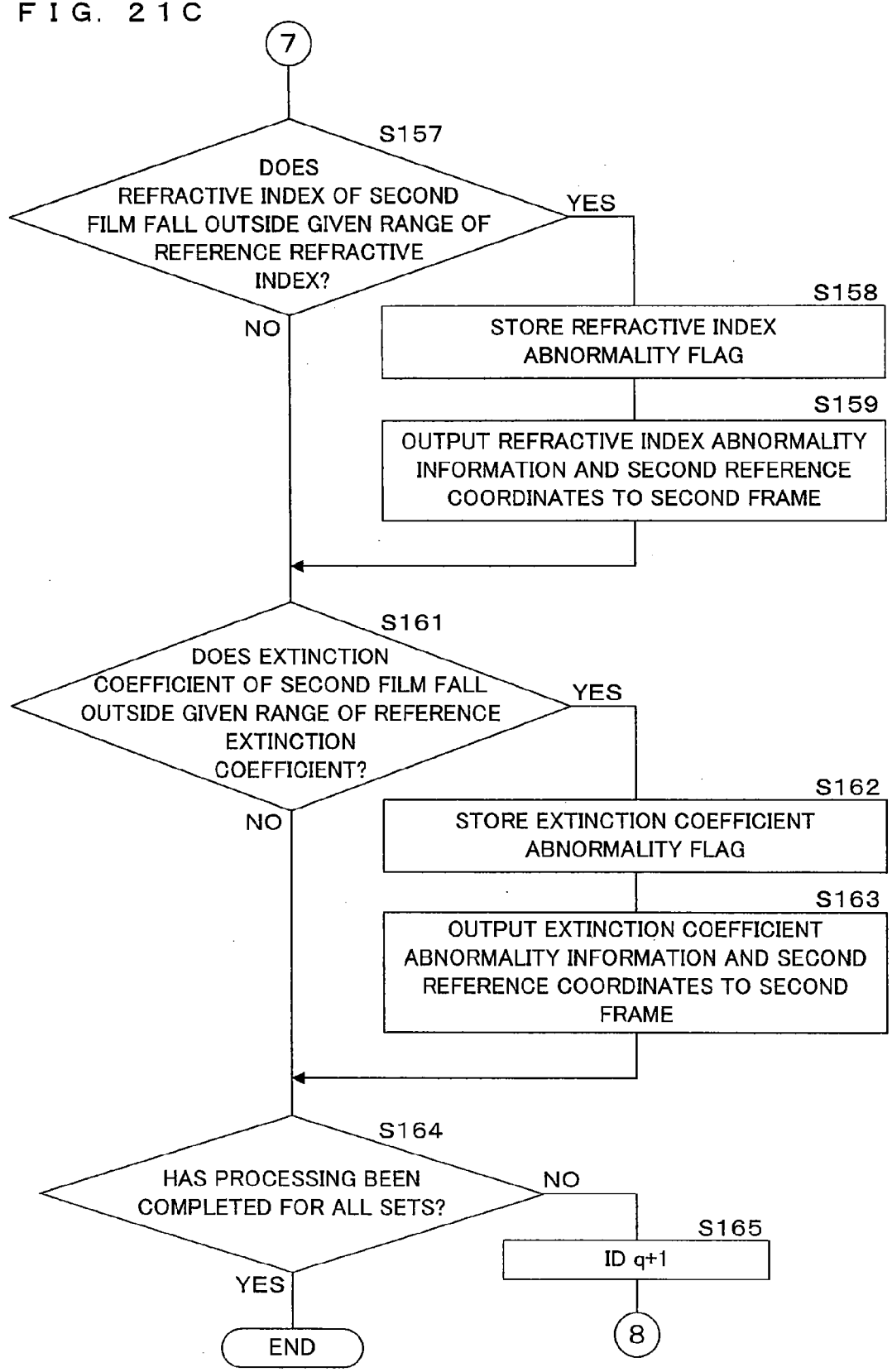

FIGS. 21A to 21C are flow charts illustrating a procedure of abnormality detection processing according to Embodiment 2. The CPU 11 substitutes an initial value 1 into the variable q (step S141). The CPU 11 reads from the coordinate value file 151 the first reference coordinates and the second reference coordinates of the set ID q (step S142). With reference to the first reference coordinates and the second reference coordinates, the CPU 11 outputs, onto the display part 14, two rectangular frames illustrated in FIG. 17. Specifically, with reference to the first reference coordinates, the CPU 11 outputs a first frame corresponding to the first stack 31, and then with reference to the second reference coordinates, outputs a second frame corresponding to the second stack 32. Further, the CPU 11 outputs the set ID in the vicinity (step S143).

The CPU 11 reads the film thickness of the first film 301 corresponding to the set ID q stored in the result DB 152. The CPU 11 determines whether the film thickness of the first film 301 falls outside a given range for the reference film thickness stored in advance in the storage part 15 (step S144). When it is determined as falling outside the given range (YES at step S144), the CPU 11 stores into the result DB 152 the film thickness abnormality flag in correspondence to the first film 301 of the set ID q (step S145). The CPU 11 outputs, into the first frame, information indicating the abnormality in the film thickness and the first reference coordinates corresponding to the set ID stored in the coordinate value file 151 (step S146). After this processing, or alternatively when it is determined as not falling outside the given range (NO at step S144), the CPU 11 moves the procedure to step S147.

The CPU 11 reads the refractive index of the first film 301 corresponding to the set ID q stored in the result DB 152. The CPU 11 determines whether the refractive index of the first film 301 falls outside a given range for the reference refractive index stored in advance in the storage part 15 (step S147). When it is determined as falling outside the given range (YES at step S147), the CPU 11 stores into the result DB 152 the refractive index abnormality flag in correspondence to the first film 301 of the set ID q (step S148). The CPU 11 outputs, into the first frame, information indicating the abnormality in the refractive index and the first reference coordinates corresponding to the set ID stored in the coordinate value file 151 (step S149). Here, when the first reference coordinates are already outputted at step S146, re-output is unnecessary. After this processing, or alternatively when it is determined as not falling outside the given range (NO at step S147), the CPU 11 moves the procedure to step S151.

The CPU 11 reads the extinction coefficient of the first film 301 corresponding to the set ID q stored in the result DB 152. The CPU 11 determines whether the extinction coefficient of the first film 301 falls outside a given range for the reference extinction coefficient stored in advance in the storage part 15 (step S151). When it is determined as falling outside the given range (YES at step S151), the CPU 11 stores into the result DB 152 the extinction coefficient abnormality flag in correspondence to the first film 301 of the set ID q (step S152). The CPU 11 outputs, into the first frame, information indicating the abnormality in the extinction coefficient and the first reference coordinates corresponding to the set ID stored in the coordinate value file 151 (step S153). After this processing, or alternatively when it is determined as not falling outside the given range (NO at step S151), the CPU 11 moves the procedure to step S154.

The CPU 11 reads the film thickness of the second film 302 corresponding to the set ID q stored in the result DB 152. The CPU 11 determines whether the film thickness of the second film 302 falls outside a given range for the reference film thickness stored in advance in the storage part 15 (step S154). When it is determined as falling outside the given range (YES at step S154), the CPU 11 stores into the result DB 152 the film thickness abnormality flag in correspondence to the second film 302 of the set ID q (step S155). The CPU 11 outputs, into the second frame, information indicating the abnormality in the film thickness and the second reference coordinates corresponding to the set ID stored in the coordinate value file 151 (step S156). After this processing, or alternatively when it is determined as not falling outside the given range (NO at step S154), the CPU 11 moves the procedure to step S157.

The CPU 11 reads the refractive index of the second film 302 corresponding to the set ID q stored in the result DB 152. The CPU 11 determines whether the refractive index of the second film 302 falls outside a given range for the reference refractive index stored in advance in the storage part 15 (step S157). When it is determined as falling outside the given range (YES at step S157), the CPU 11 stores into the result DB 152 the refractive index abnormality flag in correspondence to the second film 302 of the set ID q (step S158). The CPU 11 outputs, into the second frame, information indicating the abnormality in the refractive index and the second reference coordinates corresponding to the set ID stored in the coordinate value file 151 (step S159). After this processing, or alternatively when it is determined as not falling outside the given range (NO at step S157), the CPU 11 moves the procedure to step S161.

The CPU 11 reads the extinction coefficient of the second film 302 corresponding to the set ID q stored in the result DB 152. The CPU 11 determines whether the extinction coefficient of the second film 302 falls outside a given range for the reference extinction coefficient stored in advance in the storage part 15 (step S161). When it is determined as falling outside the given range (YES at step S161), the CPU 11 stores into the result DB 152 the extinction coefficient abnormality flag in correspondence to the second film 302 of the set ID q (step S162). The CPU 11 outputs, into the second frame, information indicating the abnormality in the extinction coefficient and the second reference coordinates corresponding to the set ID stored in the coordinate value file 151 (step S163). After this processing, or alternatively when it is determined as not falling outside the given range (NO at step S161), the CPU 11 moves the procedure to step S164.

The CPU 11 determines whether the processing has been completed for all sets 30 (step S164). When it is determined that the processing is not yet completed for all sets 30 (NO at step S164), the CPU 11 increments the variable q (step S165). The CPU 11 returns the procedure to step S142 so as to perform abnormality detection on the next set 30. In contrast, when it is determined that the processing has been completed for all sets 30 (YES at step S164), the CPU 11 terminates the series of processing. As a result, in accordance with and measurement of the film thickness and the optical constants of the measurement target, positions of abnormality are visually recognized easily. This improves the inspection efficiency and the production efficiency.

In the present Embodiment 2, the configuration given above is employed. The other points in the configuration and the operation are similar to those of Embodiment 1. Thus, Embodiment 3

Figure 22:
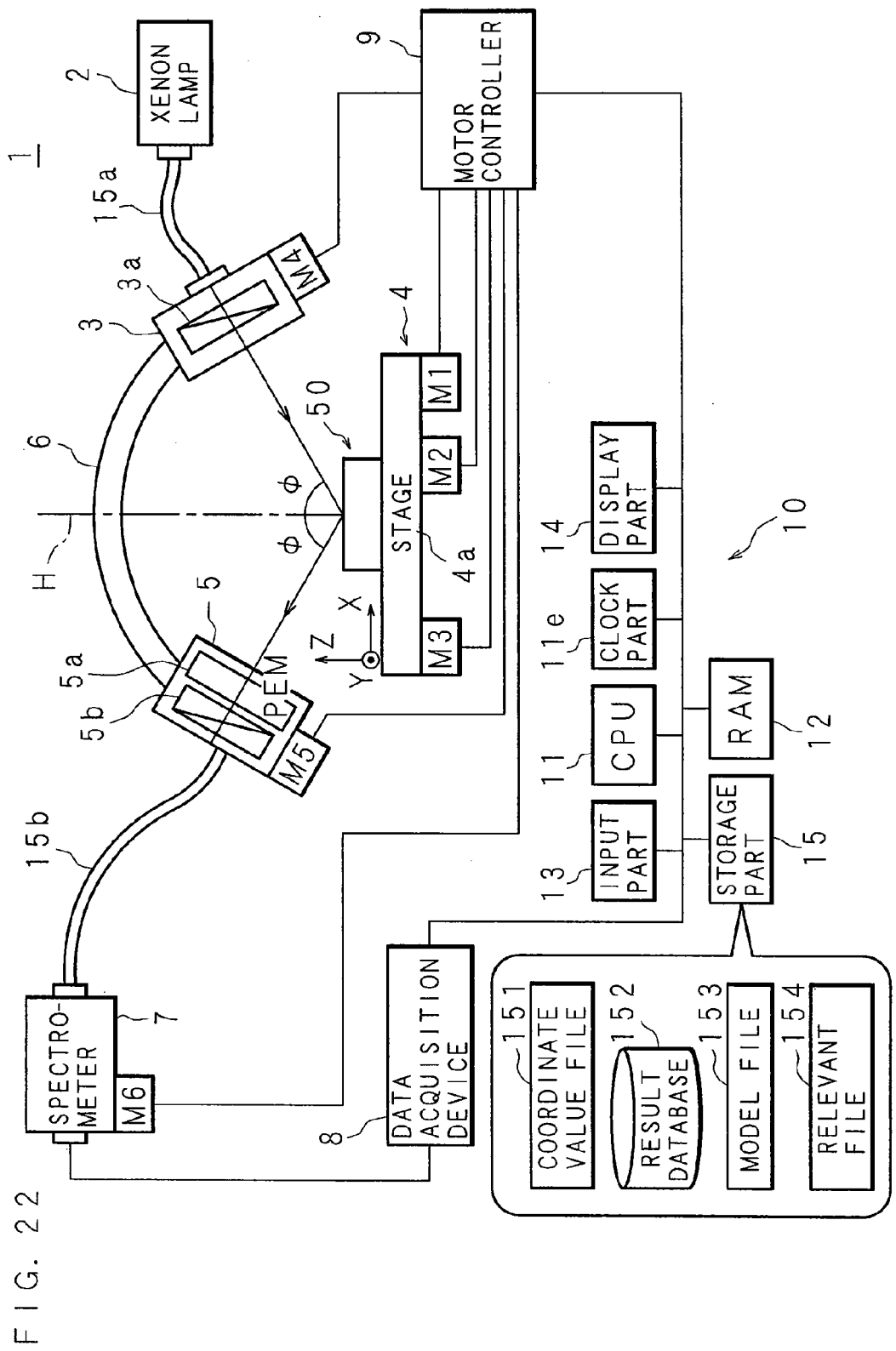
FIG. 22 is a block diagram illustrating a hardware configuration of a spectroscopic ellipsometer according to Embodiment 3.

Embodiment 3 relates to a mode that common parameters are employed. FIG. 22 is a block diagram illustrating a hardware configuration of a spectroscopic ellipsometer 1 according to Embodiment 3. In addition to the configuration of Embodiment 2, a relevant file 154 is stored in the storage part 15. The relevant file 154 stores relevant information indicating whether the film thickness or the optical constants of each layer constituting the first stack 31 and the second stack 32 are common to each other. With reference to the relevant information input screen through the input part 13, the user inputs relevant information.

FIG. 23 is an explanation diagram illustrating a conceptual image of a relevant information input screen according to Embodiment 3. With reference to the first model and the second model stored in the model file 153, the CPU 11 generates a relevant information input screen image, and then outputs the image onto the display part 14. The first model corresponds to the first stack 31, and is constructed from a lower layer film (referred to as a common film, hereinafter in the present embodiment) 300 and a first film 301 stacked thereon. The second model corresponds to the second stack 32, and is constructed from a common film 300 and a second film 302 stacked thereon. The present embodiment is described for an exemplary case that the film thickness and the optical constants of the common film 300 are common in the parameters in the first model and the second model.

The CPU 11 displays check boxes 300c for lower layer and check boxes 301c for upper layer used for inputting relevant information in accordance with each layer. The user clicks layers and common parameters through the input part 13. In the present embodiment, both of the film thickness and the optical constants are assumed to be common parameters. However, any one of these may solely be a common parameter. When a common film thickness serving as the initial value of the common film 300 and dispersion equation parameters corresponding to the optical constants are inputted through the input part 13, the CPU 11 stores these information pieces into the storage part 15. In the example of FIG. 23, the film thickness and the optical constants of the common film 300 are common parameters as indicated by the corresponding check boxes 300c. When receiving an input of the determination button 41, the CPU 11 stores into the relevant file 154 the relevant information received through the input part 13, that is, the layer and the common parameters. In the process of fitting, the CPU 11 performs fitting with taking such relevant information into consideration, that is, with the condition that the film thickness and the optical constants of the common film 300 are common in the first stack 31 and the second stack 32.

FIGS. 24A to 24C are flow charts illustrating a procedure of fitting processing according to Embodiment 3. The CPU 11 reads the relevant information stored in the relevant file 154 (step S180). The CPU 11 reads the first model from the model file 153 (step S181). In accordance with the read-out first model, the CPU 11 reads from the storage part 15: the film thickness and the dispersion equation parameters of the common film 300 serving as the initial values of the first model stored in advance; and the film thickness and the dispersion equation parameters of the first film 301 serving as the initial values of the first model (step S182). On the basis of the first model, the initial film thickness, and the parameters having been read, the CPU 11 calculates the model spectra ($\Psi_{M1}$, $\Delta_{M1}$) of the first model, and then stores the result into the storage part 15 (step S183).

The CPU 11 reads the second model from the model file 153 (step S184). In accordance with the read-out second model, the CPU 11 reads from the storage part 15: the film thickness and the dispersion equation parameters of the common film 300 serving as the initial values of the second model stored in advance; and the film thickness and the dispersion equation parameters of the second film 302 serving as the initial values of the second model (step S185). On the basis of the second model, the initial film thickness, and the parameters having been read, the CPU 11 calculates the model spectra ($\Psi_{M2}$, $\Delta_{M2}$) of the second model, and then stores the result into the storage part 15 (step S186).

The CPU 11 substitutes 1 into the variable q (step S187). Then, the CPU 11 reads from the result DB 152 the measured spectra ($\Psi_{E1}$, $\Delta_{E1}$) concerning the first stack 31 of the set ID q (step S188). Similarly, the CPU 11 reads from the result DB 152 the measured spectra ($\Psi_{E2}$, $\Delta_{E2}$) concerning the second stack 32 of the set ID q (step S189).

The CPU 11 performs the processing (fitting) of comparing with each other the measured spectra ($\Psi_{E1}$, $\Delta_{E1}$) concerning the first stack 31, the model spectra ($\Psi_{M1}$, $\Delta_{M1}$) of the first model, the measured spectra ($\Psi_{E2}$, $\Delta_{E2}$) concerning the second stack 32, and the model spectra ($\Psi_{M2}$, $\Delta_{M2}$) of the second model, which have been read for the purpose of fitting, and then changing the film thickness, the dispersion equation parameters, and the like such as to minimize the difference between each measured spectra and each model spectra with the condition that the film thickness and the dispersion equation parameters of the common film 300 are the same (step S191). As a result of the fitting, the CPU 11 obtains a mean square error $\chi^2$ according to the least square method. The mean square error $\chi^2$ at step S191 is calculated in accordance with equation (8).

$$\chi^2 = \frac{1}{2T_1 - P_1} \sum_{i=1}^{T_1} (\text{Exp}_i - \text{Mod}_i)^2 / \sigma_i^2 + \frac{1}{2T_2 - P_2} \sum_{i=1}^{T_2} (\text{Exp}_i - \text{Mod}_i)^2 / \sigma_i^2 \qquad (8)$$

Here, when measurement is performed on the first stack 31, T1 measurement data pairs are Exp (i=1, 2, ..., T1) and the calculated data pairs of T1 models are Mod (i=1, 2, ..., T1). When measurement is performed on the second stack 32, T2 measurement data pairs are Exp (i=1, 2, ..., T2) and the calculated data pairs of T2 models are Mod (i=1, 2, ..., T2). Further, P1 indicates the number of parameters in the measurement of the first stack 31, while P2 indicates the number of parameters in the measurement of the second stack 32.

As a result of the fitting, the CPU 11 determines whether the calculated mean square error is smaller than or equal to a given value (step S192). This given value is stored in the storage part 15.

When it is determined that the calculated mean square error is not smaller than or equal to the given value (NO at step S192), the CPU 11 goes to step S193. With the condition that the film thickness and the dispersion equation parameters of the common film 300 are the same, the CPU 11 appropriately changes the film thicknesses and the dispersion equation parameters having been set up as initial values of the models, and then re-calculates the model spectra ($\Psi_{M1}$, $\Delta_{M1}$) and the model spectra ($\Psi_{M2}$, $\Delta_{M2}$) (step S193). This change may be performed by the CPU 11, or alternatively by the operator.

After that, the procedure goes to step S191 again, so that similar processing is repeated.

When it is determined that the calculated mean square error is smaller than or equal to the given value (YES at step S192), the CPU 11 determines the film thickness and the dispersion equation parameters of each layer of the first stack 31, and further determines the film thickness and the dispersion equation parameters of each layer of the second stack 32 (step S194). Here, since the condition that the film thickness and the dispersion equation parameters of the common film 300 are the same is adopted, the film thickness of the common film 300 becomes the same in the first stack 31 and the second stack 32. Further, similarly to the film thickness, the refractive index and the extinction coefficient of the common film 300 obtained from the film thickness and the dispersion equation parameters are common in the first stack 31 and the second stack 32. With reference to the dispersion equation parameters and the like of the common film 300 and the first film 301, the CPU 11 calculates the refractive indices and the extinction coefficients of the common film 300 and the first film 301 of the first stack 31, and then with reference to the dispersion equation parameters and the like of the common film 300 and the second film 302, calculates the refractive indices and the extinction coefficients of the common film 300 and the second film 302 of the second stack 32 (step S195).

The CPU 11 stores into the result DB 152 the film thickness, the refractive index, and the extinction coefficient of each of the common film 300 and the first film 301 in a manner of correspondence to the set ID and the first stack 31 (step S196). Similarly, the CPU 11 stores into the result DB 152 the film thickness, the refractive index, and the extinction coefficient of each of the common film 300 and the second film 302 in a manner of correspondence to the set ID and the second stack 32 (step S197).

The CPU 11 determines whether the processing has been completed for all sets 30 (step S198). When it is determined that the processing is not yet completed for all sets 30 (NO at step S198), the CPU 11 increments the variable q (step S199). The CPU 11 returns the procedure to step S188 so as to perform fitting on the next set 30. In contrast, when it is determined that the processing has been completed for all sets 30 (YES at step S198), the CPU 11 terminates the series of processing. As a result, correlation between parameters is weakened, and hence an appropriate solution is obtained. After that, abnormality detection processing for the film thickness and the optical constants is performed similarly to FIGS. 21A to 21C of Embodiment 2. However, duplicated description is omitted.

In the present Embodiment 3, the configuration given above is employed. The other points in the configuration and the operation are similar to those of Embodiments 1 and 2. Thus, corresponding parts are designated by like reference numerals, and their detailed description is omitted.

Embodiment 4

Embodiment 4 relates to a mode that a larger number of stacks are formed. Embodiments 2 and 3 have been described for an exemplary case that the first stack 31 and the second stack 32 are provided. However, obviously, three or more stacks may be provided. The following description is given for an example that a third stack 33 is further provided. FIG. 25 is a schematic cross section of a sample according 50 to Embodiment 4. In addition to the configuration of Embodiments 2 and 3, a third stack 33 is formed adjacent to the second stack 32. On the common film 300, the second film 32 is formed adjacent to the third film 303. The third film 303 is composed of a substance having a film thickness or optical constants different from those of the first film 31 and the second film 32, and is composed of a silicon nitride film ($Si_3N_4$) or the like. A third stack 33 is constructed from the common film 300 and the third film 303. Sets 30 each composed of the combination of the first stack 31, the second stack 32, and the third stack 33 described above are distributed on the substrate 51.

Figure 26:
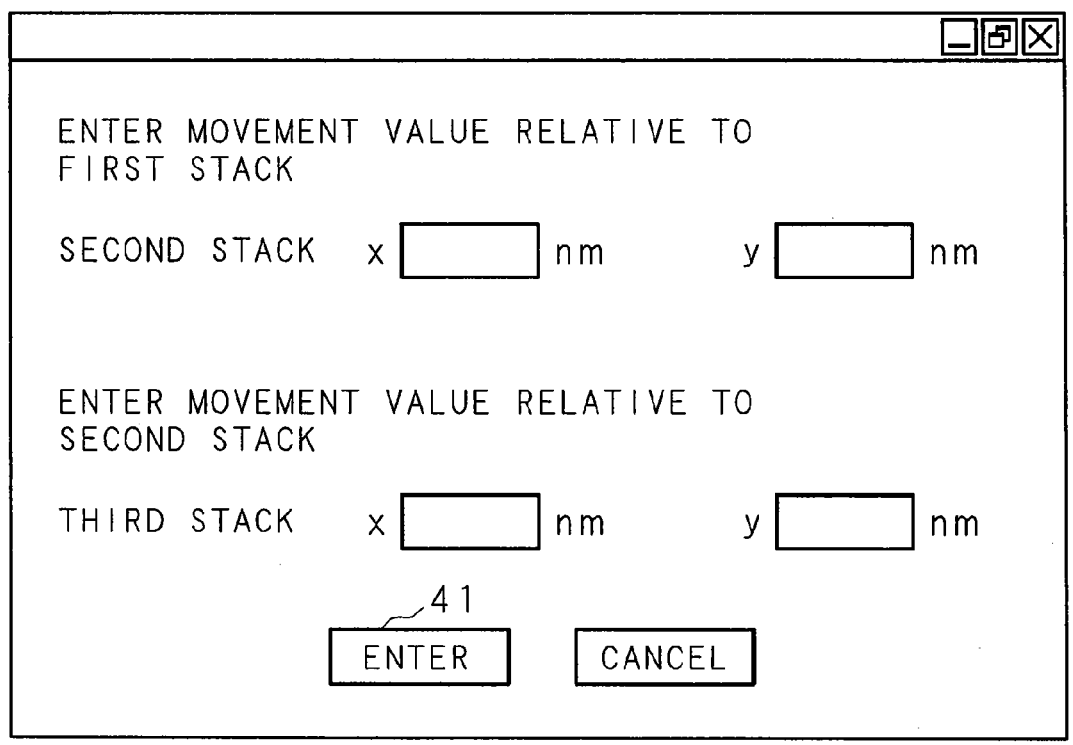
FIG. 26 is an explanation diagram illustrating a conceptual image of a movement value input screen according to Embodiment 4.

FIG. 26 is an explanation diagram illustrating a conceptual image of a movement value input screen according to Embodiment 4. The CPU 11 reads from the storage part 15 the movement value input screen image illustrated in FIG. 26, and then outputs the image onto the display part 14. Through the input part 13, the user inputs a movement value relative to the first stack 31 as the movement value for the second stack 32. Further, through the input part 13, the user inputs a movement value relative to the second stack 32 as the movement value for the third stack 33. Here, a movement value relative to the first stack 31 may be inputted as the movement value for the third stack 33. When the movement values in the X-direction and the Y-direction are inputted through the input part 13 and then the determination button 41 is operated, the CPU 11 receives the inputted movement values for the second stack 32 and the third stack 33. Here, the present embodiment is described for an exemplary case that each is inputted by the unit of nm. However, the movement value may be inputted by another unit such as μm.

The CPU 11 reads the coordinate step number per unit length stored in the storage part 15, and then multiply the coordinate step number by the movement values (length) so as to obtain movement coordinate step numbers for each of the second stack 32 and the third stack 33. Then, the CPU 11 adds to the first reference coordinates the calculated movement coordinate step numbers for the second stack 32, so as to obtain the second reference coordinates. Further, the CPU 11 adds to the second reference coordinates the movement coordinate step numbers for the third stack 33, so as to obtain the third reference coordinates. The CPU 11 stores into the coordinate value file 151 the second reference coordinates and the third reference coordinates having been calculated. FIG. 27 is an explanation diagram illustrating a record layout of the coordinate value file 151 according to Embodiment 4. Further, the third reference coordinate field for the third stack is provided.

Inn the example of FIG. 27, the movement coordinate step numbers of the third stack 33 relative to the second stack 32 are (Ux, Vy). Thus, the third reference coordinates for the set ID 01 become (x1+Sx+Ux, y1+Ty+Vy). With reference to the coordinate value file 151, the CPU 11 controls the movement of the stage, then performs measurement on the first stack 31 at the first reference coordinates, then performs measurement on the second stack 32 at the second reference coordinates, and then performs measurement on the third stack 33 at the third reference coordinates.

FIG. 28 is an explanation diagram illustrating a conceptual image of a relevant information input screen according to Embodiment 4. In Embodiment 4, a model for the third stack 33 is stored in advance in the model file 153. With reference to the first model to the third model stored in the model file 153, the CPU 11 generates a relevant information input screen image, and then outputs the image onto the display part 14. The first model corresponds to the first stack 31, and is constructed from the common film 300 and the first film 301 stacked thereon. The second model corresponds to the second stack 32, and is constructed from the common film 300 and the second film 302 stacked thereon. The third model corresponds to the third stack 33, and is constructed from the common film 300 and the third film 303 stacked thereon. The present embodiment is described for an exemplary case that the film thickness and the optical constants of the common film 300 are common in the parameters in the first model to the third model.

The CPU 11 displays check boxes 300c for lower layer and check boxes 301c for upper layer used for inputting relevant information in accordance with each layer. The user clicks layers and common parameters through the input part 13. In the present embodiment, both of the film thickness and the optical constants are assumed to be common parameters. However, any one of these may solely be a common parameter. When a common film thickness serving as the initial value of the common film 300 and dispersion equation parameters corresponding to the optical constants are inputted through the input part 13, the CPU 11 stores these information pieces into the storage part 15. In the example of FIG. 28, the film thickness and the optical constants of the common film 300 are common parameters as indicated by the corresponding check boxes 300c. When receiving an input of the determination button 41, the CPU 11 stores into the relevant file 154 the relevant information received through the input part 13, that is, the layer and the common parameters. In the process of fitting, the CPU 11 performs fitting with taking such relevant information into consideration, that is, with the condition that the film thickness and the optical constants of the common film 300 are common in the first stack 31 to the third stack 33.

Figure 29A:
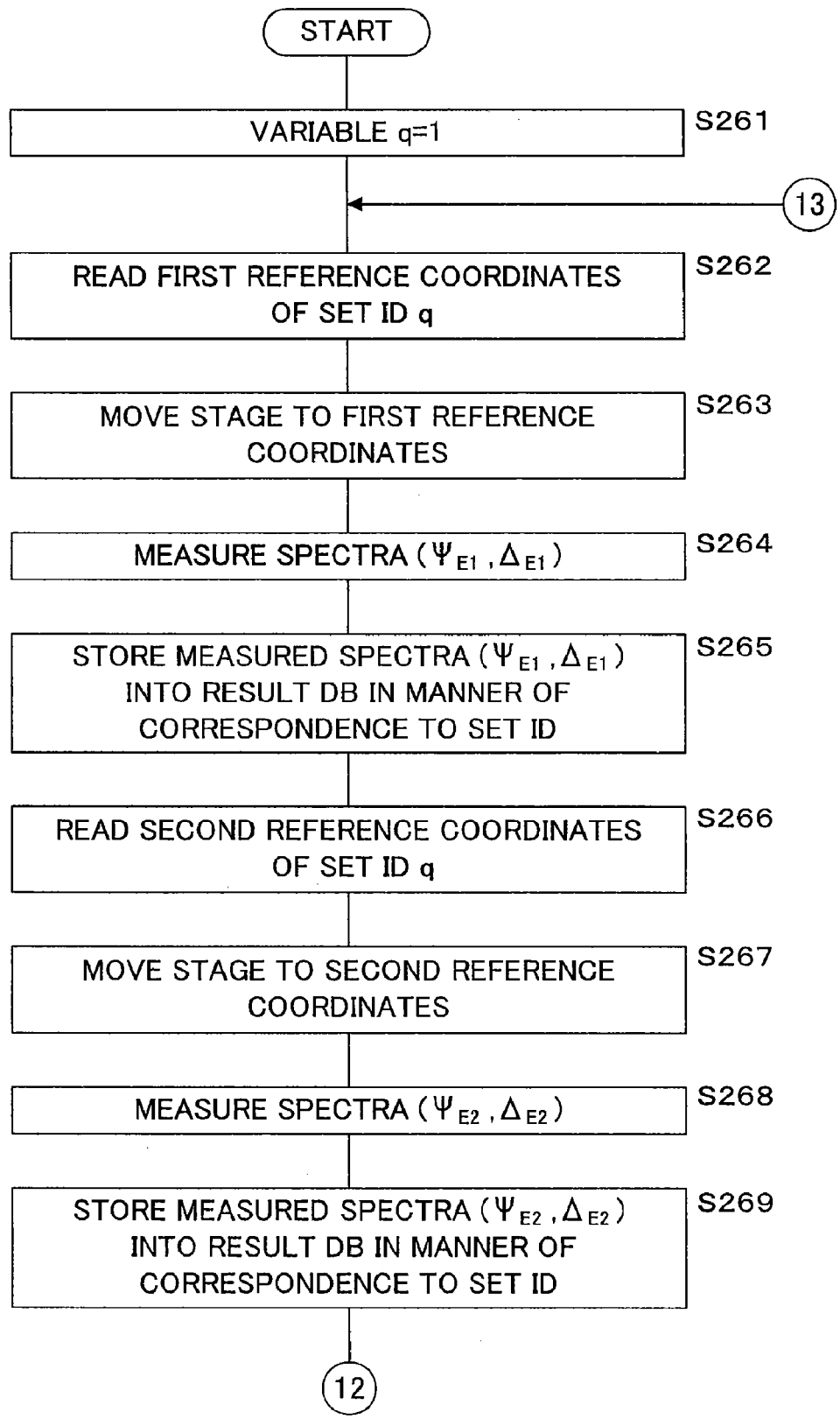
FIGS. 29A and 29B are flow charts illustrating a procedure of measurement processing according to Embodiment 4.
Figure 29B:
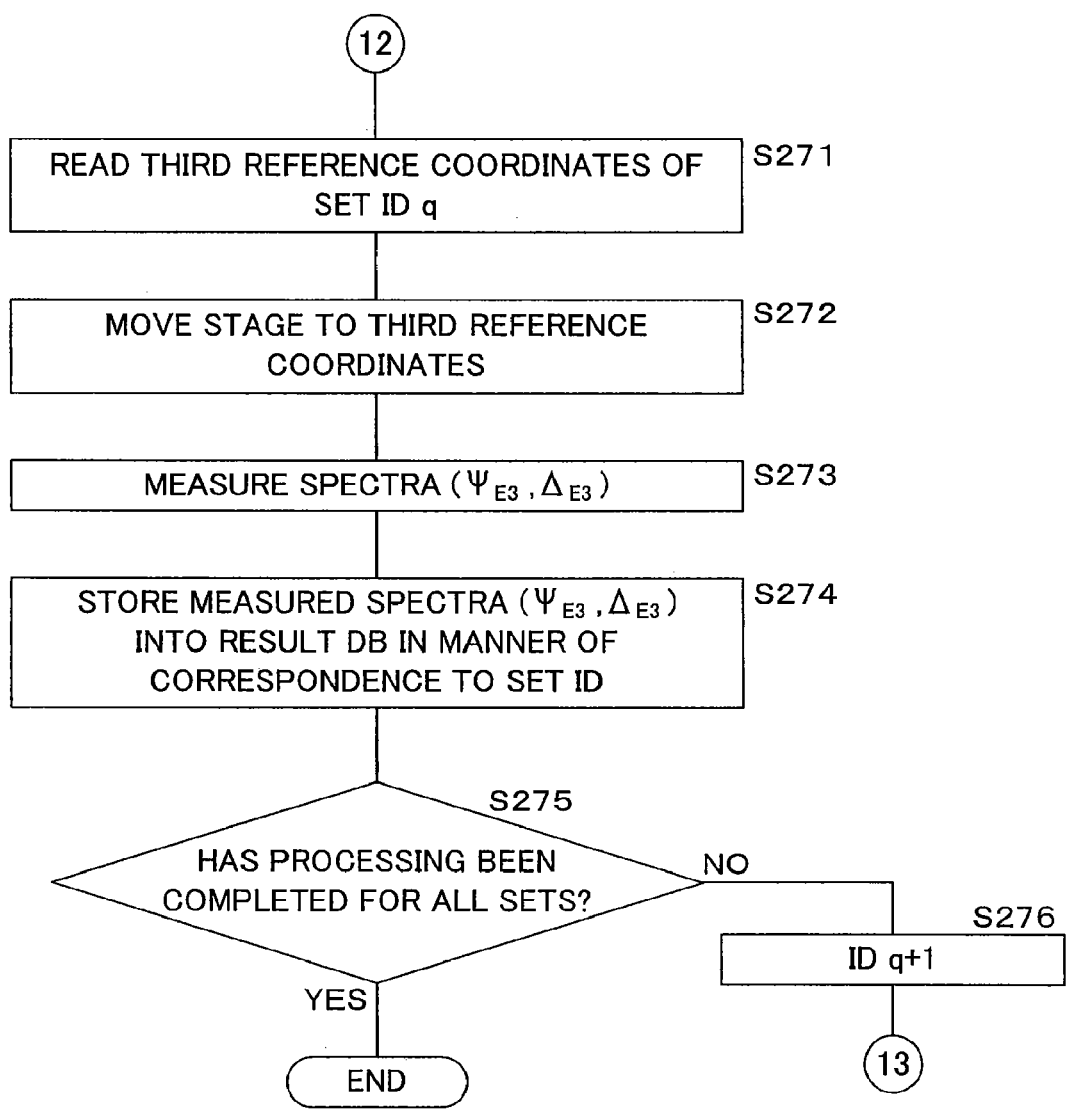

FIGS. 29A and 29B are flow charts illustrating a procedure of measurement processing according to Embodiment 4. The CPU 11 substitutes 1 into the variable q (step S261). The CPU 11 reads from the coordinate value file 151 the first reference coordinates of the set ID q (step S262). When the variable q is 1, the first reference coordinates of the set ID "01" are read. The CPU 11 controls the first motor M1 and the second motor M2 through the motor controller 9 so as to move the stage to the first reference coordinates (step S263). Then, measurement preparation for the first stack 31 is completed. Then, the CPU 11 of the spectroscopic ellipsometer 1 controls the light irradiator 3 and the light obtainer 5 so as to irradiate light onto the first stack 31, and then acquires a measured spectra ($\Psi_{E1}$, $\Delta_{E1}$) (step S264). The CPU 11 receives the measured spectra ($\Psi_{E1}$, $\Delta_{E1}$) outputted from the data acquisition device 8, and then stores the data into the result DB 152 in a manner of correspondence to the set ID (step S265).

The CPU 11 reads from the coordinate value file 151 the second reference coordinates of the set ID q (step S266). The CPU 11 controls the first motor M1 and the second motor M2 through the motor controller 9 so as to move the stage to the second reference coordinates (step S267). Then, measurement preparation for the second stack 32 is completed. Then, the CPU 11 of the spectroscopic ellipsometer 1 controls the light irradiator 3 and the light obtainer 5 so as to irradiate light onto the second stack 32, and then acquires a measured spectra ($\Psi_{E2}$, $\Delta_{E2}$) (step S268).

The CPU 11 receives the measured spectra ($\Psi_{E2}$, $\Delta_{E2}$) outputted from the data acquisition device 8, and then stores the data into the result DB 152 in a manner of correspondence to the set ID (step S269). The CPU 11 reads from the coordinate value file 151 the third reference coordinates of the set ID q (step S271). The CPU 11 controls the first motor M1 and the second motor M2 through the motor controller 9 so as to move the stage to the third reference coordinates (step S272). Then, measurement preparation for the third stack 33 is completed. Then, the CPU 11 of the spectroscopic ellipsometer 1 controls the light irradiator 3 and the light obtainer 5 so as to irradiate light onto the third stack 33, and then acquires a measured spectra ($\Psi_{E3}$, $\Delta_{E3}$) (step S273).

The CPU 11 receives the measured spectra ($\Psi_{E3}$, $\Delta_{E3}$) outputted from the data acquisition device 8, and then stores the data into the result DB 152 in a manner of correspondence to the set ID (step S274). The CPU 11 determines whether the processing has been completed for all sets 30 (step S275). When it is determined that the processing is not yet completed for all sets 30 (NO at step S275), the CPU 11 increments the variable q (step S276). Then, the CPU 11 returns the procedure to step S262, and then acquires the measured spectra of the next set 30. In contrast, when it is determined that the processing has been completed for all sets 30 (YES at step S275), the CPU 11 terminates the series of processing.

Figure 30A:
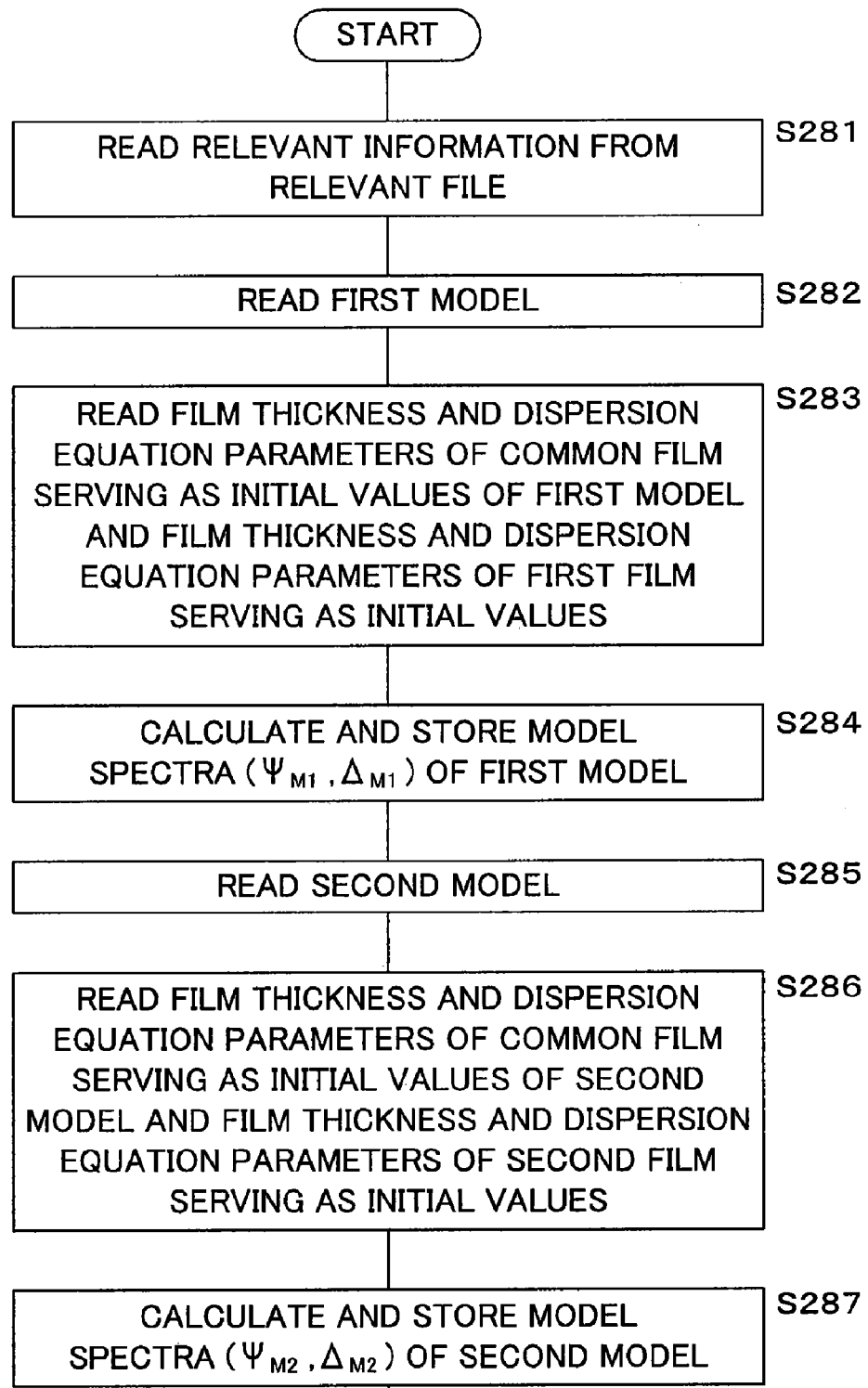
FIGS. 30A to 30C are flow charts illustrating a procedure of fitting processing according to Embodiment 4.
Figure 30B:
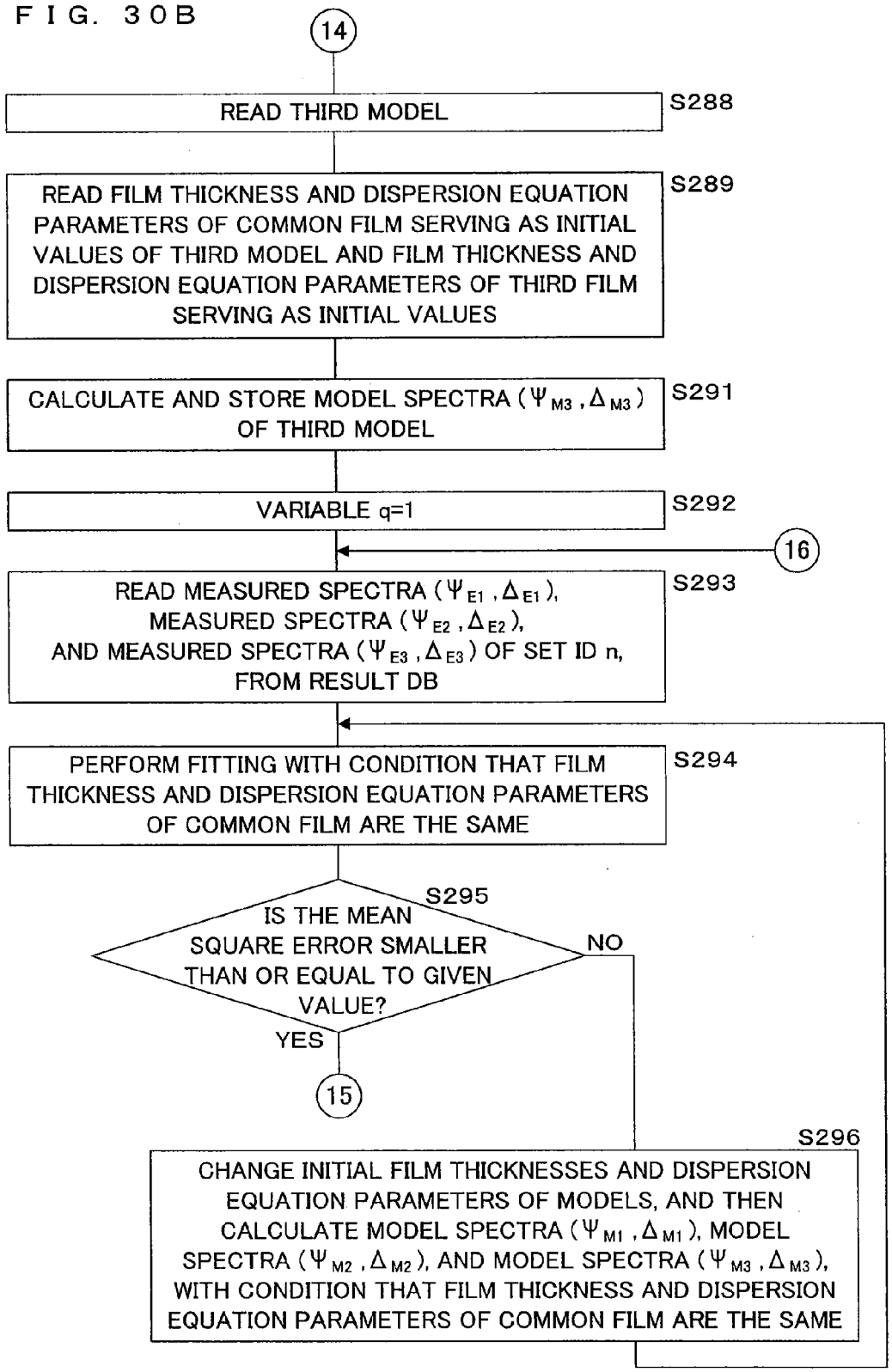
Figure 30C:
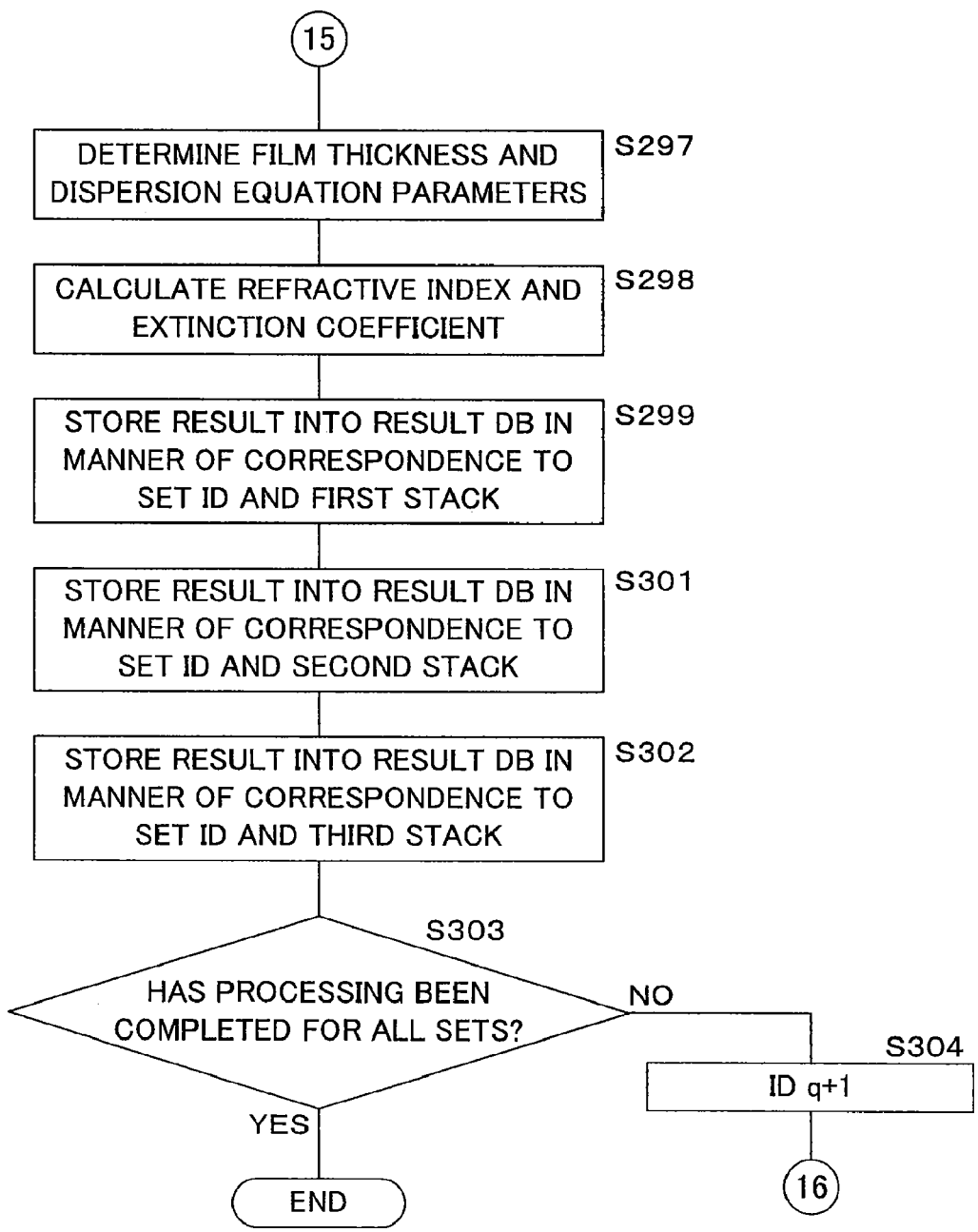

FIGS. 30A to 30C are flow charts illustrating a procedure of fitting processing according to Embodiment 4. The CPU 11 reads the relevant information stored in the relevant file 154 (step S281). The CPU 11 reads the first model from the model file 153 (step S282). In accordance with the read-out first model, the CPU 11 reads from the storage part 15: the film thickness and the dispersion equation parameters of the common film 300 serving as the initial values of the first model stored in advance; and the film thickness and the dispersion equation parameters of the first film 301 serving as the initial values of the first model (step S283). On the basis of the first model, the initial film thickness, and the parameters having been read, the CPU 11 calculates the model spectra ($\Psi_{M1}$, $\Delta_{M1}$) of the first model, and then stores the result into the storage part 15 (step S284).

The CPU 11 reads the second model from the model file 153 (step S285). In accordance with the read-out second model, the CPU 11 reads from the storage part 15: the film thickness and the dispersion equation parameters of the common film 300 serving as the initial values of the second model stored in advance; and the film thickness and the dispersion equation parameters of the second film 302 serving as the initial values of the second model (step S286). On the basis of the second model, the initial film thickness, and the parameters having been read, the CPU 11 calculates the model spectra ($\Psi_{M2}$, $\Delta_{M2}$) of the second model, and then stores the result into the storage part 15 (step S287).

The CPU 11 reads the third model from the model file 153 (step S288). In accordance with the read-out third model, the CPU 11 reads from the storage part 15: the film thickness and the dispersion equation parameters of the common film 300 serving as the initial values of the third model stored in advance; and the film thickness and the dispersion equation parameters of the third film 303 serving as the initial values of the third model (step S289). On the basis of the third model, the initial film thickness, and the parameters having been read, the CPU 11 calculates the model spectra ($\Psi_{M3}$, $\Delta_{M3}$) of the third model, and then stores the result into the storage part 15 (step S291).

The CPU 11 substitutes 1 into the variable q (step S292). Then, the CPU 11 reads from the result DB 152: the measured spectra ($\Psi_{E1}$, $\Delta_{E1}$) concerning the first stack 31 of the set ID q; the measured spectra ($\Psi_{E2}$, $\Delta_{E2}$) concerning the second stack 32; and the measured spectra ($\Psi_{E3}$, $\Delta_{E3}$) concerning the third stack 33 (step S293).

The CPU 11 performs the processing (fitting) of comparing with each other the measured spectra ($\Psi_{E1}$, $\Delta_{E1}$) concerning the first stack 31, the model spectra ($\Psi_{M1}$, $\Delta_{M1}$) of the first model, the measured spectra ($\Psi_{E2}$, $\Delta_{E2}$) concerning the second stack 32, the model spectra ($\Psi_{M2}$, $\Delta_{M2}$) of the second model, the measured spectra ($\Psi_{E3}$, $\Delta_{E3}$) concerning the third stack 33, and the model spectra ($\Psi_{M3}$, $\Delta_{M3}$) of the third model, which have been read for the purpose of fitting, and then changing the film thicknesses, the dispersion equation parameters, and the like such as to minimize the difference between each measured spectra and each model spectra with the condition that the film thickness and the dispersion equation parameters of the common film 300 are the same (step S294). As a result of the fitting, the CPU 11 obtains a mean square error $\chi^2$ according to the least square method. The mean square error $\chi^2$ at step S294 is calculated in accordance with equation (7).

As a result of the fitting, the CPU 11 determines whether the calculated mean square error is smaller than or equal to a given value (step S295). This given value is stored in the storage part 15. When it is determined that the calculated mean square error is not smaller than or equal to the given value (NO at step S295), the CPU 11 goes to step S296. With the condition that the film thickness and the dispersion equation parameters of the common film 300 are the same, the CPU 11 appropriately changes the film thicknesses and the dispersion equation parameters having been set up as initial values of the models, and then re-calculates the model spectra ($\Psi_{M1}$, $\Delta_{M1}$), the model spectra ($\Psi_{M2}$, $\Delta_{M2}$), and the model spectra ($\Psi_{M3}$, $\Delta_{M3}$) (step S296). This change may be performed by the CPU 11, or alternatively by the operator. After that, the procedure goes to step S294 again, so that similar processing is repeated.

When it is determined that the calculated mean square error is smaller than or equal to the given value (YES at step S295), the CPU 11 determines the film thickness and the dispersion equation parameters of each layer of the first stack 31, the film thickness and the dispersion equation parameters of each layer of the second stack 32, and the film thickness and the dispersion equation parameters of each layer of the third stack 33 (step S297). Here, since the condition that the film thickness and the dispersion equation parameters of the common film 300 are the same is adopted, the film thickness of the common film 300 becomes the same in the first stack 31 to the third stack 33. Further, similarly to the film thickness, the refractive index and the extinction coefficient of the common film 300 obtained from the dispersion equation parameters are common in the first stack 31 to the third stack 33. With reference to the dispersion equation parameters and the like of the common film 300 and the first film 301, the CPU 11 calculates the refractive index and the extinction coefficient of the common film 300 and the first film 301 of the first stack 31, then with reference to the dispersion equation parameters and the like of the common film 300 and the second film 302, calculates the refractive indices and the extinction coefficients of the common film 300 and the second film 302 of the second stack 32, and then with reference to the dispersion equation parameters and the like of the common film 300 and the third film 303 calculates the refractive indices and the extinction coefficients of the common film 300 and the third film 303 of the third stack 33 (step S298).

The CPU 11 stores into the result DB 152 the film thickness, the refractive index, and the extinction coefficient of each of the common film 300 and the first film 301 in a manner of correspondence to the set ID and the first stack 31 (step S299). Similarly, the CPU 11 stores into the result DB 152 the film thickness, the refractive index, and the extinction coefficient of each of the common film 300 and the second film 302 in a manner of correspondence to the set ID and the second stack 32 (step S301). The CPU 11 stores into the result DB 152 the film thickness, the refractive index, and the extinction coefficient of each of the common film 300 and the third film 303 in a manner of correspondence to the set ID and the third stack 33 (step S302).

The CPU 11 determines whether the processing has been completed for all sets 30 (step S303). When it is determined that the processing is not yet completed for all sets 30 (NO at step S303), the CPU 11 increments the variable q (step S304). The CPU 11 returns the procedure to step S293 so as to perform fitting on the next set 30. In contrast, when it is determined that the processing has been completed for all sets 30 (YES at step S303), the CPU 11 terminates the series of processing. According to this approach, even in a case of an increased number of stacks in the set 30, merely when correspondence between positions and models is established in advance, measurement on a plurality of sets 30 serving as measurement targets of the sample 50 is achieved without a large amount of time and effort. Further, when at least one parameter is made common throughout the set 30, the film thickness or the optical constants are calculated more precisely.

In the present Embodiment 4, the configuration given above is employed. The other points in the configuration and the operation are similar to those of Embodiments 1 to 3. Thus, corresponding parts are designated by like reference numerals, and their detailed description is omitted.

Embodiment 5

Figure 31:
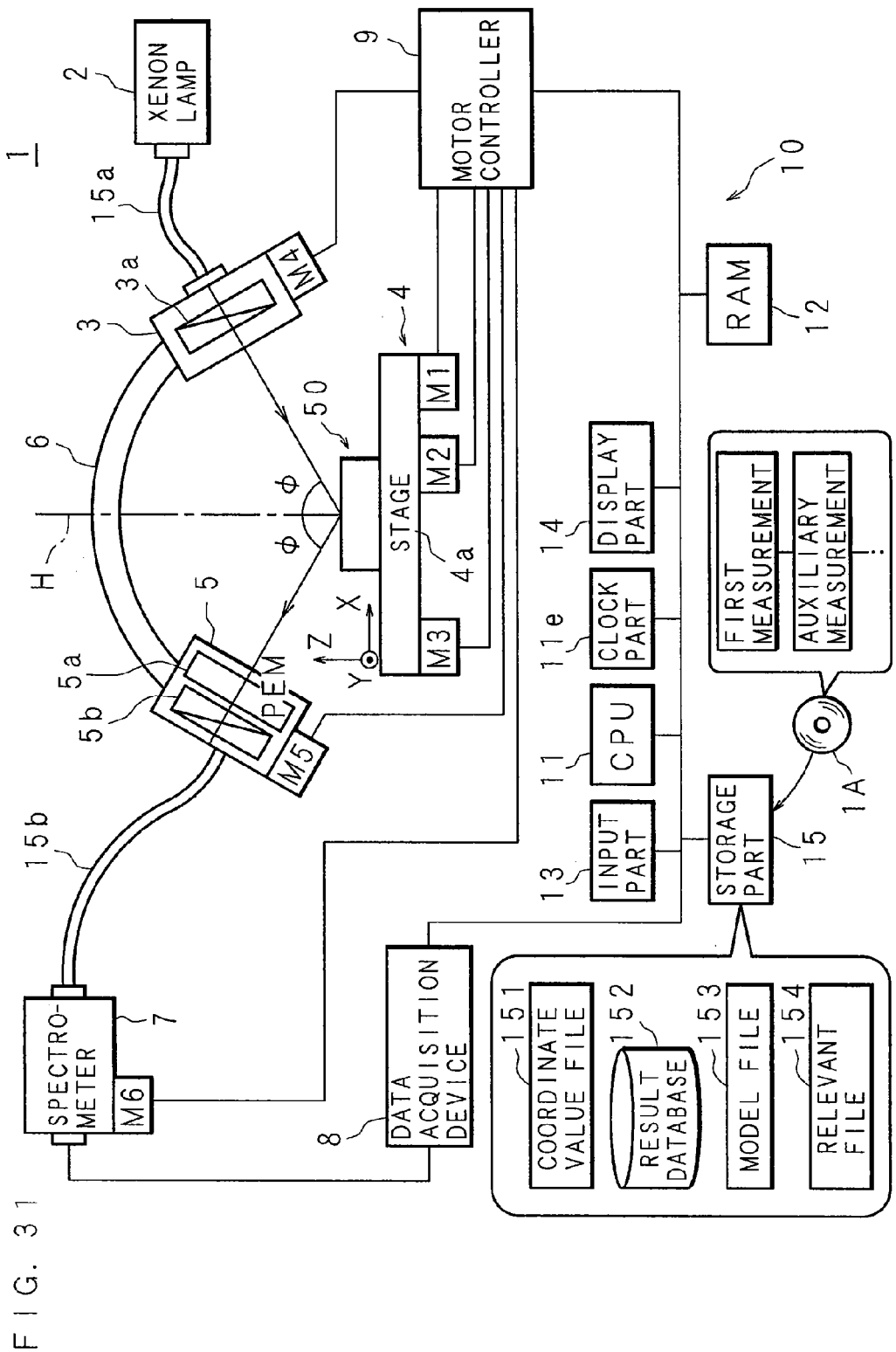
FIG. 31 is a block diagram illustrating a configuration of a spectroscopic ellipsometer according to Embodiment 5.

FIG. 31 is a block diagram illustrating a configuration of a spectroscopic ellipsometer 1 according to Embodiment 5. A computer program for causing the computer 10 of the spectroscopic ellipsometer 1 according to Embodiment 5 to operate may be provided through a portable recording medium 1A such as a CD-ROM and a memory card as described below in the present Embodiment 5. Alternatively, the computer program may be downloaded from a server computer (not illustrated) through a communication network (not illustrated) such as a LAN and the Internet. These are described below.

A portable recording medium 1A that stores a computer program for the execution of the above-mentioned processing is inserted into a recording medium reader (not illustrated) of the computer 10 illustrated in FIG. 31, and then the program is installed within the program in the storage part 15. Alternatively, this program may be downloaded from an external server computer (not illustrated) through a communication part (not illustrated), so as to be installed into the storage part 15. Such a program is loaded onto a RAM 12 and then executed. As a result, the above-mentioned function of the computer 10 is realized.

In the present Embodiment 5, the configuration given above is employed. The other points in the configuration and the operation are similar to those of Embodiments 1 to 4. Thus, corresponding parts are designated by like reference numerals, and their detailed description is omitted.

Embodiment 6

Figure 32A:
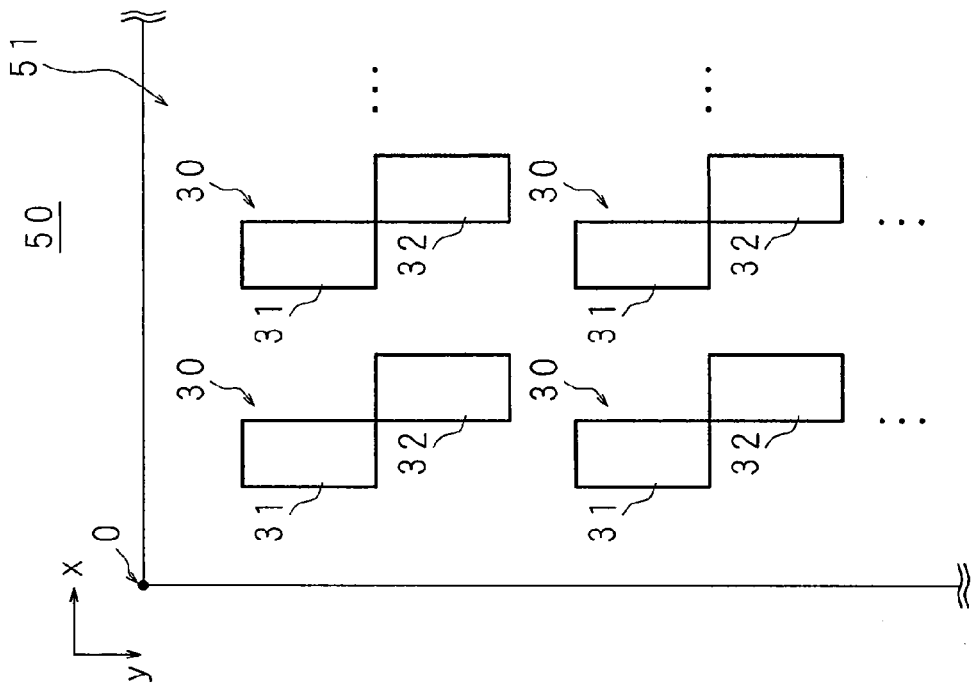
FIG. 32A is a view of a sample of Embodiment 2 in a stack parallel arrangement.
Figure 32B:
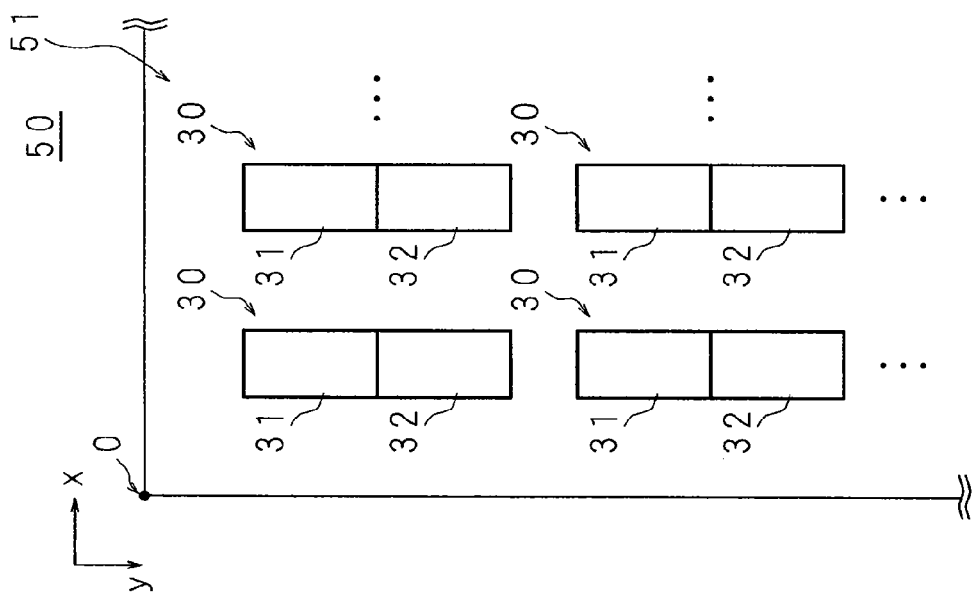
FIG. 32B is a view of a sample in another distribution arrangement

Embodiment 6 relates to another layout of the set 30. FIG. 32 is a plan view of a sample 50 according to another layout. Embodiment 2 has been described for an exemplary case that the second stack 32 is arranged in parallel to the first stack 31 in the X-direction. However, actual implementation is not limited to this. FIG. 32A illustrates an example that a second stack 32 is arranged in parallel to a first stack 31 in the Y-direction. The first stack 31 and the second stack 32 mutually connected in the Y-direction form a set 30. Such sets 30 are distributed in the X-axis and the Y-direction on the substrate 51. FIG. 32B illustrates an example that the point of minimum X-coordinate and minimum Y-coordinates of the second stack 32 contacts with the point of maximum X-coordinate and maximum Y-coordinates of the first stack 31. The sets 30 each constructed by connecting the point of maximum X-coordinate and maximum Y-coordinates of the first stack 31 to the point of minimum X-coordinate and minimum Y-coordinates of the second stack 32 are distributed in the X-axis and the Y-direction on the substrate 51.

In the present Embodiment 6, the configuration given above is employed. The other points in the configuration and the operation are similar to those of Embodiments 1 to 5. Thus, corresponding parts are designated by like reference numerals, and their detailed description is omitted.

Embodiment 7

Embodiment 7 relates to abnormality detection processing for the lower layer film 300 described in Embodiment 2 and the common film 300 described in Embodiments 1, 3, and 4. In addition to the abnormality detection processing for the first stack 31 to the third stack 33 described in Embodiments 1 to 4, abnormality detection processing for the common film 300 (including the lower layer film 300) may be performed.

Figure 33A:
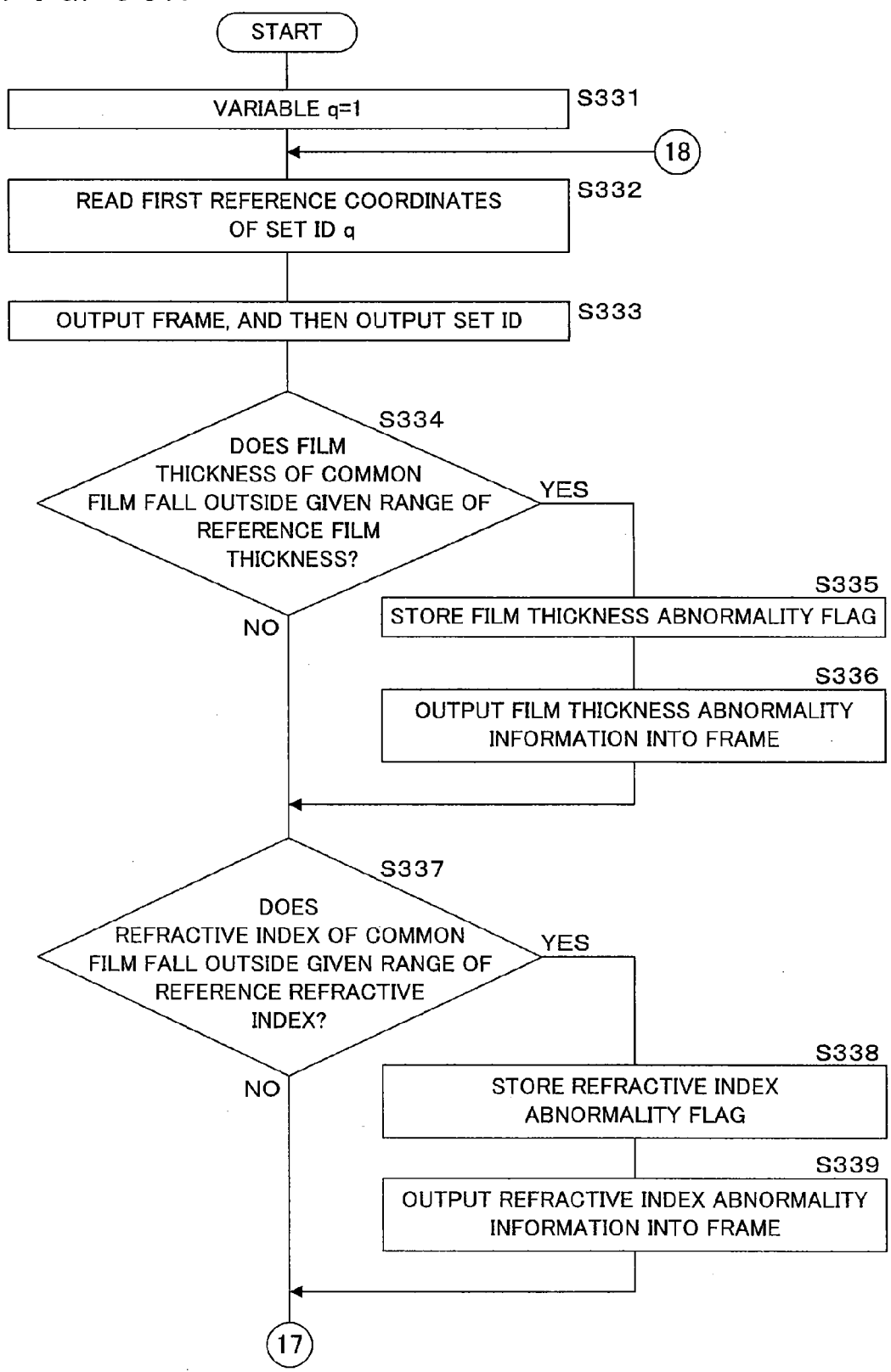
FIGS. 33A and 33B are flow charts illustrating a procedure of abnormality detection processing for a common film.
Figure 33B:
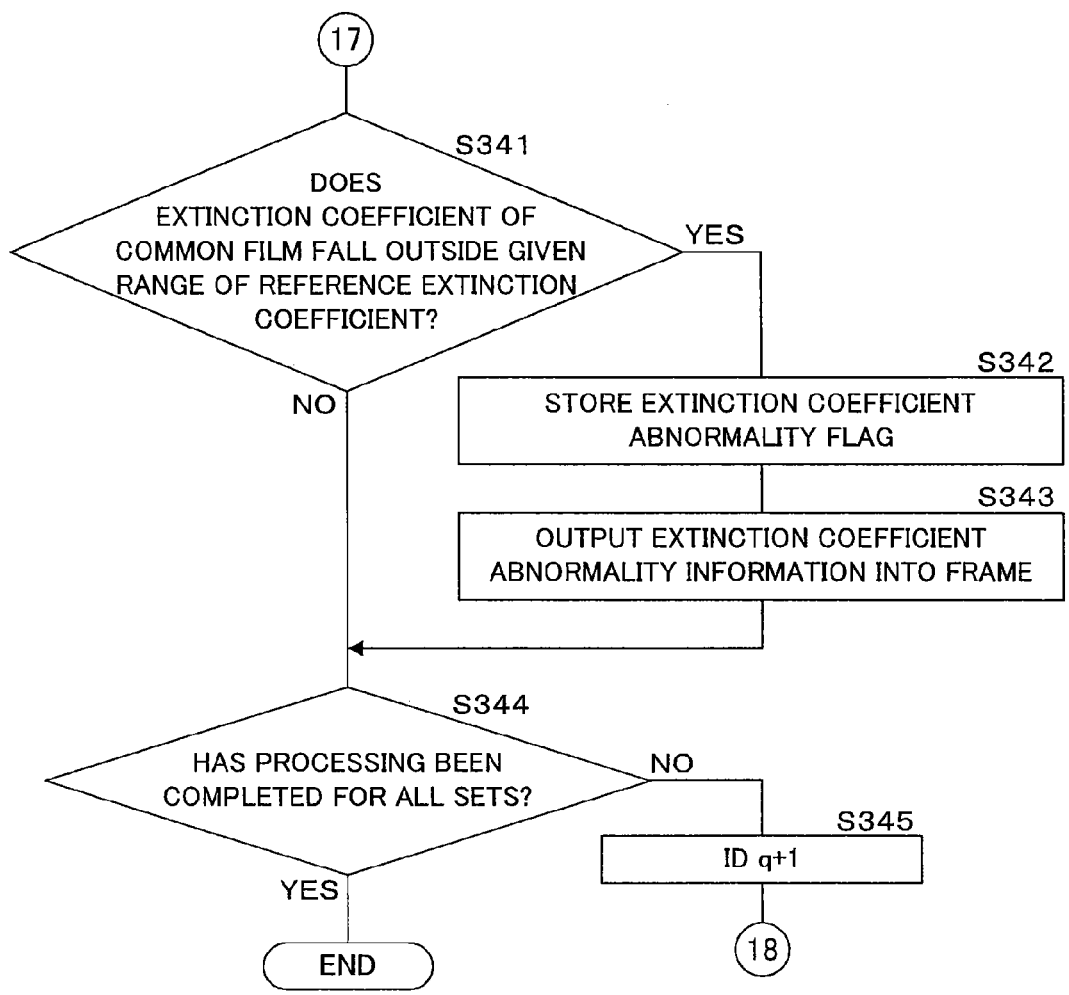

FIGS. 33A and 33B are flow charts illustrating a procedure of abnormality detection processing for the common film 300. The CPU 11 substitutes an initial value 1 into the variable q (step S331). The CPU 11 reads from the coordinate value file 151 the first reference coordinates of the set ID q (step S332). With reference to the first reference coordinates, the CPU 11 outputs one rectangular frame onto the display part 14. Specifically, with reference to the first reference coordinates, the CPU 11 outputs a frame having an area approximately equal to that of the first frame and the second frame corresponding to the common film 300, and then outputs the set ID in the vicinity (step S333).

The CPU 11 reads the film thickness of the common film 300 corresponding to the set ID q stored in the result DB 152. The CPU 11 determines whether the film thickness of the common film 300 falls outside a given range for the reference film thickness stored in advance in the storage part 15 (step S334). When it is determined as falling outside the given range (YES at step S334), the CPU 11 stores into the result DB 152 the film thickness abnormality flag in correspondence to the common film 300 of the set ID q (step S335). The CPU 11 outputs, into the first frame, information indicating the abnormality in the film thickness and the first reference coordinates corresponding to the set ID stored in the coordinate value file 151 (step S336). After this processing, or alternatively when it is determined as not falling outside the given range (NO at step S334), the CPU 11 moves the procedure to step S337.

The CPU 11 reads the refractive index of the common film 300 corresponding to the set ID q stored in the result DB 152. The CPU 11 determines whether the refractive index of the common film 300 falls outside a given range for the reference refractive index stored in advance in the storage part 15 (step S337). When it is determined as falling outside the given range (YES at step S337), the CPU 11 stores into the result DB 152 the refractive index abnormality flag in correspondence to the common film 300 of the set ID q (step S338). The CPU 11 outputs, into the frame, information indicating the abnormality in the refractive index and the first reference coordinates corresponding to the set ID stored in the coordinate value file 151 (step S339). After this processing, or alternatively when it is determined as not falling outside the given range (NO at step S337), the CPU 11 moves the procedure to step S341.

The CPU 11 reads the extinction coefficient of the common film 300 corresponding to the set ID q stored in the result DB 152. The CPU 11 determines whether the extinction coefficient of the common film 300 falls outside a given range for the reference extinction coefficient stored in advance in the storage part 15 (step S341). When it is determined as falling outside the given range (YES at step S341), the CPU 11 stores into the result DB 152 the extinction coefficient abnormality flag in correspondence to the common film 300 of the set ID q (step S342). The CPU 11 outputs, into the frame, information indicating the abnormality in the extinction coefficient and the first reference coordinates corresponding to the set ID stored in the coordinate value file 151 (step S343). After this processing, or alternatively when it is determined as not falling outside the given range (NO at step S341), the CPU 11 moves the procedure to step S344.

The CPU 11 determines whether the processing has been completed for all sets 30 (step S344). When it is determined that the processing is not yet completed for all sets 30 (NO at step S344), the CPU 11 increments the variable q (step S345). The CPU 11 returns the procedure to step S332 so as to perform abnormality detection on the next set 30. In contrast, when it is determined that the processing has been completed for all sets 30 (YES at step S344), the CPU 11 terminates the series of processing.

In the present Embodiment 7, the configuration given above is employed. The other points in the configuration and the operation are similar to those of Embodiments 1 to 6. Thus, corresponding parts are designated by like reference numerals, and their detailed description is omitted.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An optical measurement apparatus for measuring a film thickness or an optical constant of a sample, comprising:
    a storage processing part storing into a storage part a plurality of main reference positions where measurement is to be performed and at least one movement value relative to each main reference position;
    a main measuring part moving a measurement position to one of the main reference positions stored in the storage part, then irradiating light, and then measuring a change in a state of reflected light;
    an auxiliary measuring part moving the measurement position to an auxiliary reference position based on the movement value relative to one of the main reference positions stored in the storage part, then irradiating light, and then measuring a change in a state of reflected light;
    a main calculating part performing analysis on the basis of a main model corresponding to the main reference position stored in the storage part and the change in the state of light measured by the main measuring part, and calculating a film thickness or an optical constant; and
    an auxiliary calculating part performing analysis on the basis of an auxiliary model corresponding to the auxiliary reference position stored in the storage part and the change in the state of light measured by the auxiliary measuring part, and calculating a film thickness or an optical constant.

2. The optical measurement apparatus according to claim 1, wherein
the main measuring part,
after the measurement at the one of the main reference positions, moves a measurement position to another one of the main reference positions stored in the storage part, then irradiates light, and then measures a change in the state of reflected light, and
the auxiliary measuring part,
after the measurement at the auxiliary reference position based on the movement value relative to the one of the main reference positions, moves the measurement position to an auxiliary reference position based on the movement value relative to another one of the main reference positions stored in the storage part, then irradiates light, and then measures a change in the state of reflected light.

3. The optical measurement apparatus according to claim 2, further comprising:
an abnormality signal output part, when the film thickness or the optical constant calculated by the main calculating part falls outside a given range of a reference film thickness or a reference optical constant stored in advance, outputting the corresponding main reference position and a signal indicating the abnormality; and
an auxiliary abnormality signal output part, when the film thickness or the optical constant calculated by the auxiliary calculating part falls outside a given range of a reference film thickness or a reference optical constant stored in advance, outputting the corresponding auxiliary reference position and a signal indicating the abnormality.

4. An optical measurement apparatus measuring a film thickness or an optical constant of a sample, comprising:
a storage processing part storing into a storage part a plurality of main reference positions where measurement is to be performed and at least one movement value relative to each main reference position;
a main measuring part moving a measurement position to one of the main reference positions stored in the storage part, then irradiating light, and then measuring a change in a state of reflected light;
an auxiliary measuring part moving the measurement position to an auxiliary reference position based on the movement value relative to one of the main reference positions stored in the storage part, then irradiating light, and then measuring a change in a state of reflected light;
a parameter storage processing part storing into the storage part a parameter common to both models of a main model corresponding to the main reference position stored in the storage part and an auxiliary model corresponding to the auxiliary reference position; and
a calculating part performing analysis on the basis of the main model and the auxiliary model that contain the common parameter stored in the storage part and on the basis of the change in the state of light measured by the main measuring part and the change in the state of light measured by the auxiliary measuring part, and calculating a film thickness or an optical constant.

5. The optical measurement apparatus according to claim 4, wherein
the main measuring part,
after the measurement at the one of the main reference positions, moves a measurement position to another one of the main reference positions stored in the storage part, then irradiates light, and then measures a change in a state of reflected light, and
the auxiliary measuring part,
after the measurement at the auxiliary reference position based on the movement value relative to the one of the main reference positions, moves the measurement position to an auxiliary reference position based on the movement value relative to another one of the main reference positions stored in the storage part, then irradiates light, and then measures a change in a state of reflected light.

6. The optical measurement apparatus according to claim 5, further comprising
an abnormality signal output part, when the film thickness or the optical constant calculated by the calculating part falls outside a given range of a reference film thickness or a reference optical constant stored in advance, outputting the corresponding main reference position or auxiliary reference position and a signal indicating the abnormality.

7. The optical measurement apparatus according to claim 4, wherein
a film thickness of at least one layer common to both models of the main model and the auxiliary model is adopted as a common parameter, and
the calculating part
performs analysis on the basis of the main model and the auxiliary model that contain the common parameter including the film thickness of the one layer and on the basis of the change in the state of light measured by the main measuring part and the change in the state of light measured by the auxiliary measuring part, and calculates a film thickness or an optical constant at the main reference position and the auxiliary reference position.

8. A spectroscopic ellipsometer for measuring a film thickness or an optical constant of a sample, comprising:
a storage processing part storing into a storage part a plurality of main reference positions where measurement is to be performed and at least one movement value relative to each main reference position;
a main measuring part moving a measurement position to one of the main reference positions stored in the storage part, then irradiating light, and then measuring a polarization state of reflected light;
an auxiliary measuring part moving the measurement position to an auxiliary reference position based on the movement value relative to one of the main reference positions stored in the storage part, then irradiating light, and then measuring a polarization state of reflected light;
a parameter storage processing part storing into the storage part a parameter common to both models of a main model corresponding to the main reference position stored in the storage part and an auxiliary model corresponding to the auxiliary reference position; and
a calculating part performing analysis on the basis of the main model and the auxiliary model that contain the common parameter stored in the storage part and on the basis of the polarization state of light measured by the main measuring part and the polarization state of light measured by the auxiliary measuring part, and calculating a film thickness or an optical constant.

9. The spectroscopic ellipsometer according to claim 8, wherein
the storage processing part
stores into the storage part a plurality of main reference positions where measurement is to be performed and a plurality of movement values for each main reference position, the auxiliary measuring part
moves the measurement position to each of a plurality of auxiliary reference positions based on the plurality of movement values relative to one of the main reference positions stored in the storage part, then irradiates light, and then measures a polarization state of reflected light,
a main model and a plurality of auxiliary models are stored in the storage part while a film thickness of at least one layer common in the main model and the plurality of auxiliary models is adopted as a common parameter, and
the calculating part
performs analysis on the basis of the main model and the plurality of auxiliary models that contain the common parameter including the film thickness of the one layer and on the basis of the polarization state of light measured by the main measuring part and the polarization state of light concerning a plurality of auxiliary reference positions measured by the auxiliary measuring part, and calculates a film thickness or an optical constant at the main reference position and the plurality of auxiliary reference positions.

10. An optical measurement apparatus for measuring a film thickness or an optical constant of a sample, comprising:
storage means storing into a storage part a plurality of main reference positions where measurement is to be performed and at least one movement value relative to each main reference position;
main measuring means moving a measurement position to one of the main reference positions stored in the storage part, then irradiating light, and then measuring a change in a state of reflected light;
auxiliary measuring means moving the measurement position to an auxiliary reference position based on the movement value relative to one of the main reference positions stored in the storage part, then irradiating light, and then measuring a change in a state of reflected light;
main calculating means performing analysis on the basis of a main model corresponding to the main reference position stored in the storage part and the change in the state of light measured by the main measuring means, and calculating a film thickness or an optical constant; and
auxiliary calculating means performing analysis on the basis of an auxiliary model corresponding to the auxiliary reference position stored in the storage part and the change in the state of light measured by the auxiliary measuring means, and calculating a film thickness or an optical constant.

11. The optical measurement apparatus according to claim 10, wherein
the main measuring means,
after the measurement at the one of the main reference positions, moves a measurement position to another one of the main reference positions stored in the storage part, then irradiates light, and then measures a change in a state of reflected light, and
the auxiliary measuring means,
after the measurement at the auxiliary reference position based on the movement value relative to the one of the main reference positions, moves the measurement position to an auxiliary reference position based on the movement value relative to another one of the main reference positions stored in the storage part, then irradiates light, and then measures a change in a state of reflected light.

12. The optical measurement apparatus according to claim 11, further comprising:
means, when the film thickness or the optical constant calculated by the main calculating means falls outside a given range of a reference film thickness or a reference optical constant stored in advance, outputting the corresponding main reference position and a signal indicating the abnormality; and
means, when the film thickness or the optical constant calculated by the auxiliary calculating means falls outside a given range of a reference film thickness or a reference optical constant stored in advance, outputting the corresponding auxiliary reference position and a signal indicating the abnormality.

13. An optical measurement apparatus for measuring a film thickness or an optical constant of a sample:
storage means storing into a storage part a plurality of main reference positions where measurement is to be performed and at least one movement value relative to each main reference position;
main measuring means moving a measurement position to one of the main reference positions stored in the storage part, then irradiating light, and then measuring a change in a state of reflected light;
auxiliary measuring means moving the measurement position to an auxiliary reference position based on the movement value relative to one of the main reference positions stored in the storage part, then irradiating light, and then measuring a change in a state of reflected light;
means storing into the storage part a parameter common to both models of a main model corresponding to the main reference position stored in the storage part and an auxiliary model corresponding to the auxiliary reference position; and
calculating means performing analysis on the basis of the main model and the auxiliary model that contain the common parameter stored in the storage part and on the basis of the change in the state of light measured by the main measuring means and the change in the state of light measured by the auxiliary measuring means, and calculating a film thickness or an optical constant.

14. The optical measurement apparatus according to claim 13, wherein
the main measuring means,
after the measurement at the one of the main reference positions, moves a measurement position to another one of the main reference positions stored in the storage part, then irradiates light, and then measures a change in a state of reflected light, and
the auxiliary measuring means,
after the measurement at the auxiliary reference position based on the movement value relative to the one of the main reference positions, moves the measurement position to an auxiliary reference position based on the movement value relative to another one of the main reference positions stored in the storage part, then irradiates light, and then measures a change in a state of reflected light.

15. The optical measurement apparatus according to claim 14, further comprising
means, when the film thickness or the optical constant calculated by the calculating means falls outside a given range of a reference film thickness or a reference optical constant stored in advance, outputting the corresponding main reference position or auxiliary reference position and a signal indicating the abnormality.

16. The optical measurement apparatus according to claim 13, wherein
a film thickness of at least one layer common to both models of the main model and the auxiliary model is adopted as a common parameter, and
the calculating means
performs analysis on the basis of the main model and the auxiliary model that contain the common parameter including the film thickness of the one layer and on the basis of the change in the state of light measured by the main measuring means and the change in the state of light measured by the auxiliary measuring means, and calculates a film thickness or an optical constant at the main reference position and the auxiliary reference position.

17. The spectroscopic ellipsometer for measuring a film thickness or an optical constant of a sample, comprising:
storage means storing into a storage part a plurality of main reference positions where measurement is to be performed and at least one movement value relative to each main reference position;
main measuring means moving a measurement position to one of the main reference positions stored in the storage part, then irradiating light, and then measuring a polarization state of reflected light;
auxiliary measuring means moving the measurement position to an auxiliary reference position based on the movement value relative to one of the main reference positions stored in the storage part, then irradiating light, and then measuring a polarization state of reflected light;
means storing into the storage part a parameter common to both models of a main model corresponding to the main reference position stored in the storage part and an auxiliary model corresponding to the auxiliary reference position; and
calculating means performing analysis on the basis of the main model and the auxiliary model that contain the common parameter stored in the storage part and on the basis of the polarization state of light measured by the main measuring means and the polarization state of light measured by the auxiliary measuring means, and calculating a film thickness or an optical constant.

18. A recording medium storing a program causing a computer provided in an optical measurement apparatus to perform operation, wherein the program causes the computer to execute processing comprising:
a main measurement step of moving a measurement position to one of main reference positions stored in a storage part storing a plurality of main reference positions where measurement is to be performed and at least one movement value relative to each main reference position, then irradiating light, and then measuring a change in a state of reflected light;
an auxiliary measurement step of moving the measurement position to an auxiliary reference position based on the movement value relative to one of the main reference positions stored in the storage part, then irradiating light, and then measuring a change in a state of reflected light;
a main calculation step of performing analysis on the basis of a main model corresponding to the main reference position stored in the storage part and the change in the state of light measured at the main measurement step, and calculating a film thickness or an optical constant; and
an auxiliary calculation step of performing analysis on the basis of an auxiliary model corresponding to the auxiliary reference position stored in the storage part and the change in the state of light measured at the auxiliary measurement step, and calculating a film thickness or an optical constant.

19. A recording medium storing a program causing a computer provided in an optical measurement apparatus to perform operation, wherein the program causes the computer to execute processing comprising:
a main measurement step of moving a measurement position to one of main reference positions stored in a storage part storing a plurality of main reference positions where measurement is to be performed and at least one movement value relative to each main reference position, then irradiating light, and then measuring a change in a state of reflected light;
an auxiliary measurement step of moving the measurement position to an auxiliary reference position based on the movement value relative to one of the main reference positions stored in the storage part, then irradiating light, and then measuring a change in a state of reflected light; and
a calculation step of performing analysis on the basis of the main model and the auxiliary model that contain the parameter common to both models of the main model with respect to the main reference position stored in the storage part and the auxiliary model corresponding to the auxiliary reference position and on the basis of the change in the state of light measured by the main measuring means and the change in the state of light measured by the auxiliary measuring means, and calculating a film thickness or an optical constant.

20. A measurement method of measuring a film thickness or an optical constant of a sample by using an optical measurement apparatus having a control part, comprising:
a main measurement step of moving a measurement position to one of main reference positions stored in a storage part storing a plurality of main reference positions where measurement is to be performed and at least one movement value relative to each main reference position, then irradiating light, and then measuring a change in a state of reflected light by means of the control part;
an auxiliary measurement step of moving the measurement position to an auxiliary reference position based on the movement value relative to one of the main reference positions stored in the storage part, then irradiating light, and then measuring a change in a state of reflected light by means of the control part;
a main calculation step of performing analysis on the basis of a main model corresponding to the main reference position stored in the storage part and the change in the state of light measured at the main measurement step, and calculating a film thickness or an optical constant by means of the control part; and
an auxiliary calculation step of performing analysis on the basis of an auxiliary model corresponding to the auxiliary reference position stored in the storage part and the change in the state of light measured at the auxiliary measurement step, and calculating a film thickness or an optical constant.

\* \* \* \* \*